(12) United States Patent
Wilt et al.

(10) Patent No.: US 9,851,080 B2
(45) Date of Patent: Dec. 26, 2017

(54) USER-WEARABLE ILLUMINATION ASSEMBLY

(71) Applicant: Kerr Corporation, Orange, CA (US)

(72) Inventors: Brian L. Wilt, Appleton, WI (US);
James Onderak, Sun Prairie, WI (US);
Owen J. Gill, Southbury, CT (US);
Shane Siegel, Janesville, WI (US)

(73) Assignee: Kerr Corporation, Orange, CA (US)

( * ) Notice: Subject to any disclaimer, the term of this patent is extended or adjusted under 35 U.S.C. 154(b) by 239 days.

(21) Appl. No.: 14/847,737

(22) Filed: Sep. 8, 2015

(65) Prior Publication Data

US 2015/0377462 A1 Dec. 31, 2015

Related U.S. Application Data

(60) Division of application No. 13/314,329, filed on Dec. 8, 2011, now abandoned, which is a (Continued)

(51) Int. Cl.
*F21V 21/084* (2006.01)
*F21V 21/002* (2006.01)
(Continued)

(52) U.S. Cl.
CPC .......... *F21V 21/084* (2013.01); *A61B 90/11* (2016.02); *F21L 4/02* (2013.01); *F21V 21/002* (2013.01);
(Continued)

(58) Field of Classification Search
CPC .............. A41D 27/085; A61B 1/00195; A61B 1/00197; A61B 1/06; A61B 1/24; F21W 2131/202; G02B 25/02; F21V 21/084
See application file for complete search history.

(56) References Cited

U.S. PATENT DOCUMENTS 1,741,264 A 12/1929 Wappler
2,229,310 A 1/1941 Saslaw
(Continued)

FOREIGN PATENT DOCUMENTS

DE 102006015334 A1 10/2007
WO 03019267 A1 3/2003

OTHER PUBLICATIONS

U.S. Patent and Trademark Office; Office Action in U.S. Appl. No. 13/314,329 dated Feb. 25, 2016; 24 pages.

*Primary Examiner* — Jong-Suk (James) Lee
*Assistant Examiner* — Leah S Macchiarolo
(74) *Attorney, Agent, or Firm* — Sheppard, Mullin, Richter & Hampton LLP

(57) ABSTRACT

In one aspect, a user-wearable illumination assembly includes eyeglass frames and a headlamp removably coupled to the eyeglass frames. Electrical circuitry may be integrated with the eyeglass frames. The headlamp and the eyeglass frames have mounting structure that cooperate to removably support the headlamp thereon. A light source is disposed within the headlamp and electrical communication between the light source and the electrical circuitry of the eyeglass frames is provided by electrical contacts associated with the mounting structures of the headlamp and eyeglass frames. In another aspect, a user-wearable illumination assembly for use with eyeglass frames includes a clip assembly that is selectively removably couplable to a bridge portion of the eyeglass frames, and a headlamp coupled to the clip assembly. The illumination assembly further includes a battery that is selectively removably couplable to the eyeglass frames and at least one electrical conductor coupling the battery to the headlamp.

8 Claims, 63 Drawing Sheets

Related U.S. Application Data continuation-in-part of application No. PCT/US2010/037743, filed on Jun. 8, 2010.

(60) Provisional application No. 61/298,346, filed on Feb. 8, 2010, provisional application No. 61/185,454, filed on Jun. 9, 2009.

(51) Int. Cl.
| | |
|---|---|
| *F21V 21/088* | (2006.01) |
| *F21V 23/04* | (2006.01) |
| *F21V 33/00* | (2006.01) |
| *G02C 7/08* | (2006.01) |
| *G02C 11/04* | (2006.01) |
| *F21L 4/02* | (2006.01) |
| *A61B 90/11* | (2016.01) |
| *A61C 1/08* | (2006.01) |
| *F21W 131/20* | (2006.01) |
| *F21W 131/202* | (2006.01) |
| *F21W 131/205* | (2006.01) |
| *F21W 131/30* | (2006.01) |
| *A61B 90/50* | (2016.01) |
| *F21Y 115/10* | (2016.01) |

(52) U.S. Cl.
CPC ...... *F21V 21/0885* (2013.01); *F21V 23/0414* (2013.01); *F21V 33/0004* (2013.01); *G02C 7/08* (2013.01); *G02C 11/04* (2013.01); *A61B 2090/502* (2016.02); *A61C 1/088* (2013.01); *F21W 2131/20* (2013.01); *F21W 2131/202* (2013.01); *F21W 2131/205* (2013.01); *F21W 2131/30* (2013.01); *F21Y 2115/10* (2016.08)

(56) References Cited

U.S. PATENT DOCUMENTS

| | | |
|---|---|---|
| 2,725,462 A | 11/1955 | Vorgang |
| 3,008,040 A | 11/1961 | Moore |
| 3,350,552 A | 10/1967 | Lawrence |
| 4,195,918 A * | 4/1980 | Freche .................. A61B 1/07 128/201.12 |
| 4,283,127 A | 8/1981 | Rosenwinkel et al. |
| 4,794,496 A | 12/1988 | Lanes et al. |
| 4,970,631 A | 11/1990 | Marshall |
| 4,991,951 A | 2/1991 | Mizuno et al. |
| 5,448,318 A | 9/1995 | Heine et al. |
| 5,579,158 A | 11/1996 | Padula |
| 5,667,291 A | 9/1997 | Caplan et al. |
| D388,113 S | 12/1997 | Feinbloom |
| 5,722,762 A | 3/1998 | Soll |
| D405,901 S | 2/1999 | Feinbloom et al. |
| 5,946,071 A | 8/1999 | Feldman |
| 5,980,037 A | 11/1999 | Conway |
| D428,431 S | 7/2000 | Jordan |
| D429,751 S | 8/2000 | Garrity et al. |
| D441,886 S | 5/2001 | Beck |
| 6,277,068 B1 | 8/2001 | Wojnowicz et al. |
| 6,290,368 B1 | 9/2001 | Lehrer |
| 6,390,640 B1 | 5/2002 | Wong et al. |
| 6,497,495 B1 | 12/2002 | Janz |
| 6,604,847 B2 | 8/2003 | Lehrer |
| 6,612,696 B2 | 9/2003 | Waters |
| 6,623,141 B2 | 9/2003 | Lehrer |
| 6,764,194 B1 | 7/2004 | Cooper |
| 6,824,265 B1 | 11/2004 | Harper |
| 6,863,416 B2 | 3/2005 | Waters |
| 6,955,444 B2 | 10/2005 | Gupta |
| 6,974,226 B2 | 12/2005 | Chang |
| 7,008,074 B1 | 3/2006 | Halm |
| RE39,162 E | 7/2006 | Caplan et al. |
| 7,104,670 B2 | 9/2006 | Waters |
| 7,168,821 B2 | 1/2007 | Huang |
| 7,192,151 B2 | 3/2007 | Clupper et al. |
| 7,210,810 B1 | 5/2007 | Iversen et al. |
| 7,281,826 B2 | 10/2007 | Huang |
| 7,370,991 B1 | 5/2008 | Ellis-Fant |
| 7,377,664 B2 | 5/2008 | Waters |
| 7,422,324 B2 | 9/2008 | Lee |
| 7,425,066 B2 | 9/2008 | Blum et al. |
| 7,465,065 B2 | 12/2008 | Marka |
| 7,490,949 B2 | 2/2009 | Medinis |
| 7,607,775 B2 | 10/2009 | Hermanson et al. |
| 7,611,241 B2 | 11/2009 | Chen et al. |
| 7,695,155 B1 | 4/2010 | Hou |
| 7,874,669 B2 | 1/2011 | Moritz et al. |
| D650,106 S | 12/2011 | Schussler |
| 8,979,295 B2 | 3/2015 | Waters |
| 2004/0057229 A1 | 3/2004 | Thomas |
| 2006/0012974 A1 | 1/2006 | Su |
| 2007/0013864 A1 | 1/2007 | Dietz |
| 2007/0159810 A1 | 7/2007 | Kim |
| 2008/0068824 A1 | 3/2008 | Wang |
| 2008/0239707 A1 | 10/2008 | Feinbloom et al. |
| 2008/0310145 A1 * | 12/2008 | Blake .................. A61B 90/35 362/105 |
| 2012/0281390 A1 | 11/2012 | Nakamura |
| 2015/0015161 A1 | 1/2015 | Nakamura |

\* cited by examiner

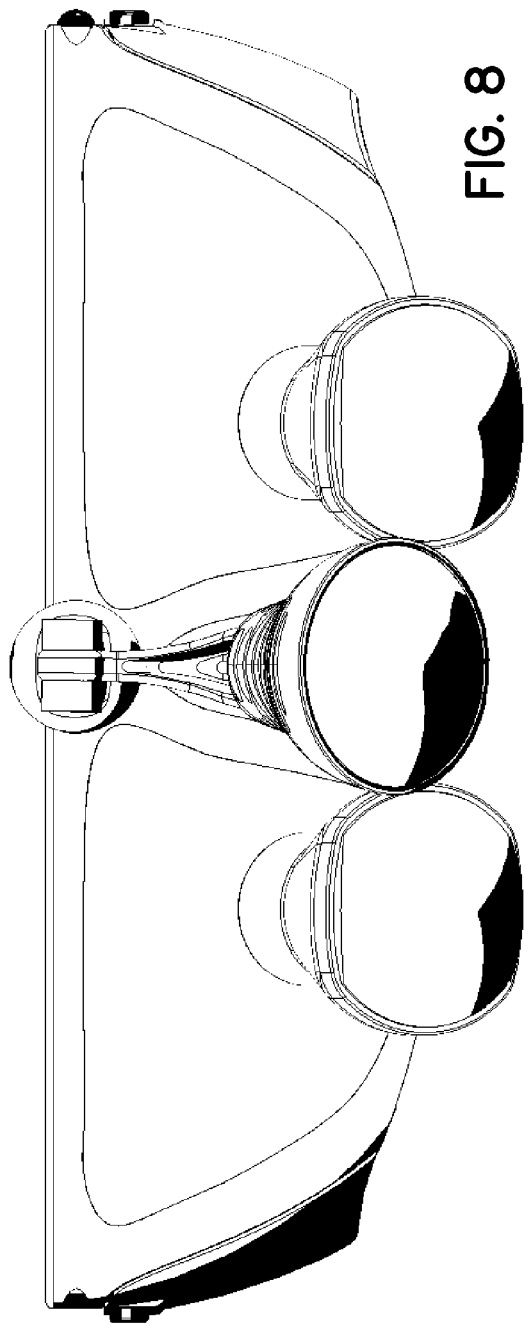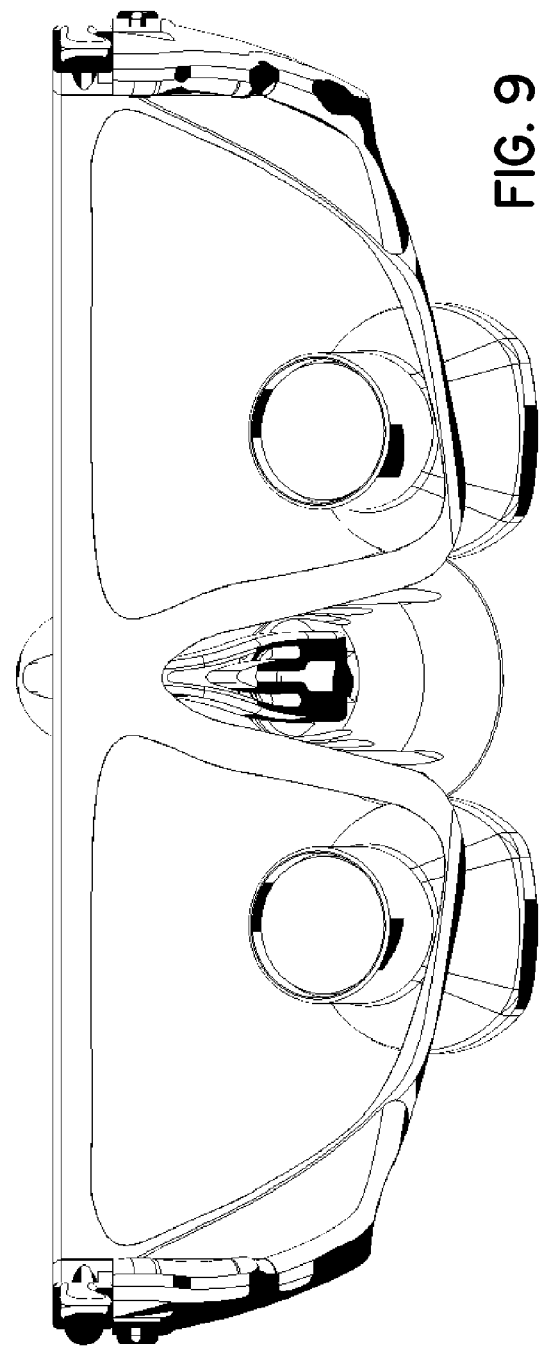

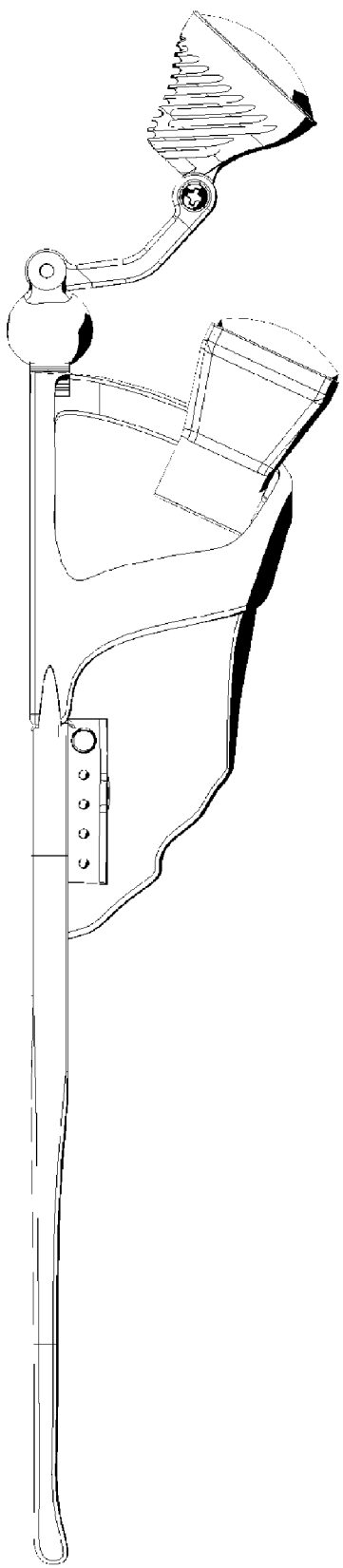
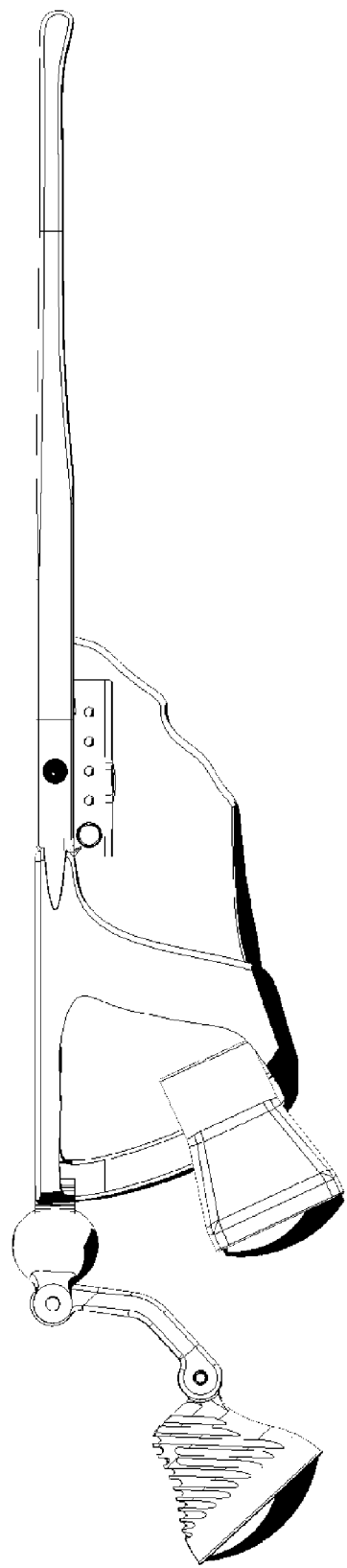

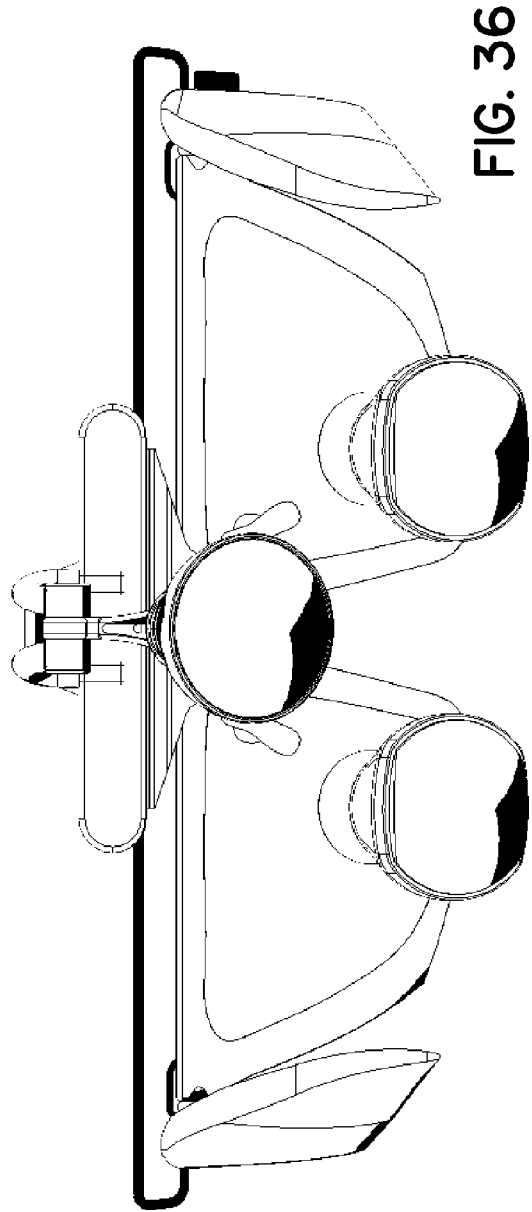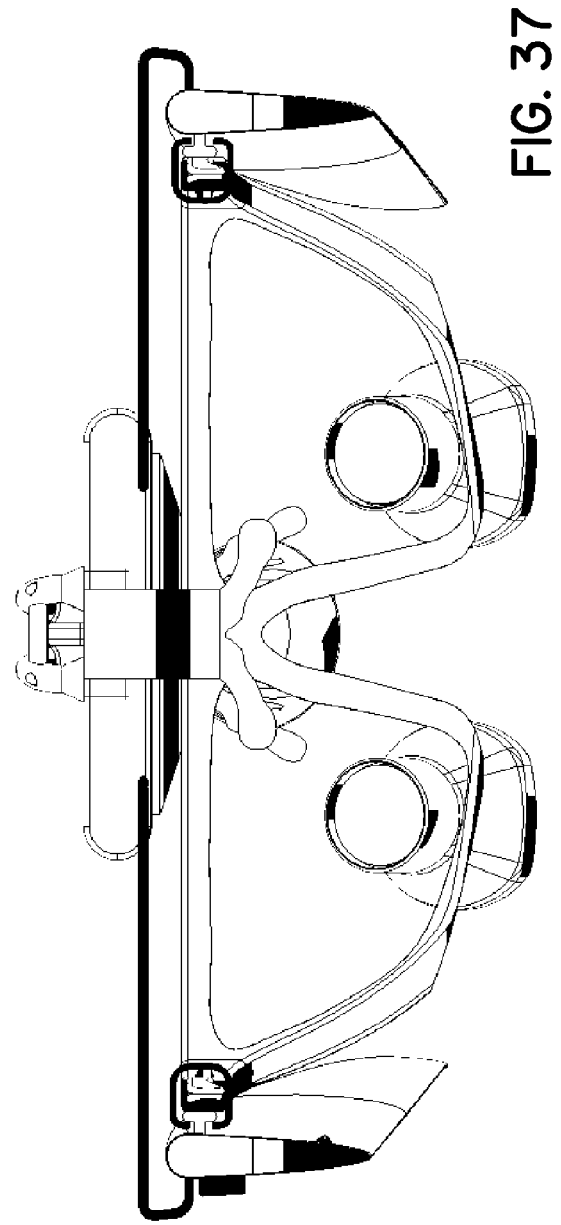

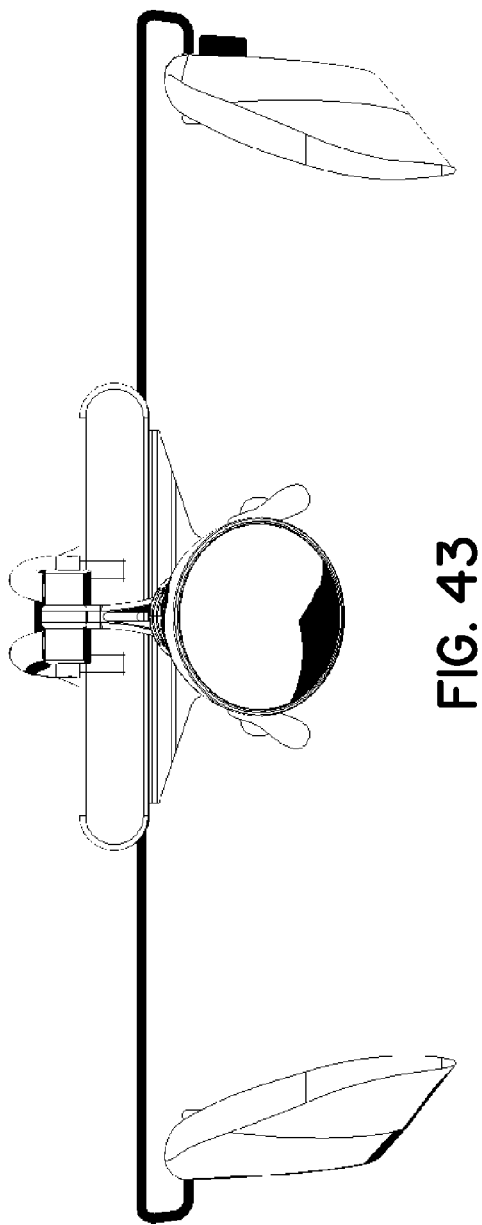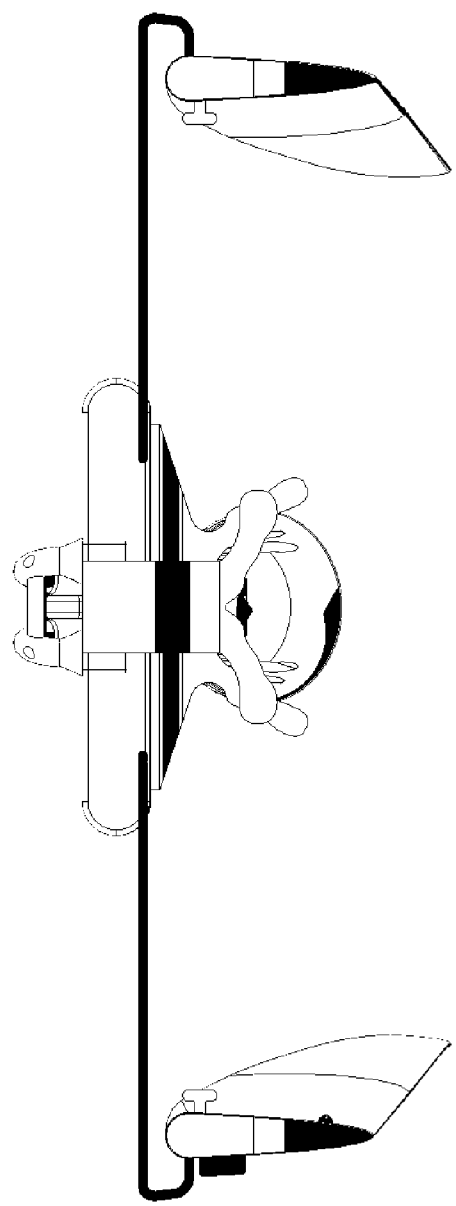

USER-WEARABLE ILLUMINATION ASSEMBLY

CROSS-REFERENCE

This application is a divisional of U.S. patent application Ser. No. 13/314,329 filed Dec. 8, 2011 (pending), which is a continuation-in-part of International Application No. PCT/US2010/037743, filed Jun. 8, 2010 (expired), which claims priority to U.S. Provisional Patent Application Ser. No. 61/185,454 filed on Jun. 9, 2009 and U.S. Provisional Patent Application Ser. No. 61/298,346 filed on Feb. 8, 2010, the disclosures of which are incorporated by reference herein in their entirety.

TECHNICAL FIELD

The present invention relates generally to medical and dental devices, and more particularly to a user-wearable illumination device for medical and dental purposes.

BACKGROUND

User-wearable illumination devices are known for providing illumination to assist practitioners during the performance of various medical and/or dental procedures. In many applications, such illumination devices may be used in combination with optical loupes for providing magnified viewing during the performance of the medical and/or dental procedures.

SUMMARY

While the invention will be described in connection with certain embodiments, it will be understood that the invention is not limited to these embodiments. On the contrary, the invention includes all alternatives, modifications and equivalents as may be included within the spirit and scope of the present invention.

According to one aspect, a user-wearable illumination assembly includes eyeglass frames supporting a pair of lenses and a headlamp removably coupled to the eyeglass frames. The eyeglass frames further include electrical circuitry integrated therewith. The headlamp comprises a housing having mounting structure that cooperates with mounting structure on the eyeglass frames for removably supporting the headlamp thereon. A light source is disposed within the housing and electrical communication between the light source and the electrical circuitry of the eyeglass frames is provided by electrical contacts associated with the mounting structures of the headlamp and the eyeglass frames. In one embodiment, the light source comprises one or more light emitting diodes.

In another aspect, the user-wearable illumination assembly further includes a battery removably coupled to the eyeglass frames and electrically coupled to the electrical circuitry to provide power to the light source. In one embodiment, the battery forms at least a part of a side shield of the eyeglass frames when coupled thereto. In another embodiment, one or more batteries may be supported proximate terminal ends of the temple arms of the eyeglass frames. The batteries may be pivotally coupled to the terminal ends of the temple arms, for engaging the head of a user. In yet another embodiment, the battery may be supported on a strap coupled to the terminal ends of the temple arms. The battery may be rechargeable, and may include an indicator for indicating the charge level of the battery.

In another aspect, the user-wearable illumination assembly may further include at least one optical loupe coupled to the eyeglass frames for providing magnified viewing through the loupe. The above and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention and, together with a general description of the invention given above, and the detailed description given below, serve to explain the principles of the invention.

FIG. 8 is a front elevation view thereof;
FIG. 9 is a rear elevation view thereof;
FIG. 10 is a left-side elevation view thereof;
FIG. 11 is a right-side elevation view thereof.

FIG. 33A is an enlarged detail view of a clip assembly and headlamp of the illumination assembly of FIG. 33.

FIG. 36 is a front elevation view thereof;

FIG. 37 is a rear elevation view thereof;

FIG. 43 is a front elevation view thereof;

FIG. 44 is a rear elevation view thereof;

DETAILED DESCRIPTION

Figure 1:
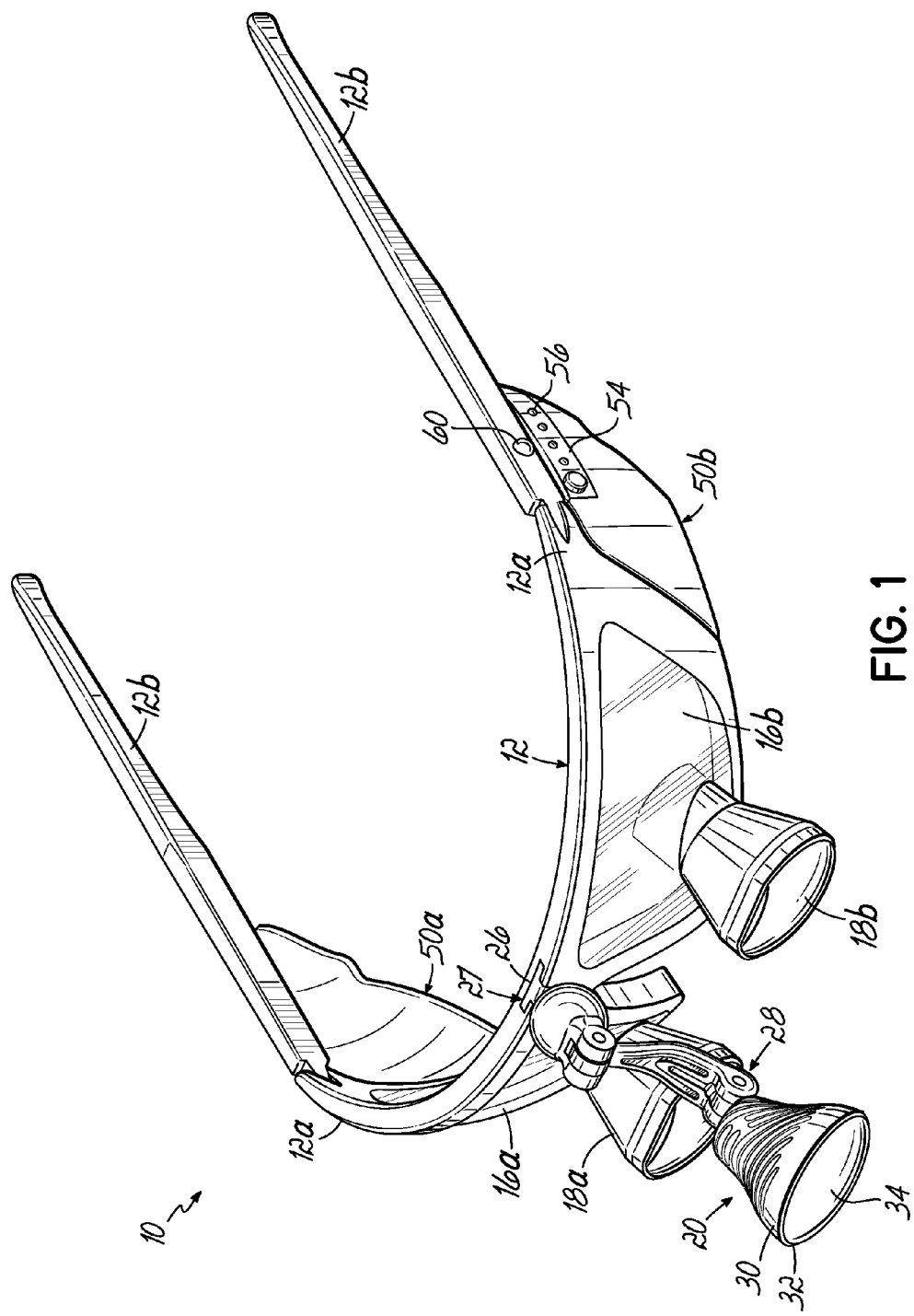
FIG. 1 is a perspective view of an exemplary user-wearable illumination assembly in accordance with the present disclosure.
Figure 2:
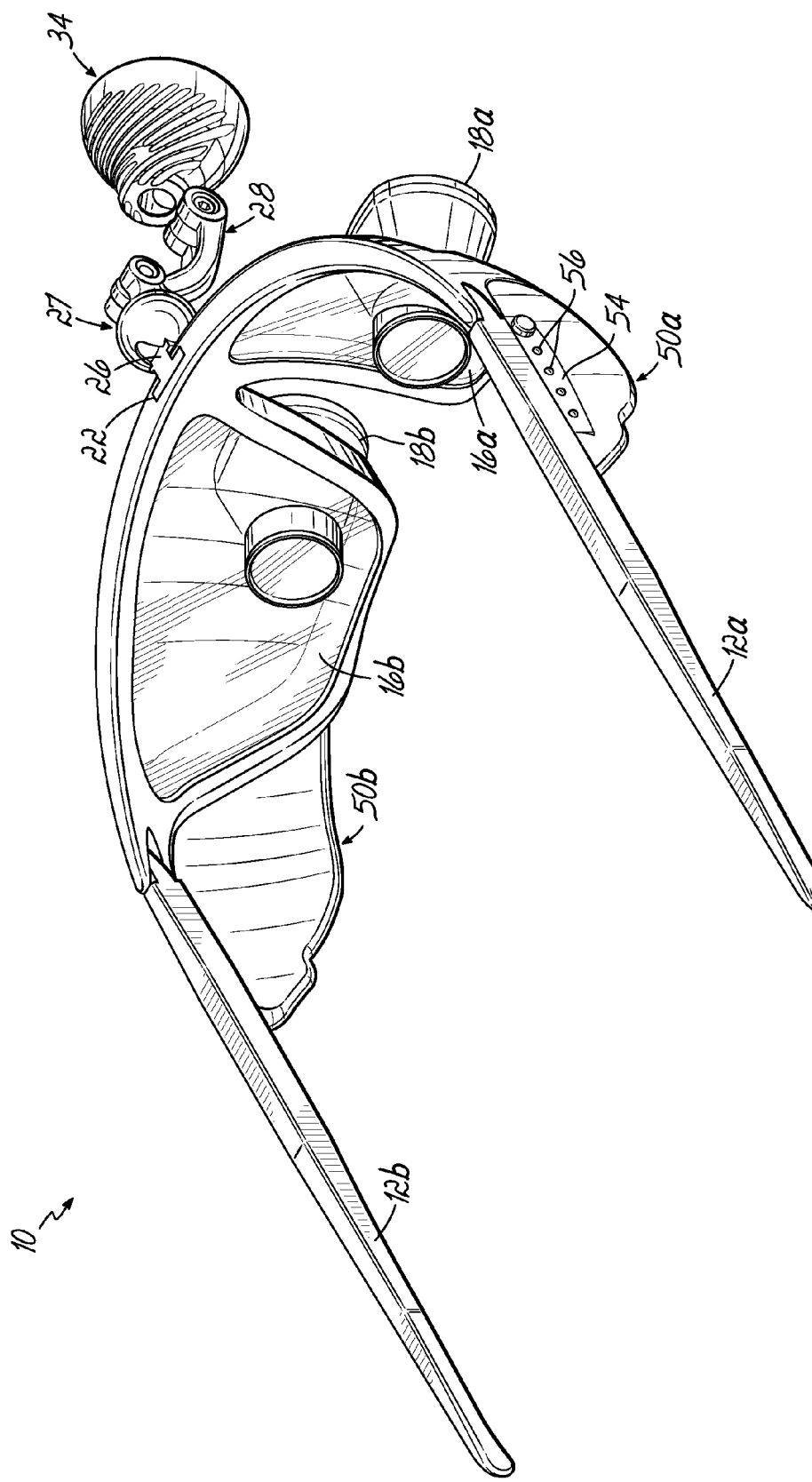
FIG. 2 is a perspective view of the user-wearable illumination assembly of FIG. 1, viewed from another direction.
Figure 3:
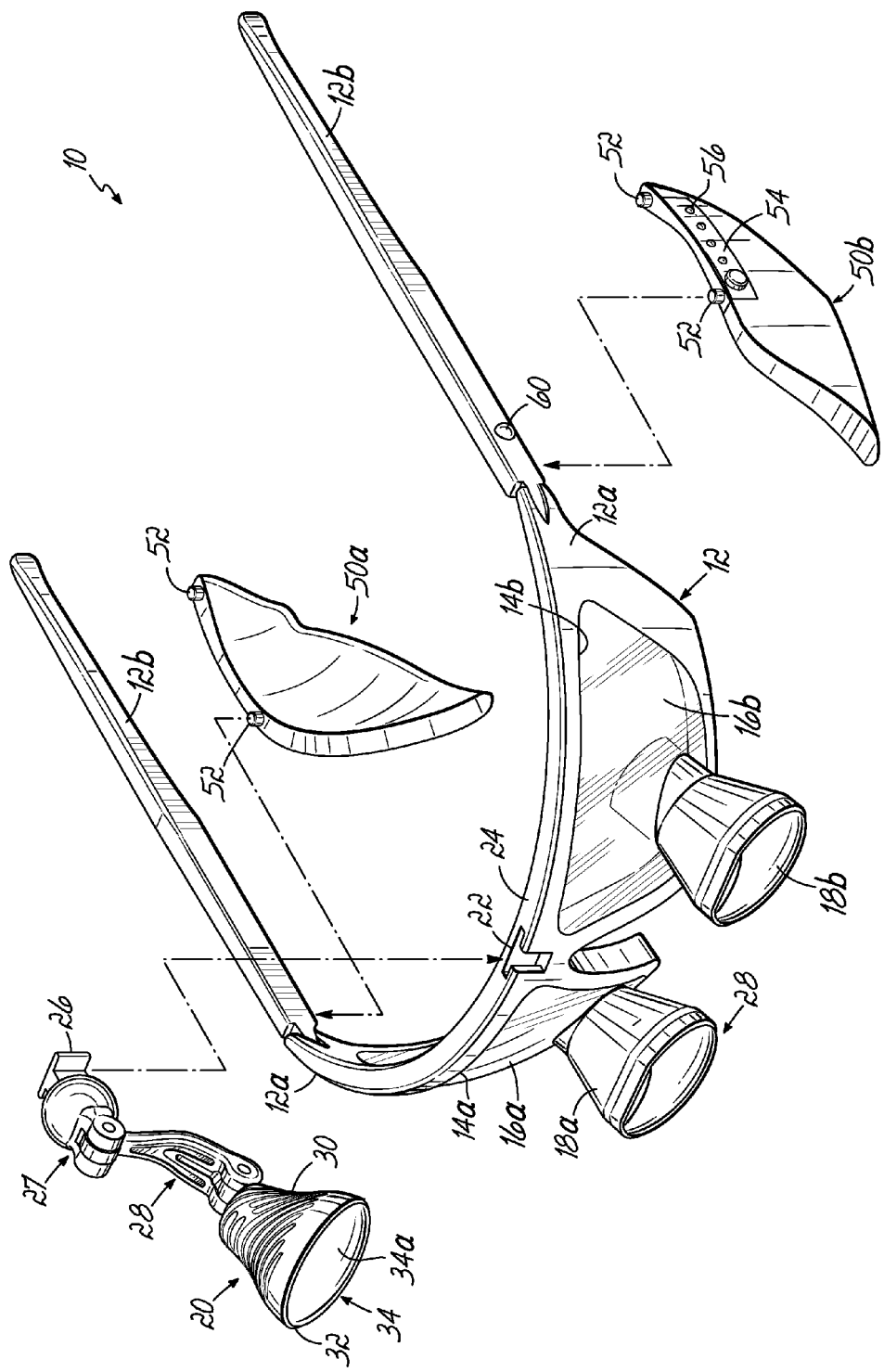
FIG. 3 is an exploded perspective view of the user-wearable illumination assembly of FIG. 1.
Figure 4:
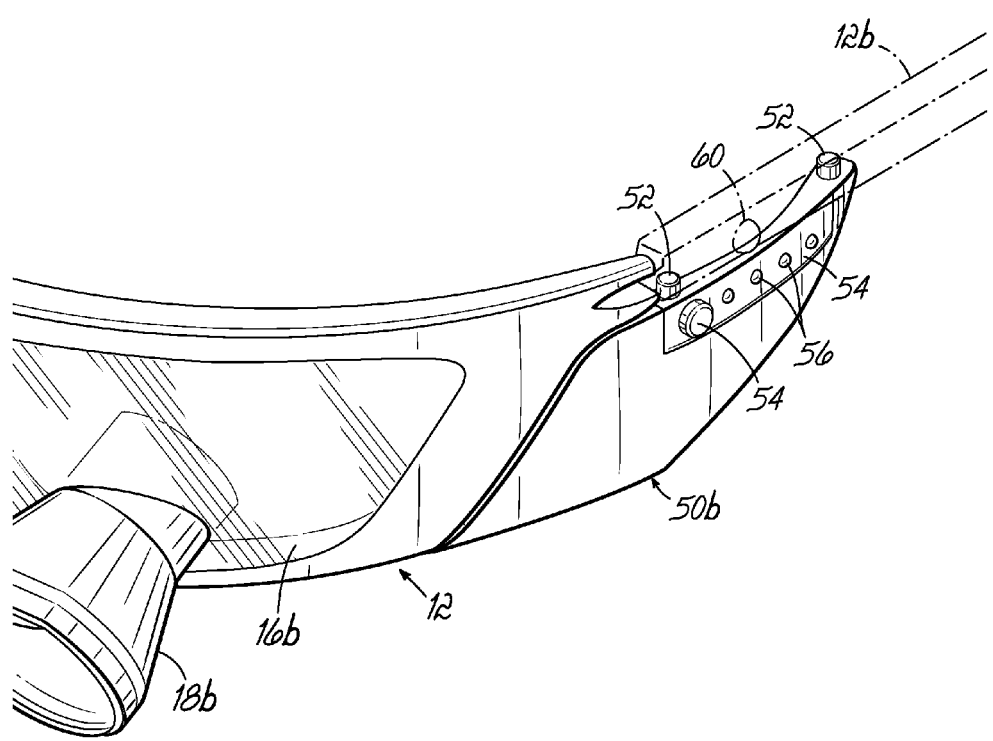
FIG. 4 is an enlarged detail view of the battery portion of the user-wearable illumination assembly of FIG. 1.
Figure 5:
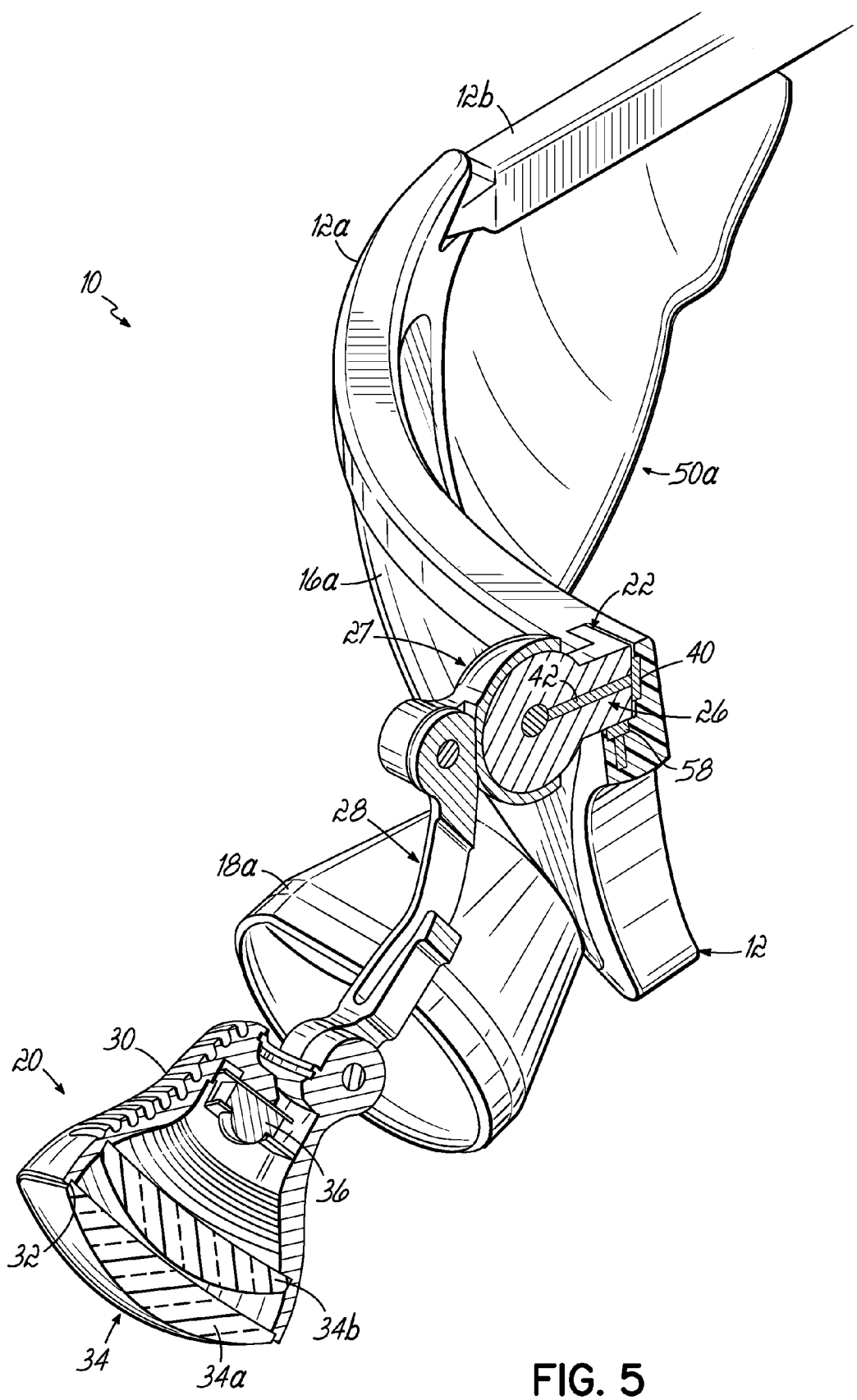
FIG. 5 is a partial cross-sectional view of the headlamp portion of the user-wearable illumination assembly of FIG. 1.
Figure 6:
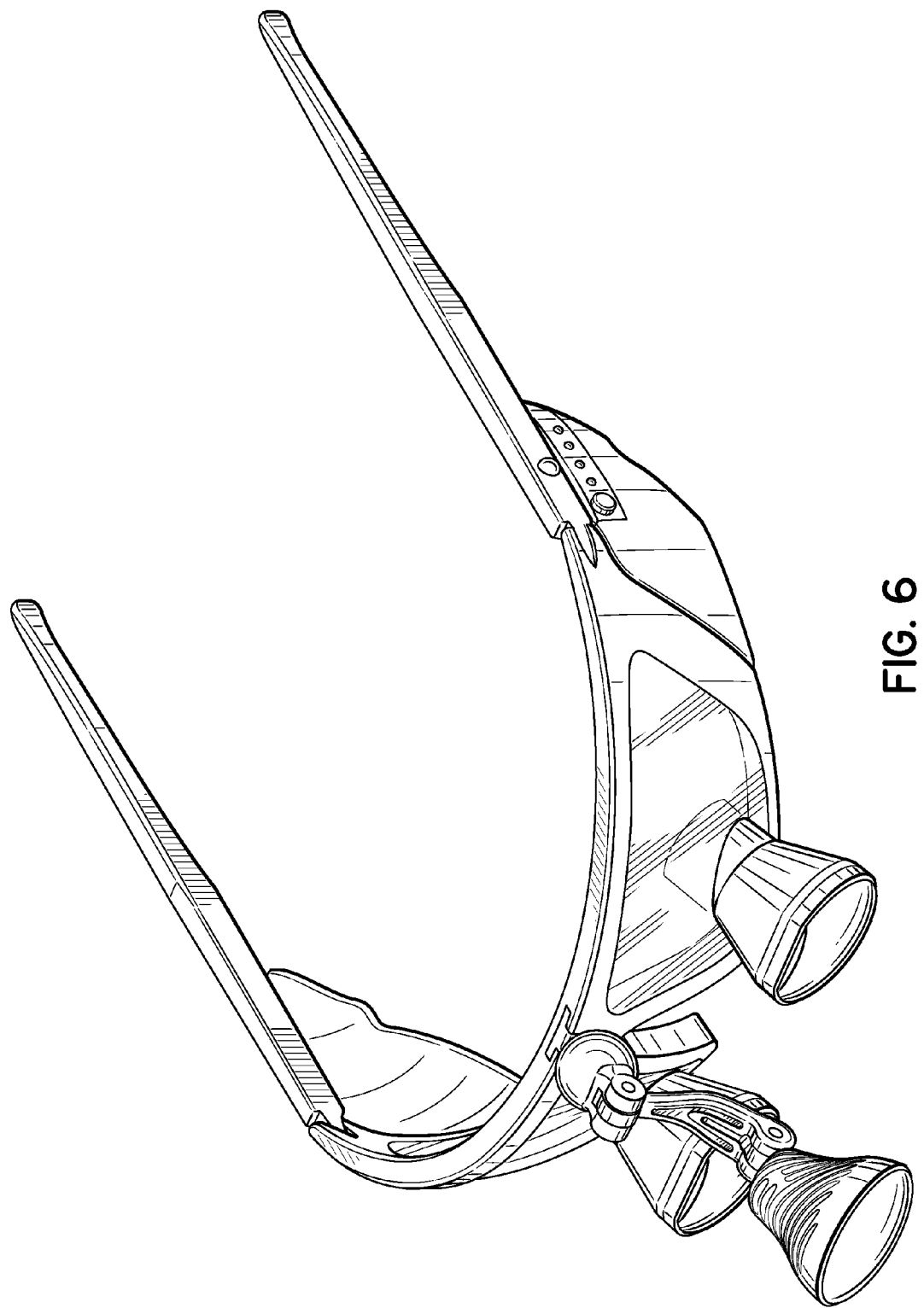
FIG. 6 is another perspective view of the user-wearable illumination assembly of FIG. 1, illustrating the ornamental design of the exemplary embodiment.
Figure 7:
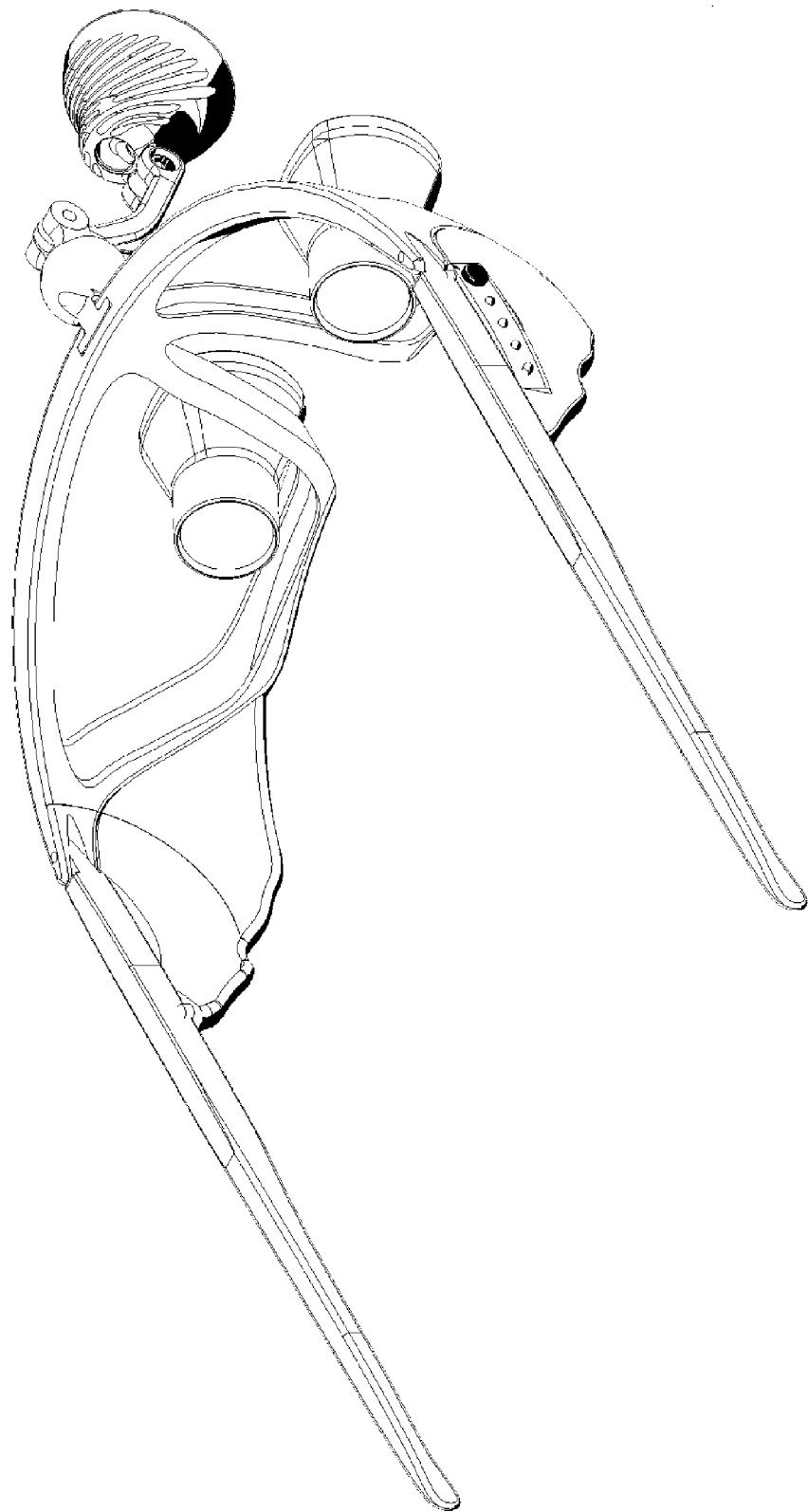
FIG. 7 is another perspective view of the user-wearable illumination assembly of FIG. 1, viewed from another direction.
Figure 12:
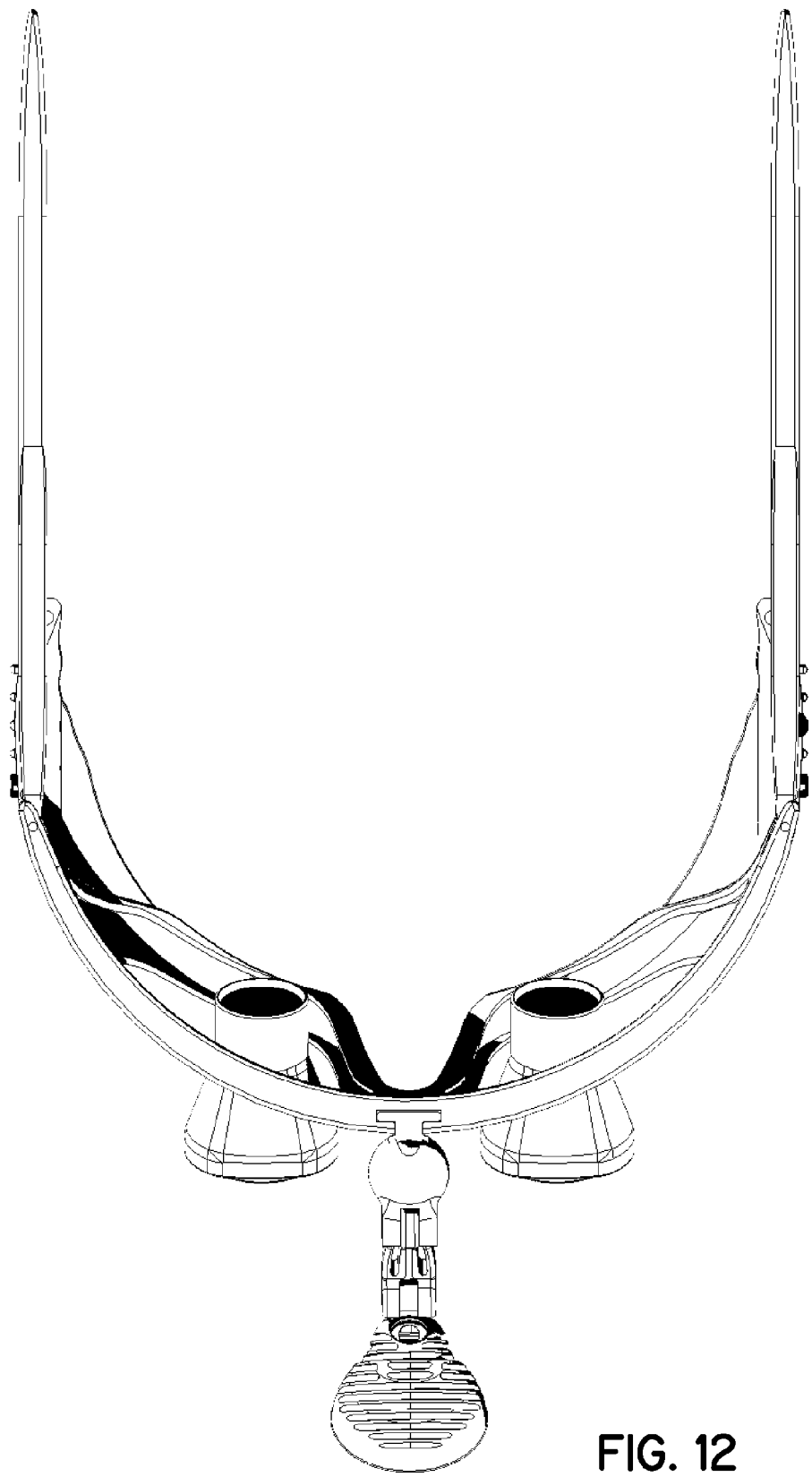
FIG. 12 is a top plan view thereof.
Figure 13:
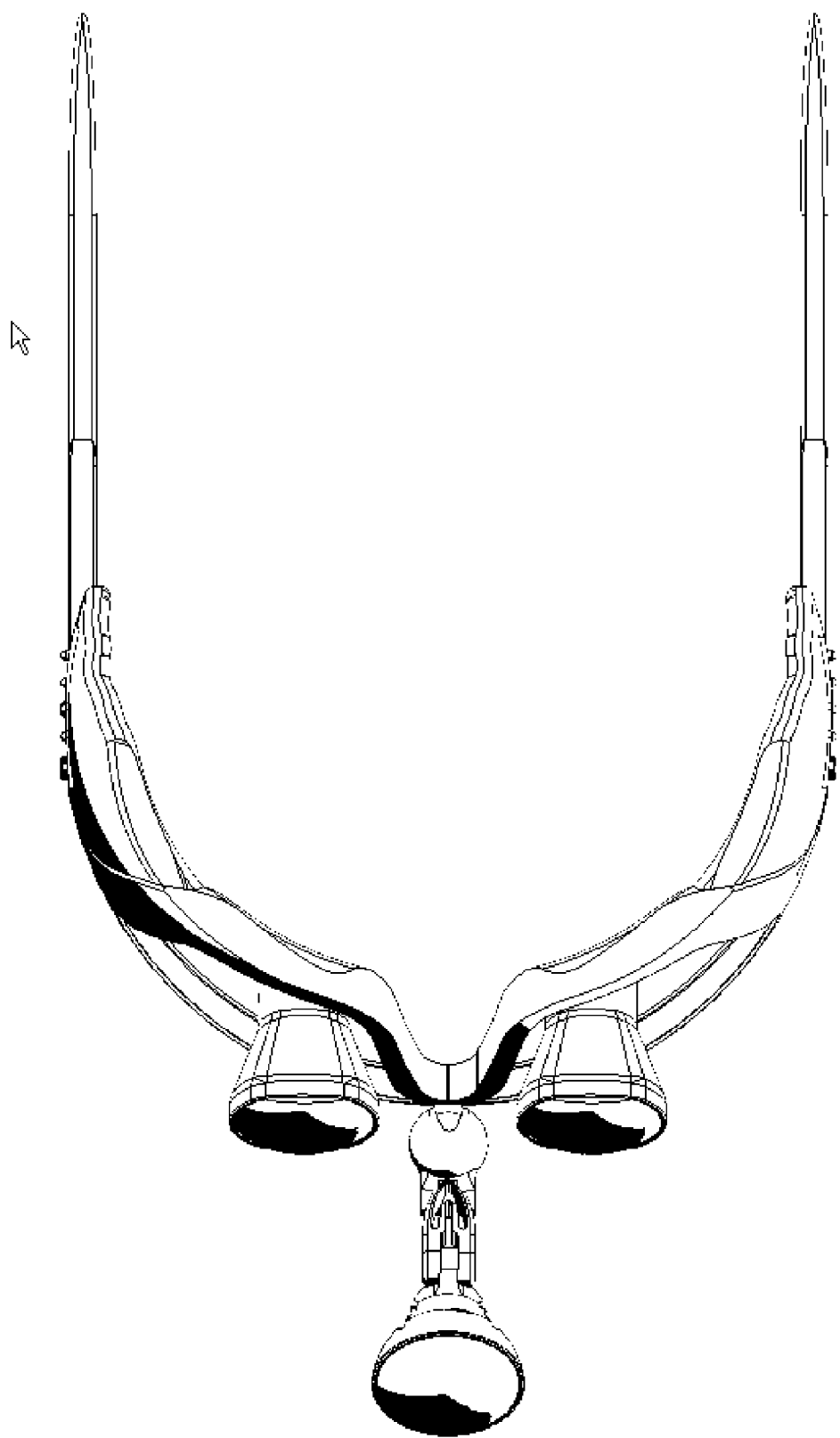
FIG. 13 is a bottom plan view thereof.
Figure 14:
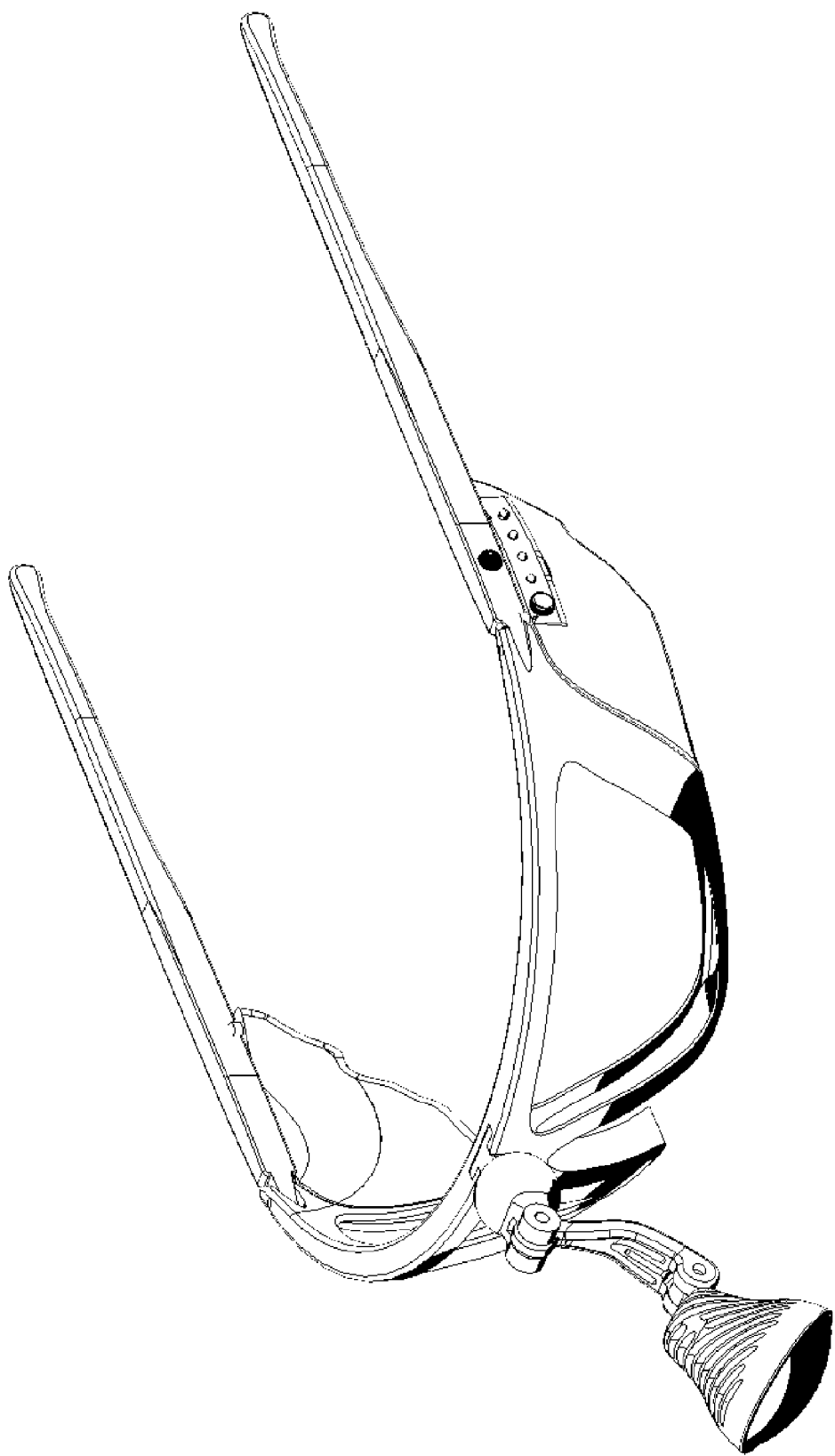
FIG. 14 is a perspective view of another exemplary embodiment of a user-wearable illumination assembly, illustrating the ornamental design of the embodiment.
Figure 15:
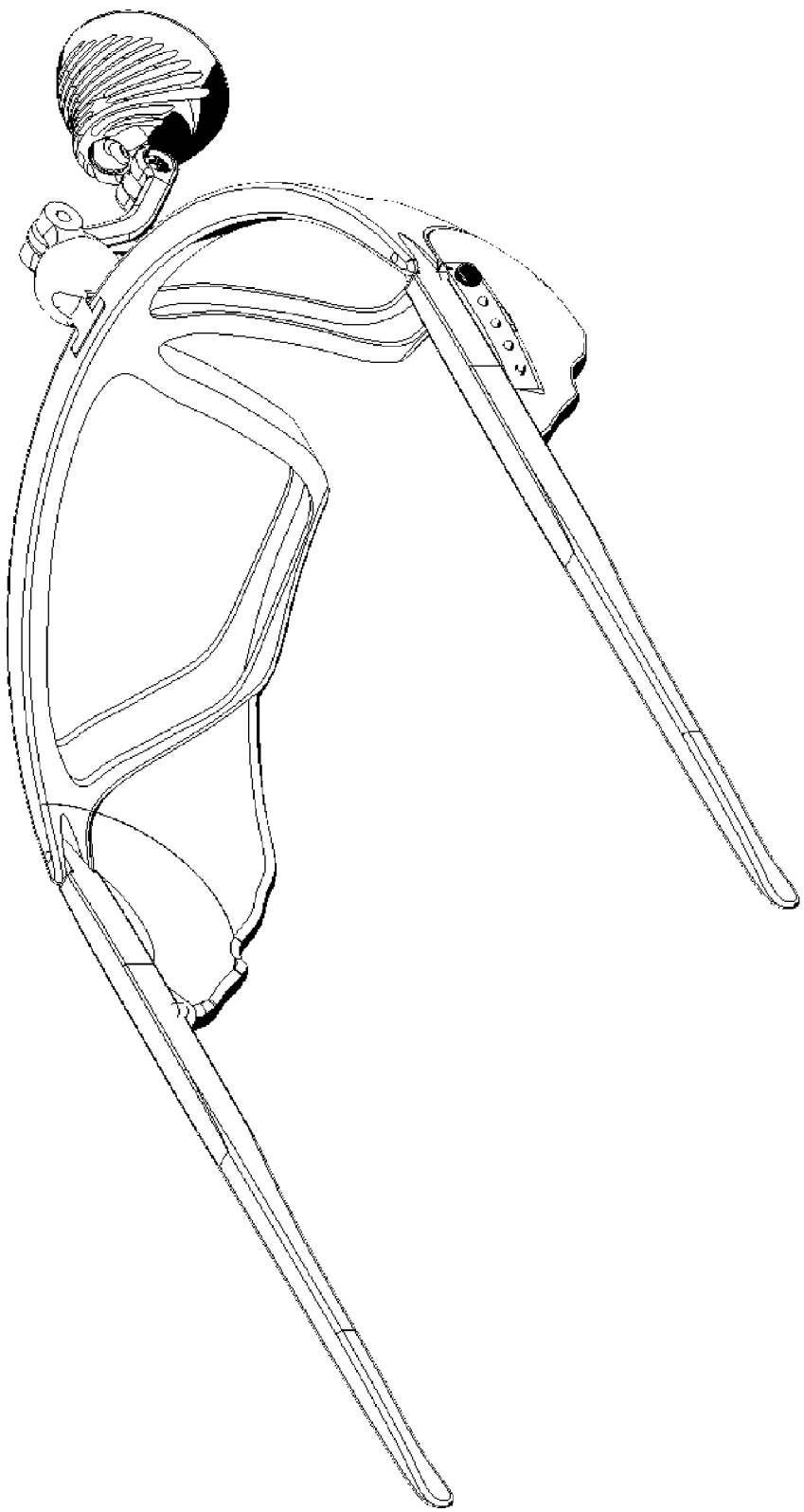
FIG. 15 is another perspective view of the user-wearable illumination assembly of FIG. 14, viewed from another direction.
Figure 16:
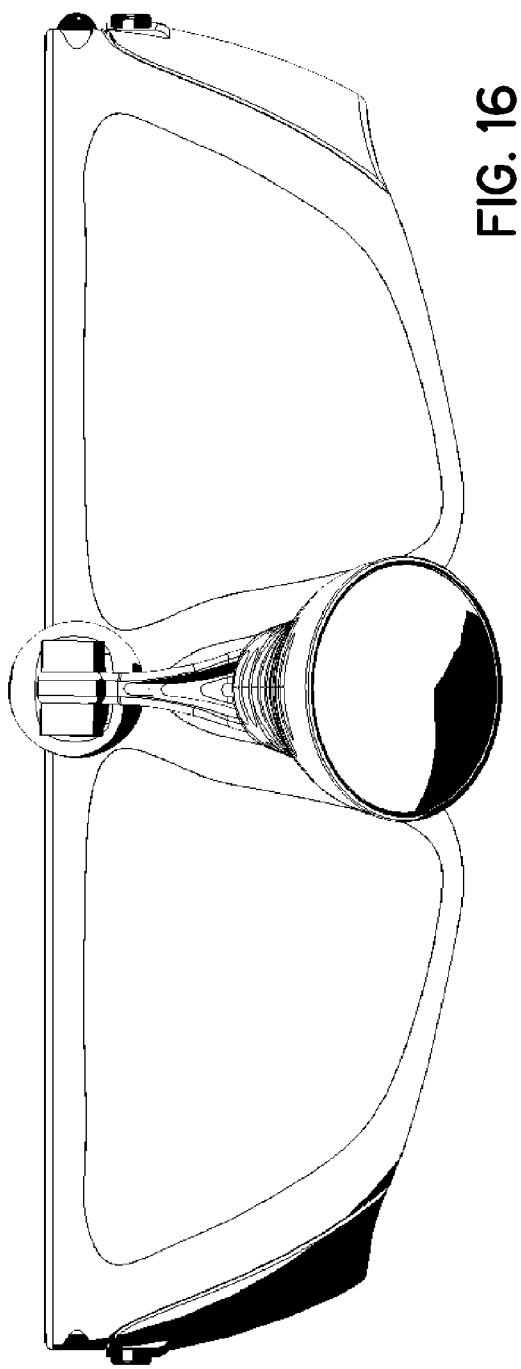
FIG. 16 is a front elevation view thereof.
Figure 17:
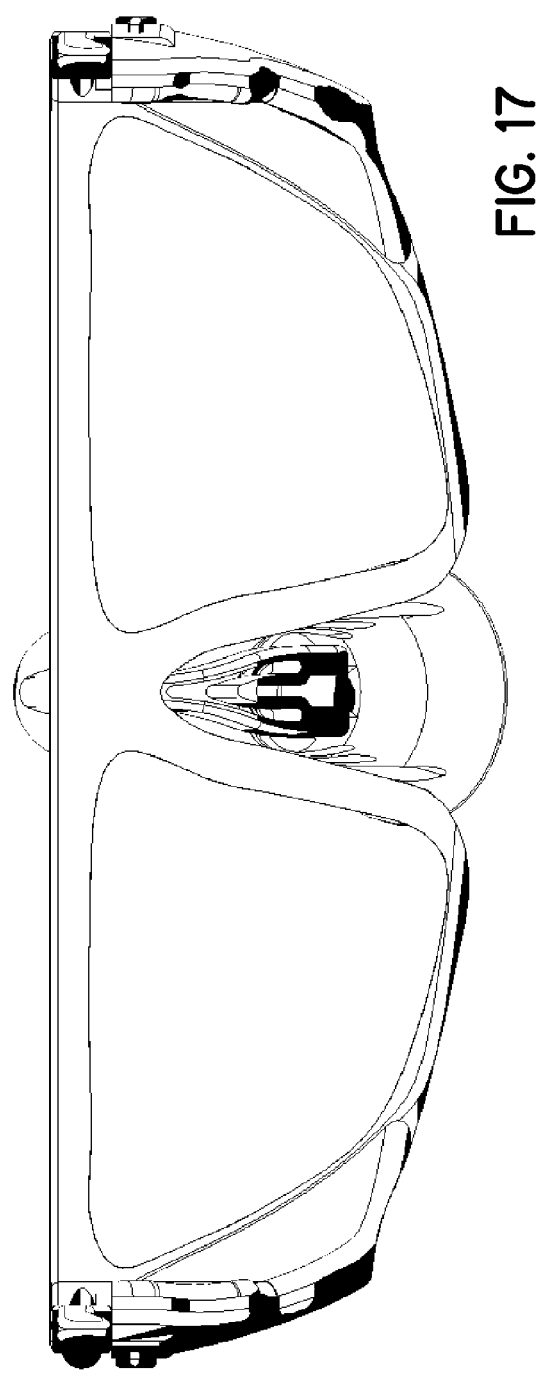
FIG. 17 is a rear elevation view thereof.
Figure 18:
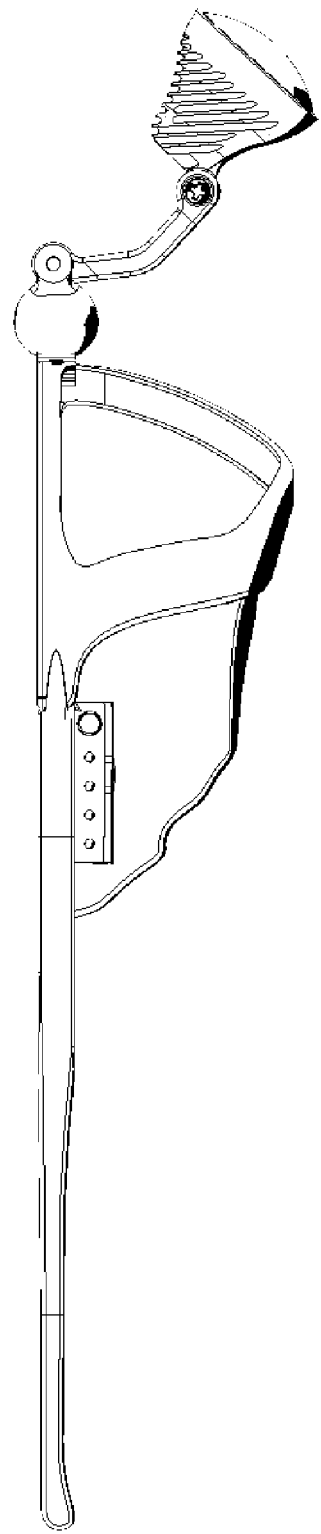
FIG. 18 is a left-side elevation view thereof.
Figure 19:
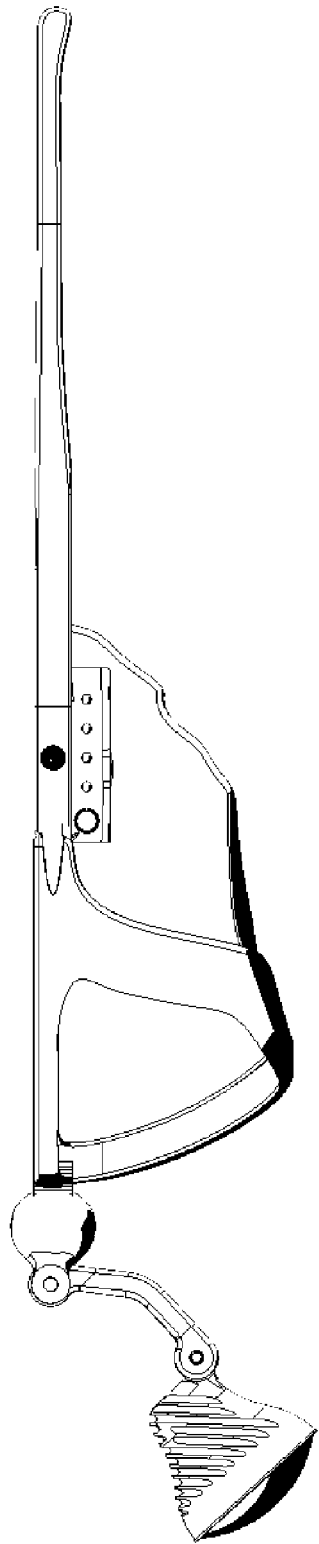
FIG. 19 is a right-side elevation view thereof.
Figure 20:
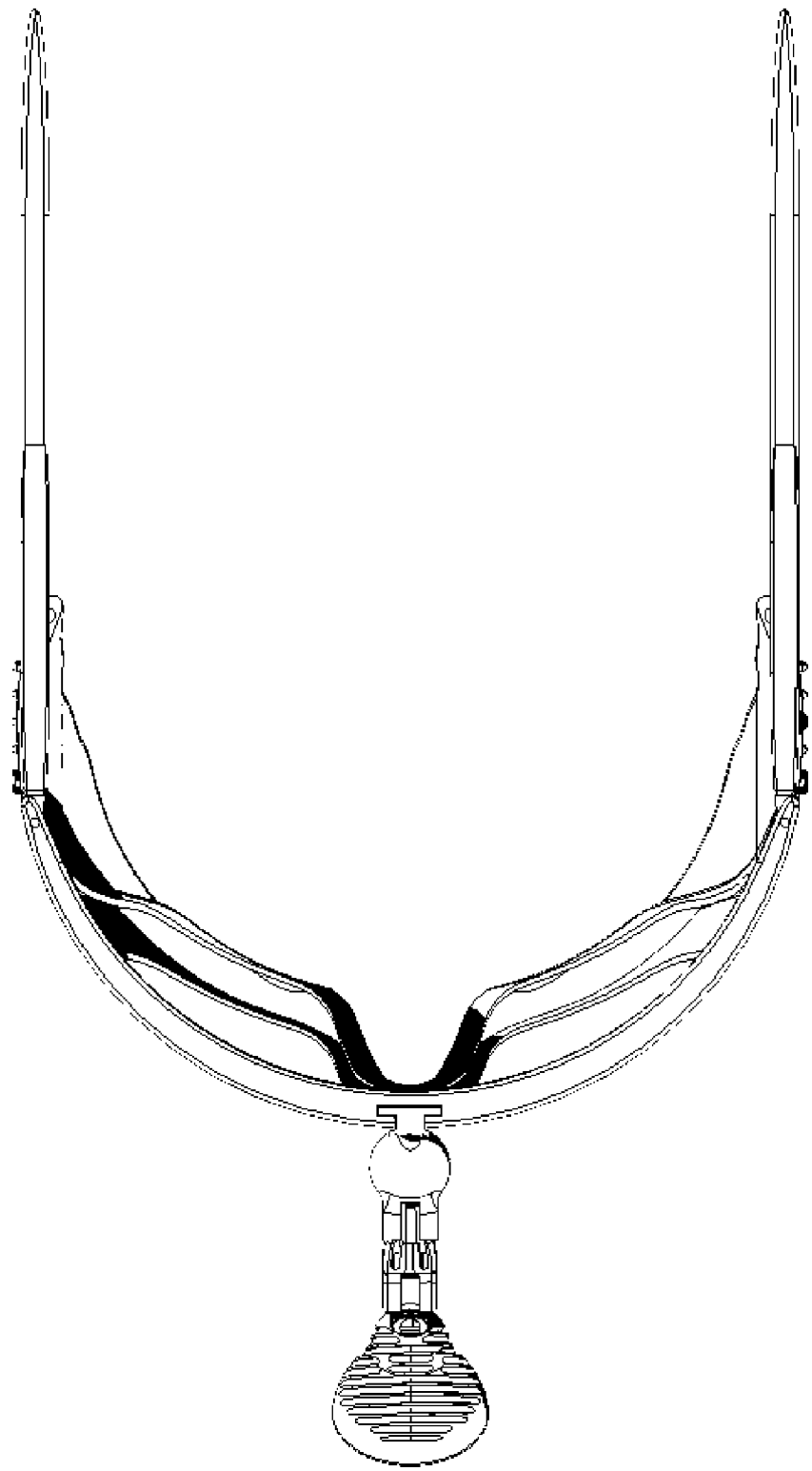
FIG. 20 is a top plan view thereof.
Figure 21:
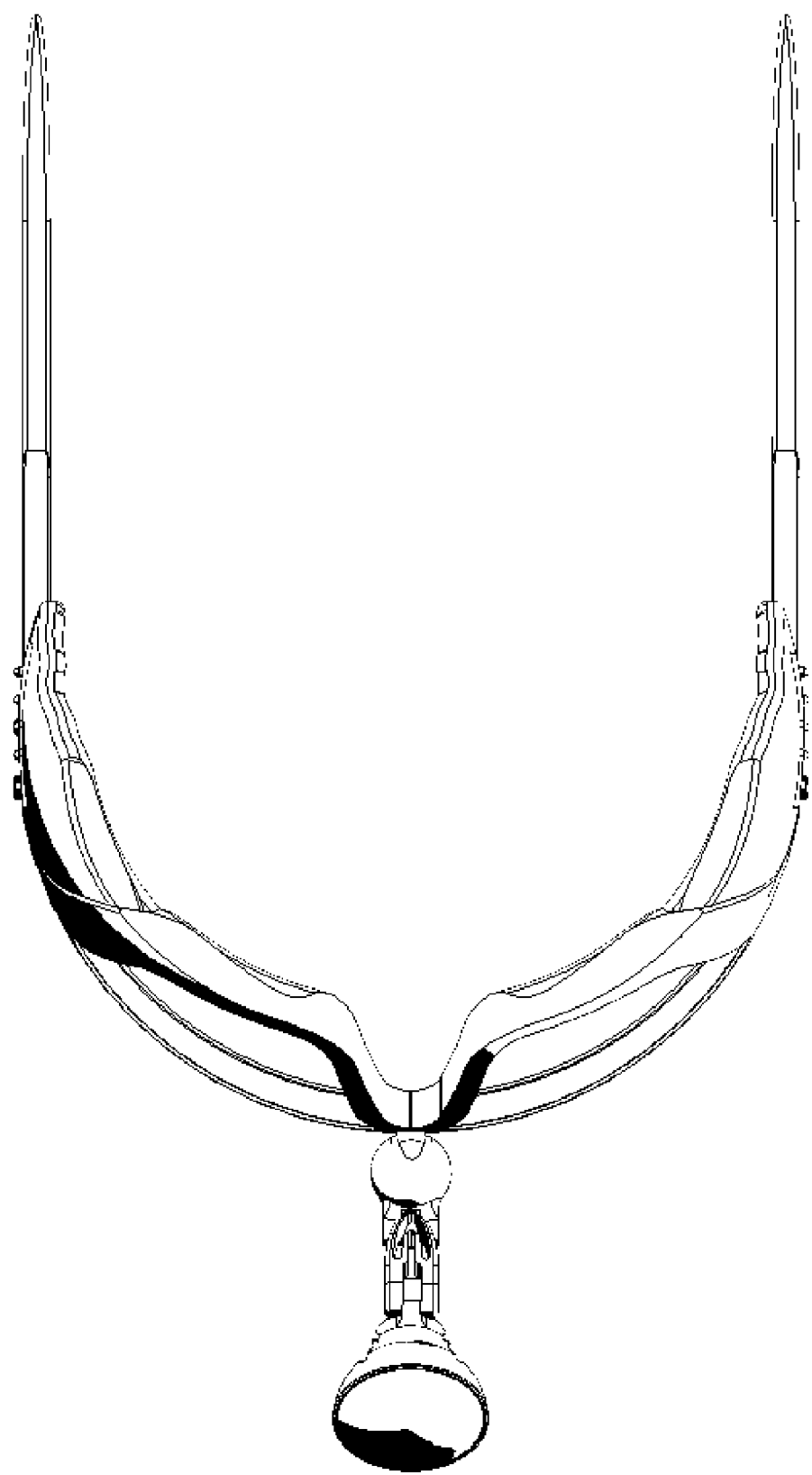
FIG. 21 is a bottom plan view thereof.
Figure 22:
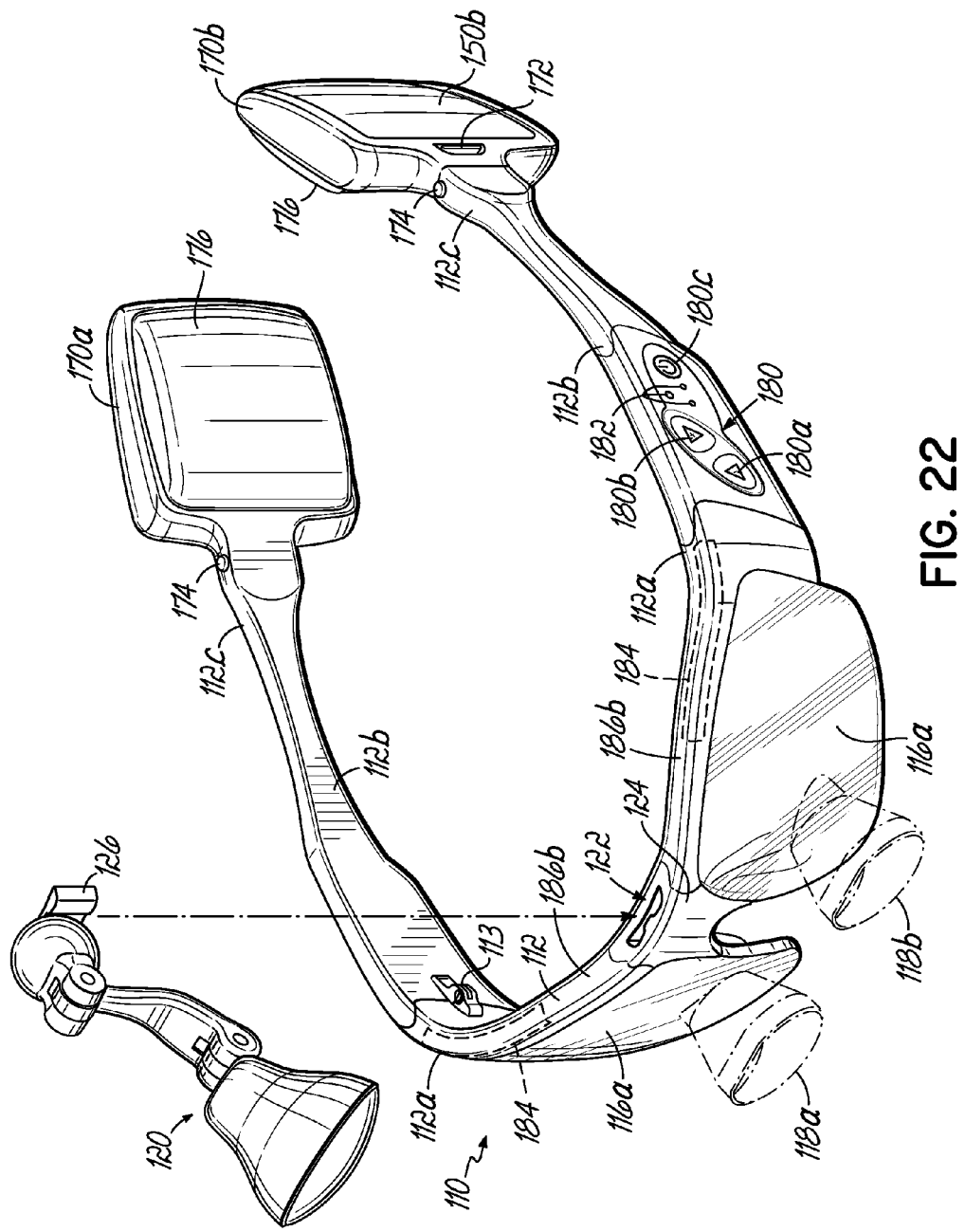
FIG. 22 is an exploded perspective view of another exemplary user-wearable illumination assembly in accordance with the present disclosure.
Figure 22A:
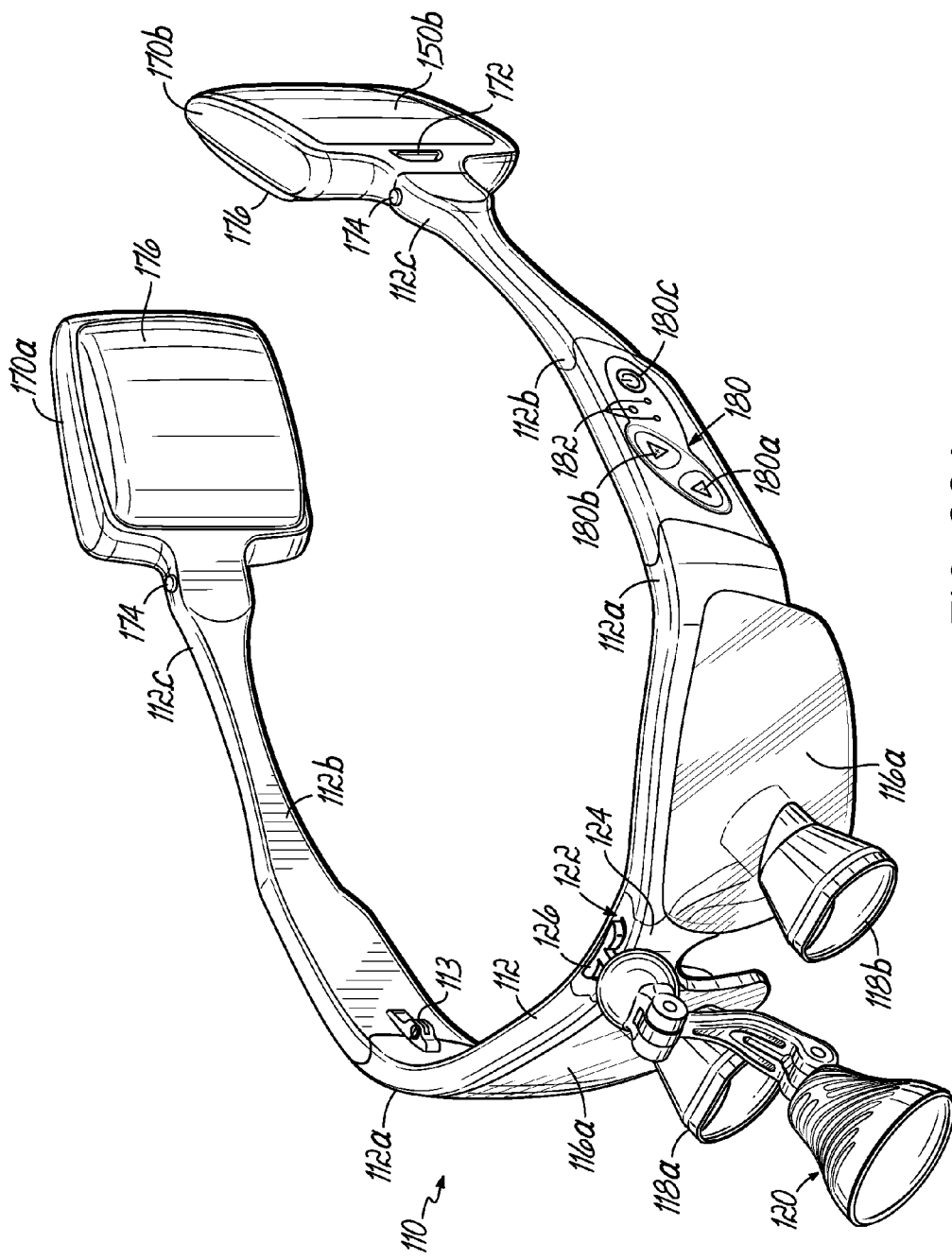
FIG. 22A is another perspective view of the user-wearable illumination assembly if FIG. 22.
Figure 23:
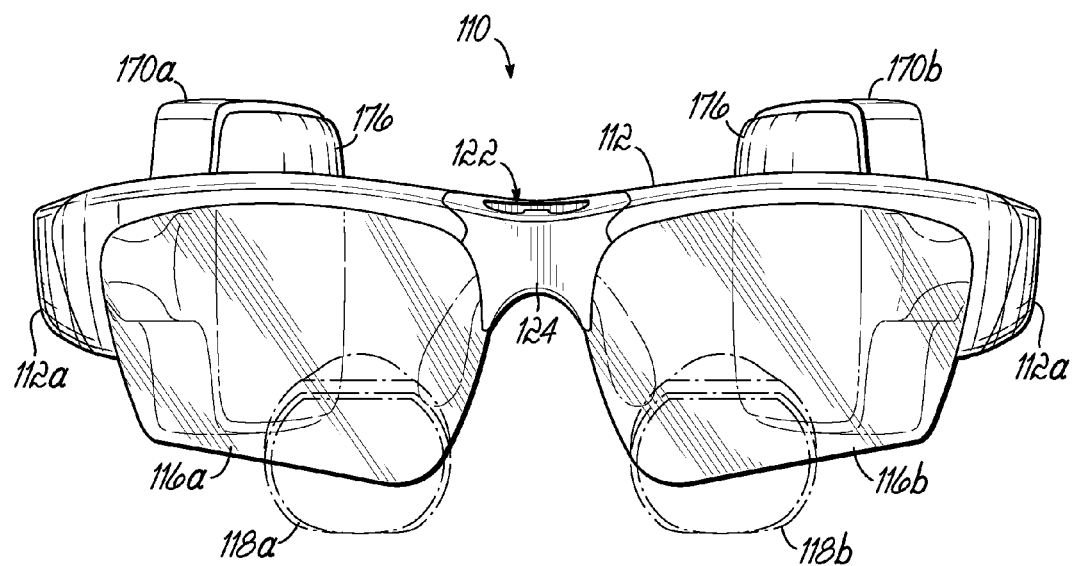
FIG. 23 is a front elevation view of the user-wearable illumination assembly if FIG. 22.
Figure 24:
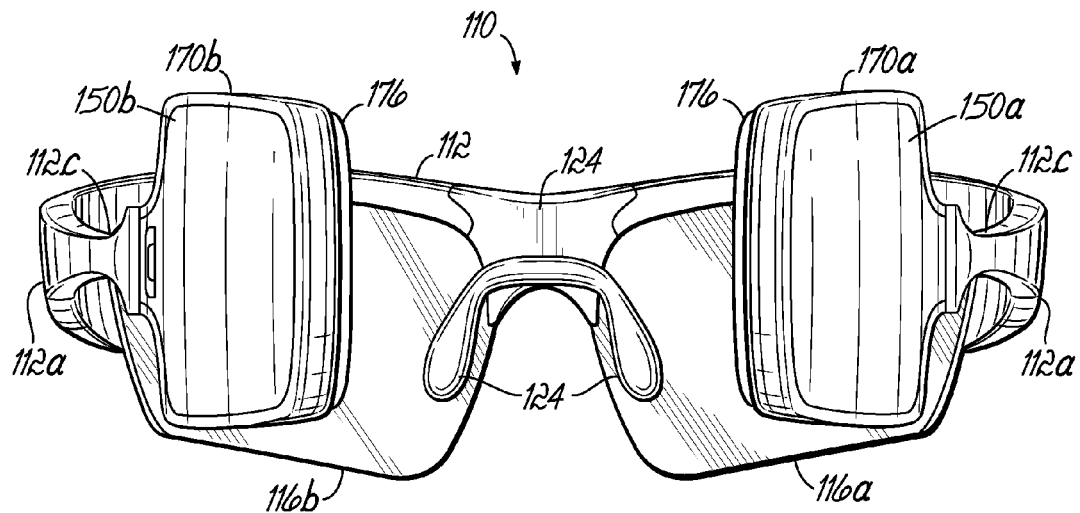
FIG. 24 is a rear elevation view of the user-wearable illumination assembly if FIG. 22.
Figure 25:
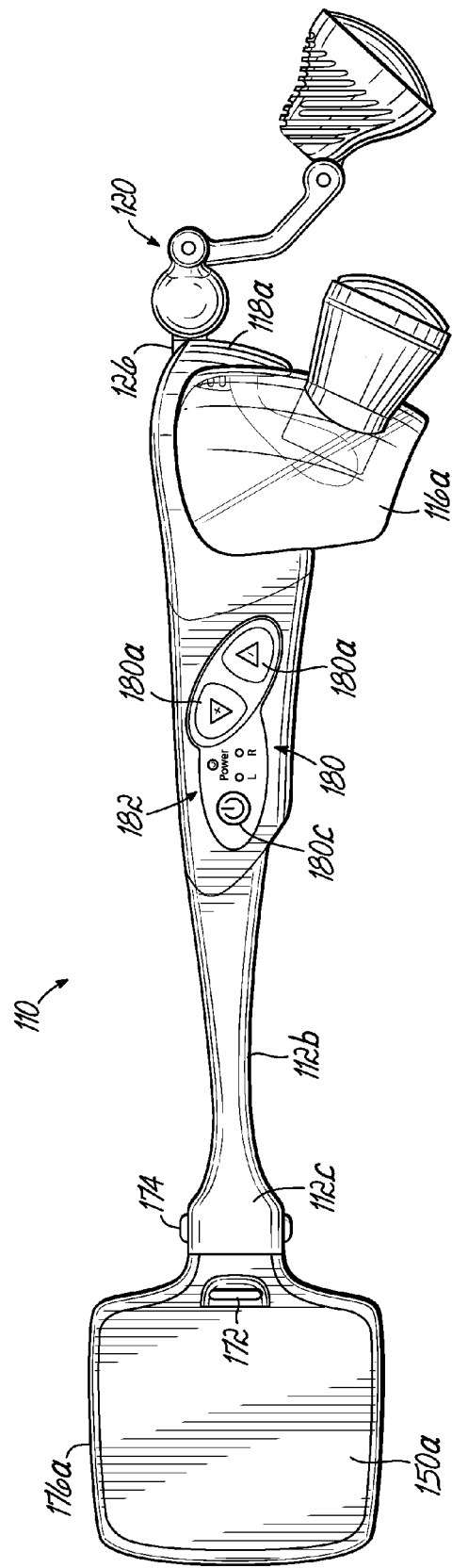
FIG. 25 is a right-side elevation view of the user-wearable illumination assembly if FIG. 22.
Figure 25A:
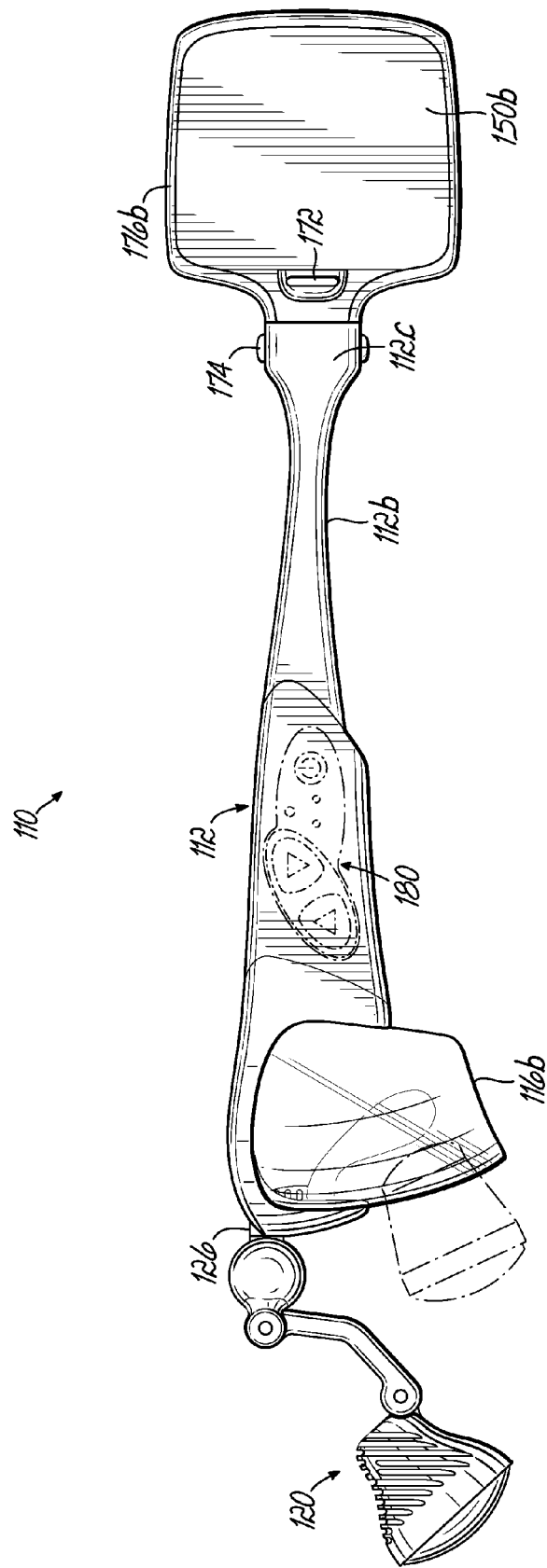
FIG. 25A is a left-side elevation view of the user-wearable illumination assembly if FIG. 22.
Figure 26:
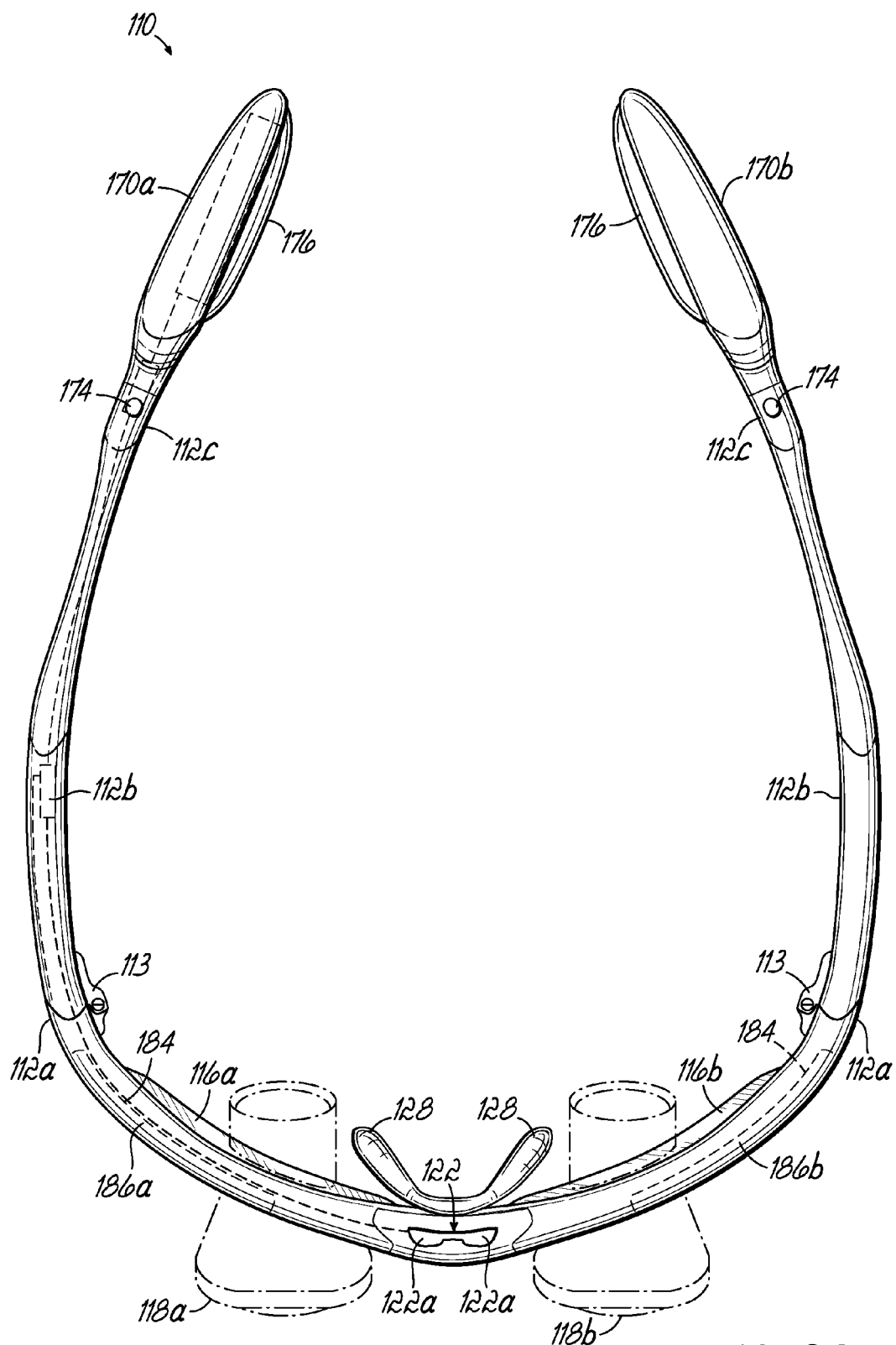
FIG. 26 is a top plan view of the user-wearable illumination assembly if FIG. 22.
Figure 26A:
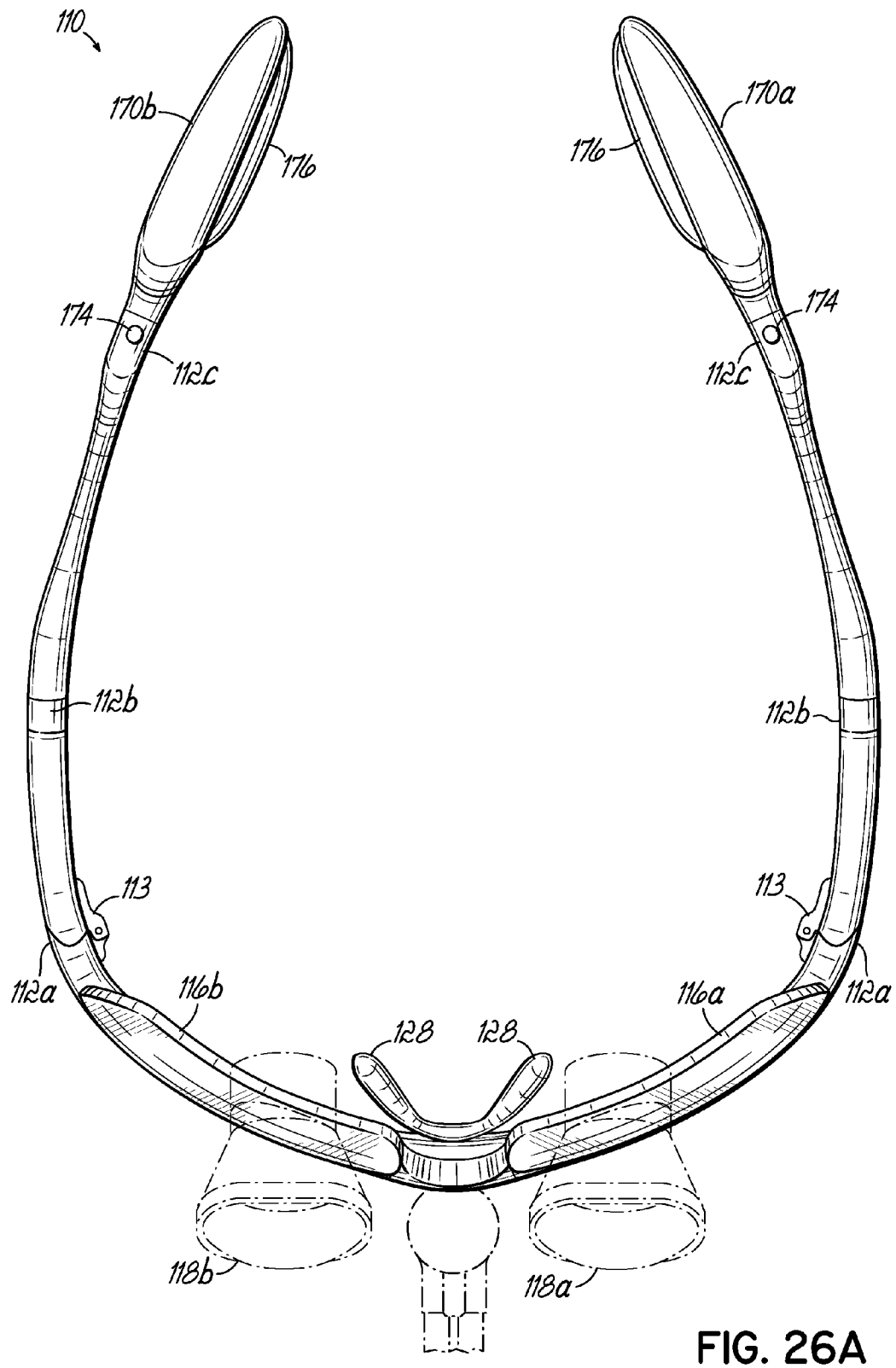
FIG. 26A is a bottom plan view of the user-wearable illumination assembly if FIG. 22.
Figure 27:
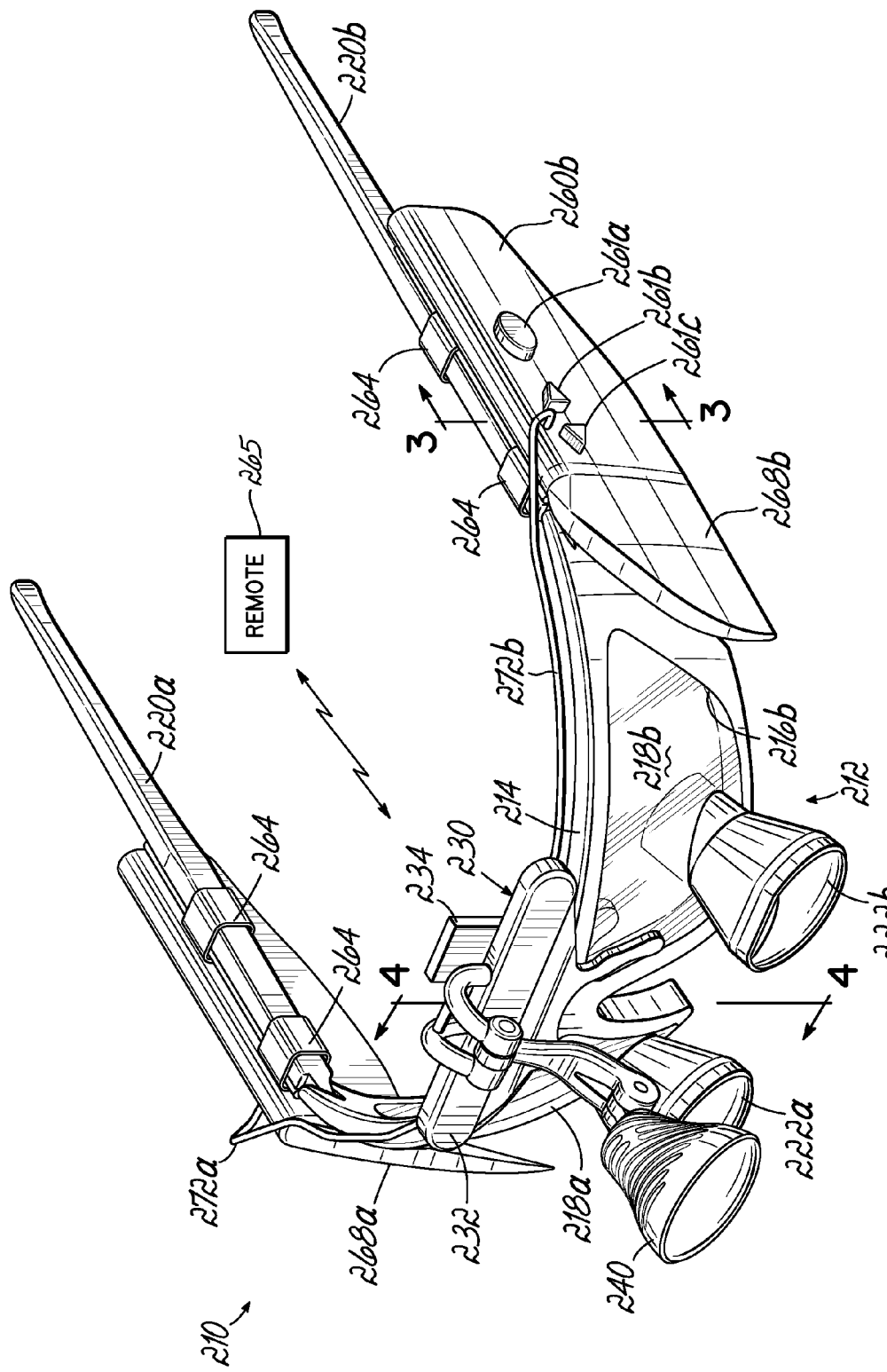
FIG. 27 is a perspective view of another exemplary user-wearable illumination assembly for use with eyeglass frames in accordance with the present disclosure.

FIGS. 1-5 depict an exemplary user-wearable illumination assembly 10 in accordance with the present disclosure. The illumination assembly 10 comprises eyeglass frames 12 adapted to be worn by a user and defining a pair of apertures 14a, 14b for supporting lenses 16a, 16b on the eyeglass frames 12. In the embodiment shown, individual lenses 16a, 16b are carried by each aperture 14a, 14b of the eyeglass frames 12. It will be appreciated, however, that a single lens may alternatively be carried by the eyeglass frames 12, with the single lens extending between both apertures 14a, 14b. In this embodiment, the illumination assembly 10 further includes a pair of magnification loupes 18a, 18b. The loupes 18a, 18b shown are supported through the respective lenses 16a, 16b and are therefore permanently supported on the illumination assembly 10. It will be appreciated, however, that optical loupes 18a, 18b may alternatively be provided on a flip-up style mounting, such as the mounting shown and described in U.S. Patent Application Publication No. 2007/0153498 for example, instead of being mounted through the lenses 16a, 16b as depicted herein. Exemplary optical loupes 18a, 18b for use in the illumination assembly 10 are disclosed in U.S. Pat. No. 7,072,124 to Wilt et al. U.S. Patent Application Publication No. 2007/0153498 and U.S. Pat. No. 7,072,124 are assigned to the assignee of the present invention. It is contemplated that the illumination assembly 10 may alternatively be provided without optical loupes 18a, 18b, or that optical loupes may be removably attached to the eyeglass frames 12, such as by a flip-up style mounting.

The eyeglass frames 12 are configured to receive a headlamp 20 for providing illumination to the wearer of the illumination assembly 10. In the embodiment shown, a first mounting structure 22 is provided on a bridge portion 24 of the eyeglass frames 12. In this embodiment, the mounting structure 22 comprises a T-shaped slot for slidably receiving a corresponding mounting structure 26 on the headlamp 20, whereby the headlamp 20 may be easily attached to the eyeglass frames 12. The corresponding mounting structure 26 provided on the headlamp 20 of this embodiment has a shape that is complementary to the T-shaped slot formed in the eyeglass frames 12. In the embodiment shown, mounting structure 26 further includes a multi-directional ball-andsocket-joint 27 and a pivot arm 28 to facilitate positioning and orienting the headlamp 20 as may be desired. It will be appreciated, however, that various other mounting structure suitable for removably coupling the headlamp 20 to the frames 12 may alternatively be provided, and the mounting structure 22, 26 is not limited to that shown and described herein.

The headlamp 20 further comprises a housing 30 having an open end 32 for supporting a lens 34 thereon. A light source 36 is supported within the housing 30 and generally behind the lens 34. In this embodiment, lens 34 comprises first and second lens elements 34a, 34b. It will be appreciated, however, that lens 34 may have various other configurations and may comprise only a single lens element, or more than two lens elements. In one embodiment, the light source 36 is a light emitting diode (LED) that is configured to provide bright illumination through the lens 34. Such an LED light source 36 is relatively lightweight and consumes a relatively small amount of power. While light source 36 is depicted in this embodiment as a single LED, it will be appreciated that light source 36 may alternatively comprise two or more LEDs, as may be desired. Electrical contacts 40, 42 are provided on the mounting structure 22 of the eyeglass frames 12 and the mounting structure 26 of the headlamp 20, respectively, to provide electrical communication between the light source 36 and the electrical circuitry of the eyeglass frames 12 when the headlamp 20 is mounted to the eyeglass frames 12.

In another aspect, the user-wearable illumination assembly 10 includes a battery power source that is removably couplable to the eyeglass frames 12 to provide power to the light source 36. In the embodiment shown, lithium polymer batteries 50a, 50b are provided on respective sides of the eyeglass frames 12, generally between the front frame portion 12a and the temple arms 12b. In this configuration, the batteries 50a, 50b form side shields for the eyeglass frames 12 to help protect a wearer's eyes against airborne debris, such as splattered body fluids or other material. The batteries 50a, 50b are removably coupled to the eyeglass frames 12 by snap-in-place connections, whereby the batteries 50a, 50b may be easily removed and replaced for minimal interruption to the user of the illumination assembly 10. The batteries 50a, 50b may be equipped with a microchip that enables smart battery technology to be utilized to optimize the charging and power usage of the batteries 50a, 50b on the illumination assembly 10. The batteries 50a, 50b may further include a charge monitor 54 for displaying information related to the charge and/or health of the batteries 50a, 50b. In the embodiment, shown, the charge monitor 54 includes illuminating elements 56 to provide a visual indication of the level of charge or the health of the batteries 50a, 50b. Alternatively, the charge monitor 54 may be configured to provide an audible indication related to the level of charge or health of the batteries 50a, 50b, or to provide both a visual and audible indication. It will be appreciated that various other structure may alternatively be provided to indicate information related to the charge and/or health of the batteries 50a, 50b.

While the illumination assembly 10 is shown and described herein as including a pair of batteries 50a, 50b in the form of side shields and comprising lithium polymer material, it will be appreciated that a single battery, or more than two batteries, may alternatively be used to provide power to the light source 36, and that various other materials or types of batteries may alternatively be used. Moreover, the one or more batteries may be configured to be secured to the eyeglass frames 12 in various other locations.

As non-limiting examples, batteries used with the illumination assembly 10, or any embodiment disclosed herein, may comprise lithium-ion batteries which utilize alginates as a binder material for the battery electrodes. The batteries may additionally, or alternatively, be formed from polymer gel film that facilitates shaping the batteries to various desired shapes. In one embodiment, the batteries may be sized and shaped to form the temple arms of the eyeglass frames themselves.

The eyeglass frames 12 of the exemplary user-wearable illumination assembly 10 further include electrical circuitry 58 integrated into the frames 12 for providing electrical communication between the removably mountable headlamp 20, the eyeglass frames 12, and the battery power source to provide power and/or electronic signals, such as for the control and operation of the light source 36. In one embodiment, conductive wiring may be provided through conduits formed in the eyeglass frames 12. In another embodiment, electrically conductive materials may be directly embedded into the structure of the eyeglass frames 12. The eyeglass frames 12 may further include control circuitry for an LED power supply and for driving an LED light source 36. The control circuitry may also be configured to monitor the state of charge or state of health of a battery power source, and to provide an indication to a user when a battery power source is ending or near the end of its useful charge.

In one embodiment, the user-wearable illumination assembly may further include a remote control configured to enable a user to turn the light source 36 on and off, and/or to adjust the output level of the light source 36. For example, the remote control may utilize radio signals or other electromagnetic signals to facilitate wireless communication between the remote control and the control circuitry. In another embodiment, the electrical circuitry 58 may be configured to turn the light source 36 on or off, or to adjust the output level of the light source 36. If the electrical circuitry 58 extends to the temple arms 12b of the eyeglass frames 12, flexible electrical connections, slip rings, or rotating electrical connectors may be used to facilitate folding of the temple arms 12b toward the front frame portion 12a of the eyeglass frames 12. The illumination assembly 10 may further include a switch 60 provided on the eyeglass frames to permit a user to turn the light source 36 of the headlamp 20 on or off, and/or to adjust the power provided to the light source 36 to adjust the intensity of illumination.

While the exemplary embodiments shown and described above include eyeglass frames 12 for supporting a headlamp 20, it will be appreciated that a user-wearable illumination assembly in accordance with the present disclosure may alternatively comprise various other types of user-wearable devices suitable for supporting a headlamp. For example, a headlamp 20, as described above, may alternatively be supported on goggles, face shields, masks, headbands, helmets, or various other user-wearable devices. Moreover, while headlamp 20 has been shown and described above as being removably mounted to eyeglass frames 12, it will be appreciated that various other embodiments may comprise a headlamp that is coupled to a user-wearable device such that it is not removable, or a headlamp that is integrally formed with the user-wearable device.

FIGS. 22-26 depict another exemplary embodiment of a user-wearable illumination assembly 110 in accordance with the present disclosure. The exemplary embodiment of FIGS. 22-26 is similar to the user-wearable illumination assembly 10 shown and described with respect to FIGS. 1-21, and similar features are similarly numbered. Accordingly, only the differences will be described herein.

In this embodiment, the first mounting structure 122 on the eyeglass frames 112 comprises a dumbbell-shaped slot proximate a bridge portion 124 of the frames 112. Bridge portion 124 also supports nose pads 128. The dumbbell-shaped slot has an opening on an upper side of the bridge portion 124 and defines two pockets 122a, 122b (see FIG. 26) extending toward a lower side of the bridge portion 124 for slidably receiving corresponding mounting structure 126 on headlamp 120, in a manner similar to that described above. The corresponding mounting structure 126 on headlamp 120 has a shape that is complementary to the dumbbell-shaped slot on eyeglass frames 112. Other features of headlamp 120 are similar to that described above with respect to headlamp 20.

The battery power source of illumination assembly 110 comprises lithium polymer batteries 150a, 150b provided on respective sides of the eyeglass frames 112 and positioned proximate the terminal ends 112c of the temple arms 112b. The temple arms are pivotally coupled to the front portion 112a of frames 112, such as by hinges 113. In this configuration, batteries 150a, 150b may be utilized to provide a counterbalance to the weight of the headlamp 120 and/or optical loupes 118a, 118b. In the embodiment shown, batteries 150a, 150b are removably received in respective battery housings 170a, 170b positioned at the terminal ends 112c of the temple arms 112b to facilitate quick and easy replacement of the batteries 150a, 150b, as may be required. The batteries 150a, 150b are releasably secured to the respective battery housings 170a, 170b by a snap-fit feature comprising a flexible tab 172 that engages a respective battery 150a, 150b when installed in the respectively associated battery housing 170a, 170b. To remove batteries 150a, 150b from the housings 170a, 170b, tabs 172 are depressed, thereby releasing the batteries 150a, 150b for removal. While batteries 150a, 150b have been shown and described in this embodiment as being releasably secured to housings 170a, 170b by a snap-fit feature, it will be appreciated that batteries 150a, 150b may alternatively be secured to battery housings 170a, 170b by various other methods. Batteries 150a, 150b may further include additional features similar to those described above with respect to batteries 50a, 50b.

While the batteries 150a, 150b of this exemplary embodiment, and the batteries described in the various other embodiments, have been described as lithium polymer batteries, it will be appreciated that various other types of batteries may alternatively be used.

In the embodiment shown, battery housings 170a, 170b are pivotally coupled to the terminal ends 112c of the respective temple arms 112b, such as by hinged joints 174, to permit pivotal movement of the battery housings 170a, 170b about substantially vertical axes such that each battery housing 170a, 170b can be selectively adjusted to a desired position toward or away from the oppositely disposed battery housing 170a, 170b. The battery housings 170a, 170b may thereby be adjusted to a position adjacent to or in contact with the head of the wearer. In the embodiment shown, battery housings 170a, 170b are pivotally adjustable about axes that are substantially parallel to the axes provided by hinges 113 that facilitate the folding of temple arms 112b. Pads 176 or other cushioning elements may be provided on interiorly facing sides of the battery housings 170a, 170b to provide a comfortable feel to the wearer.

While battery housings 170a, 170b are shown and described herein as being pivotally coupled to the terminal ends 112c of temple arms 112b by hinged joints 174, it will be appreciated that the batteries 150a, 150b may alternatively be coupled proximate the terminal ends 112c of temple arms 112b by various other methods suitable to facilitate selectively adjusting the position of the batteries 150a, 150b relative to the head of a user. As a non-limiting example, batteries 150a, 150b may alternatively be coupled proximate the terminal ends 112c of temple arms 112b by flexible connecting structure that can be deformed by the user to engage the user's head, as may be desired.

User-wearable illumination assembly 110 further includes control circuitry and electrical circuitry integrated into frames 112 for providing electrical communication between the removably mountable headlamp 120, eyeglass frames 112, and batteries 150a, 150b, as described above. The illumination assembly 110 may further include user controls 180 and indicators 182 to facilitate operation of headlamp 120, and to communicate information regarding the condition or health of the batteries 150a, 150b to a user. In the embodiment shown, user controls and indicators may be provided on at least one of the temple arms 112b. For example, buttons or switches 180a, 180b, 180c may be provided to enable the user to turn the headlamp 120 on and off, and/or to enable the user to adjust the intensity of illumination provided by the headlamp 120. Indicators 182 may provide a visual and/or audible indication related to the condition or health of the batteries 150a, 150b, or provide various other information to the user.

In addition to, or as an alternative to controls 180 such as buttons or switches 180a, 180b, 180c provided on temple arms 112b, user-wearable illumination assembly 110 may further include controls in the form of one or more touch-sensitive capacitance switches 184 provided on other portions of the eyeglass frames 112, such as on the brow portions 186a, 186b of the frames 112, generally located laterally from the bridge portion 124. The touch-sensitive capacitance switches 184 may be integrated with the eyeglass frames 112, or may be disposed on an outer surface of the eyeglass frames 112. When located on the brow portions 186a, 186b of the eyeglass frames 112, the touch-sensitive capacitance switches 184 provide a convenient way to selectively turn power to the headlamp 120 on and off, and/or selectively adjust the intensity of the illumination provided by headlamp 120 by contacting the touch-sensitive capacitance switches 184 with a portion of the body, such as the back of the hand. This configuration may provide more convenient access to controls than when controls are located on the temple arms 112, or other portions of the eyeglass frames 112, particularly for users having long hair, which may interfere with access to temple arm-mounted controls, or when a user desires to adjust the output of the headlamp 120 while maintaining the sterility of their hands, such as during the performance of surgical procedures.

FIGS. 27-31 depict another exemplary embodiment of a user-wearable illumination assembly 210 for use with eyeglass frames 212 in accordance with the present disclosure. In the embodiment shown, the illumination assembly 210 is configured to be selectively removably coupled to the bridge portion 214 of the eyeglass frames 212. The eyeglass frames 212 define a pair of apertures 216a, 216b for supporting lenses 218a, 218b on the eyeglass frames 212. In the embodiment shown, individual lenses 218a, 218b are carried by each aperture of the eyeglass frames 212. It will be appreciated, however, that a single lens may alternatively be carried by the eyeglass frames 212, with the single lens extending between both apertures 216a, 216b. Alternatively, eyeglass frames 212 with which the illumination assembly 210 can be used may be provided without individual apertures 216a, 216b, and may instead include a single lens extending between temple arms 220a, 220b of the frames 212.

In the embodiment shown, the eyeglass frames 212 further include a pair of magnification loupes 222a, 222b supported through the respective lenses 218a, 218b. It will be appreciated, however, that the eyeglass frames 212 with which the illumination assembly 210 can be used may not include optical loupes 222a, 222b, or that optical loupes 222a, 222b may alternatively be provided on a flip-up style mounting, such as the mounting shown and described in U.S. Patent Application Publication No. 2007/0153498, for example, instead of being mounted through the lenses 218a, 218b as depicted herein. Exemplary optical loupes 222a, 222b for use in the illumination assembly 210 are disclosed in U.S. Pat. No. 7,072,124 to Wilt et al. U.S. Patent Application Publication No. 2007/0153498 and U.S. Pat. No. 7,072,124 are assigned to the assignee of the present invention.

With continued reference to FIGS. 27-31, the illumination assembly 210 comprises a clip assembly 230 for selectively removably coupling the illumination assembly 210 to the bridge portion 214 of the eyeglass frames 212. The clip assembly 230 includes a body portion 232 and first and second clamp members 234, 236 extending generally downwardly therefrom and defining structure for securing the illumination assembly 210 to the bridge portion 214 of the eyeglass frames 212. In the embodiment shown, the first clamp member 234 is hingedly coupled to the second clamp member 236, and is biased in a direction toward the second clamp member 236, such as by a spring, a resilient member, or by other suitable structure, so that the bridge portion 214 of the eyeglass frames 212 may be clamped between the first and second clamp members 234, 236 to couple the clip assembly 230 to the eyeglass frames 212. While the first clamp member 234 is depicted as being hingedly coupled to the second clamp member 236, it will be appreciated that the first clamp member 234 may alternatively be hingedly coupled directly to the body portion 232, or that clamping structure may be provided in various other configurations to facilitate clamping the clip assembly 230 to the bridge portion 214 of the eyeglass frames 212.

In the embodiment shown, the first and second clamp members 234, 236 each include clamp arms 234a, 234b, 236a, 236b extending generally downwardly and outwardly from central portions of the clamp members 234, 236 to provide a secure connection with the eyeglass frames 212 without obstructing a nose piece of the eyeglass frames 212. While not depicted herein, the clip assembly 230 may further include a locking feature to prevent inadvertent release of the first and second clamping members 234, 236 from the bridge portion 214 of the eyeglass frames 212 after the clip assembly 230 has been attached.

The illumination assembly 210 further includes a head lamp 240 coupled to the body portion 232 of the clip assembly 230 by first and second support arms 242, 244. A first joint 246 is provided between the first and second support arms 242, 244, and a second joint 248 is provided between the second support arm 244 and the headlamp 240 to provide for articulating movement of the headlamp 240 relative to the body 232 of the clip assembly 230 and thereby facilitate positioning and orienting the headlamp 240, as may be desired. It will be appreciated, however, that various other structure for mounting the headlamp 240 to the clip assembly 230 may alternatively be provided.

Figure 30:
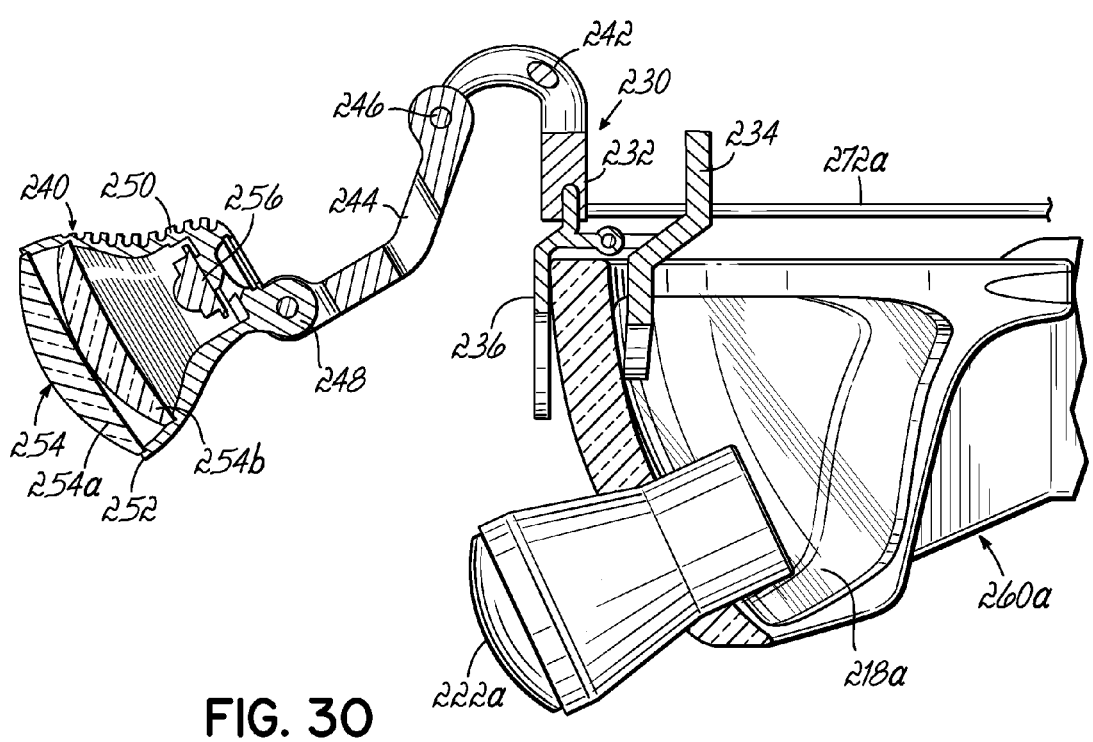
FIG. 30 is a partial cross-sectional view taken along line 30-30 of FIG. 27.
Figure 31:
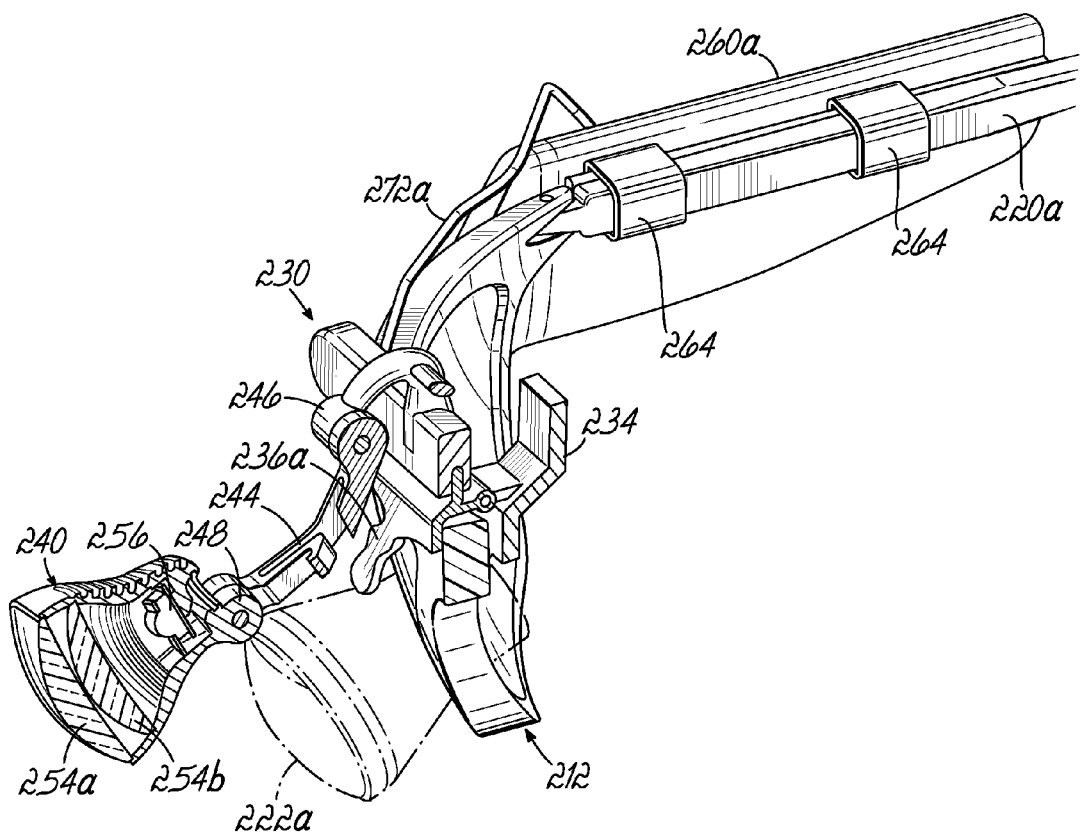
FIG. 31 is a perspective view of the cross-section depicted in FIG. 30.
Figure 32:
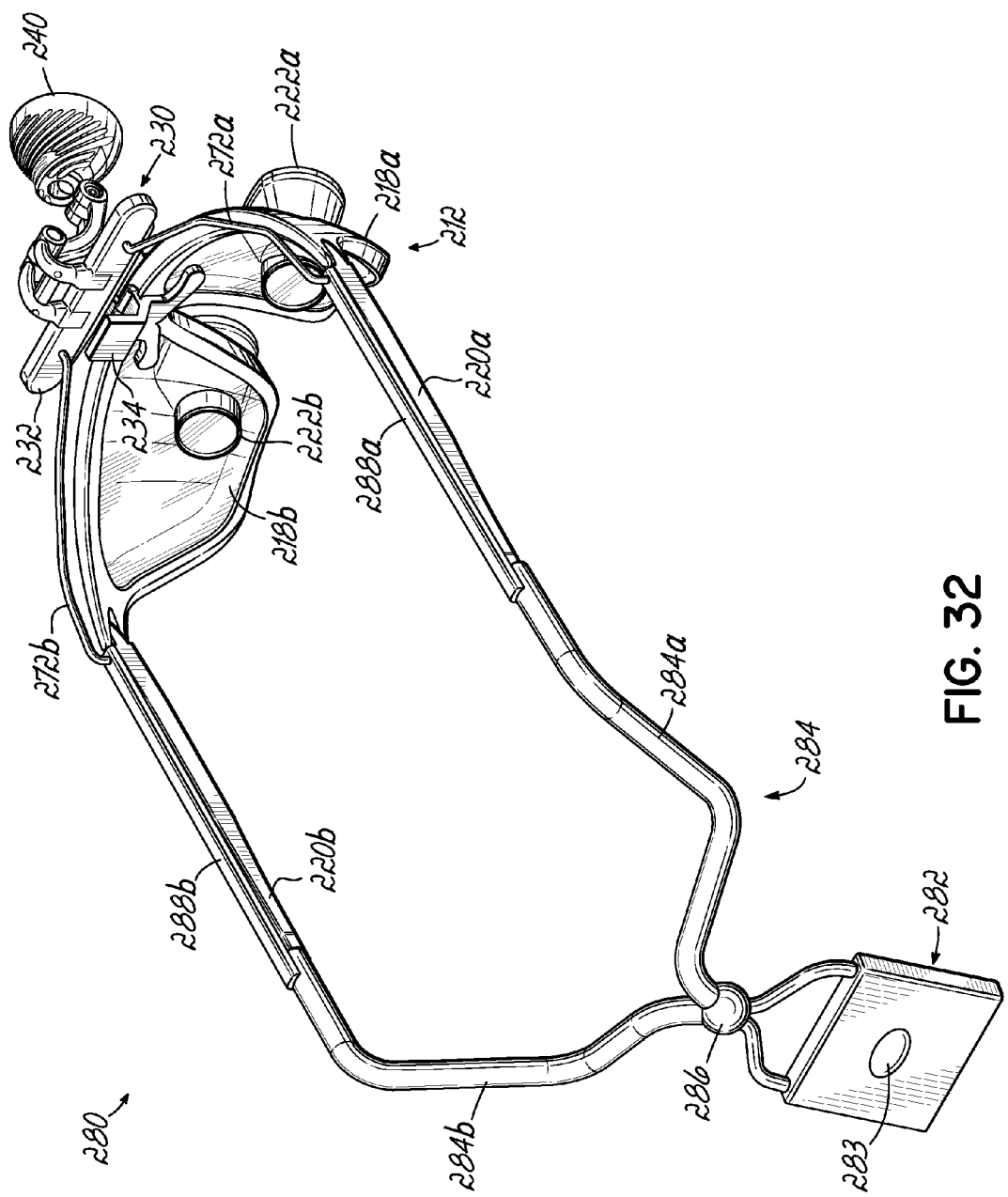
FIG. 32 is perspective view of another embodiment of a user-wearable illumination assembly for use with eyeglass frames, in accordance with the present disclosure.
Figure 33:
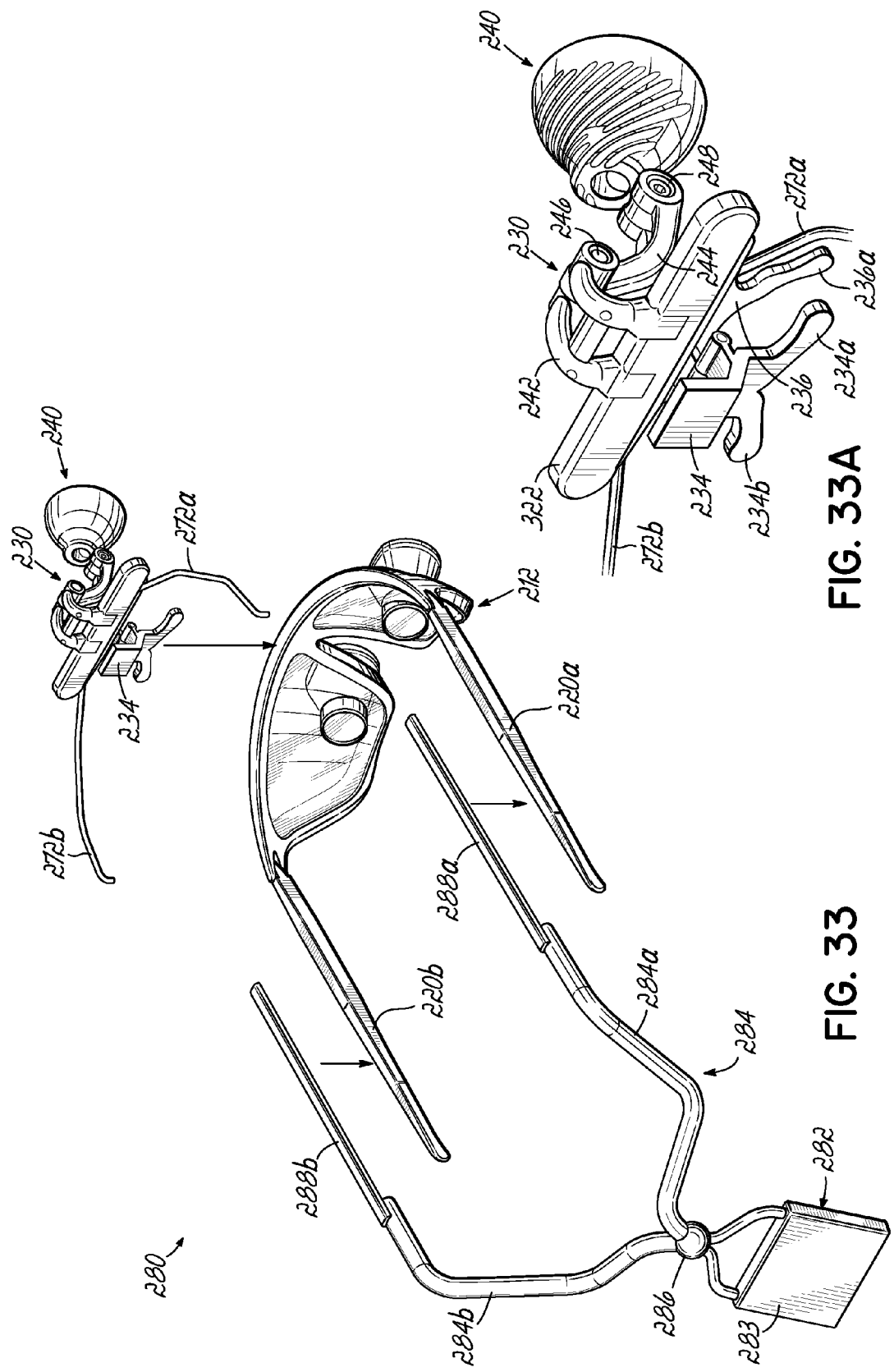
FIG. 33 is an exploded perspective view of the user-wearable illumination assembly of FIG. 32.
Figure 34:
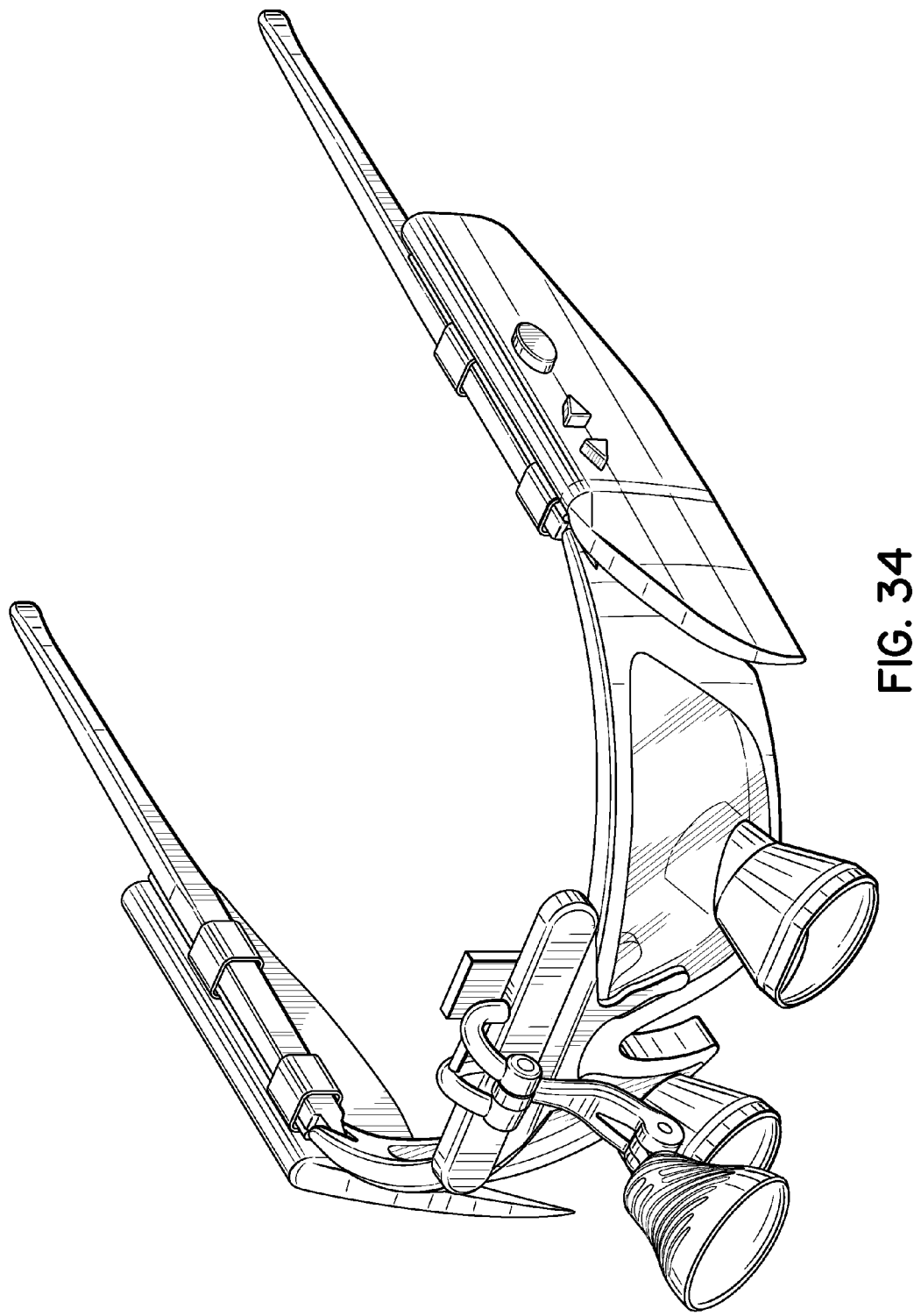
FIG. 34 is another perspective view of the user-wearable illumination assembly of FIG. 27, illustrating the ornamental design of the exemplary embodiment.
Figure 35:
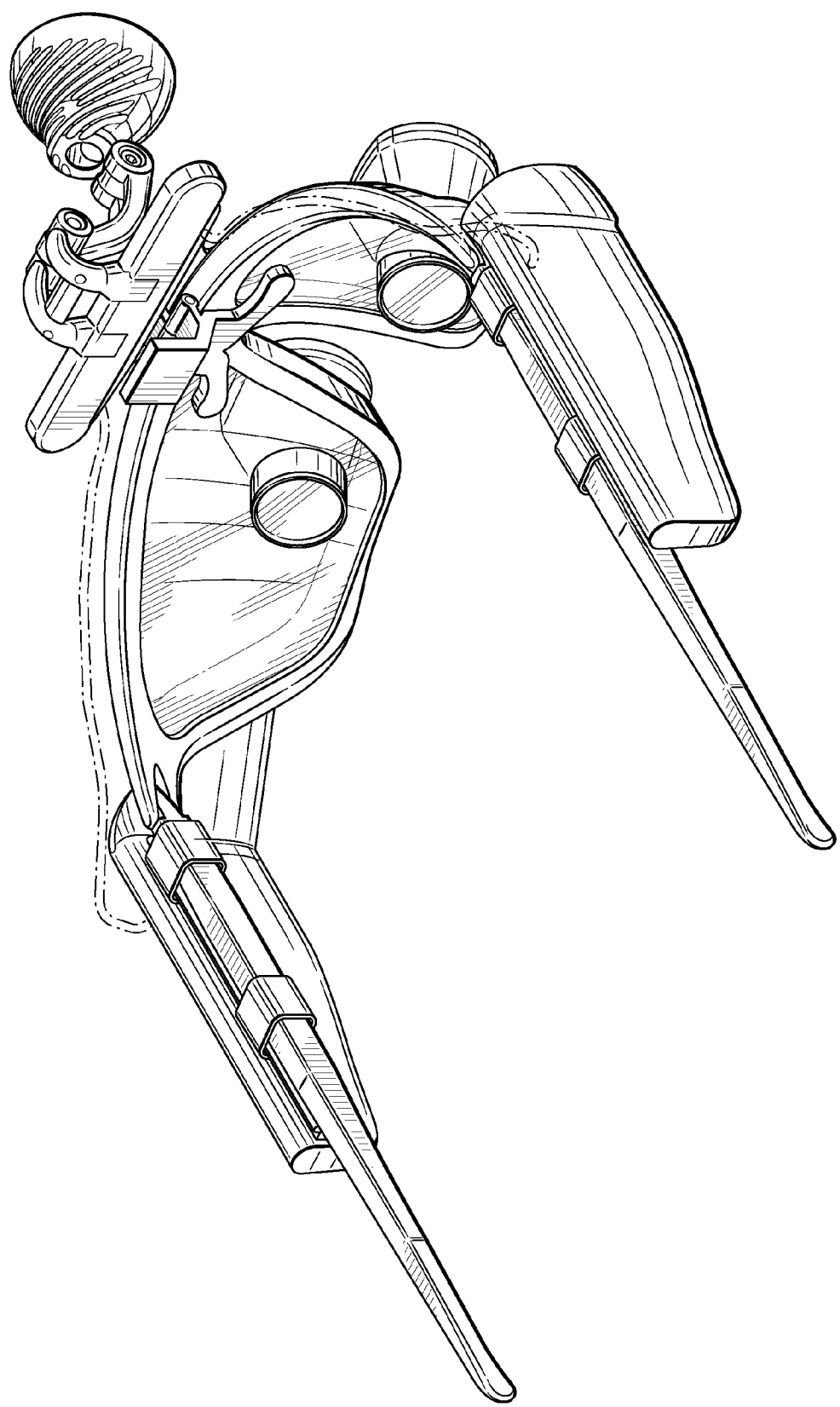
FIG. 35 is another perspective view of the user-wearable illumination assembly of FIG. 34, viewed from another direction.
Figure 38:
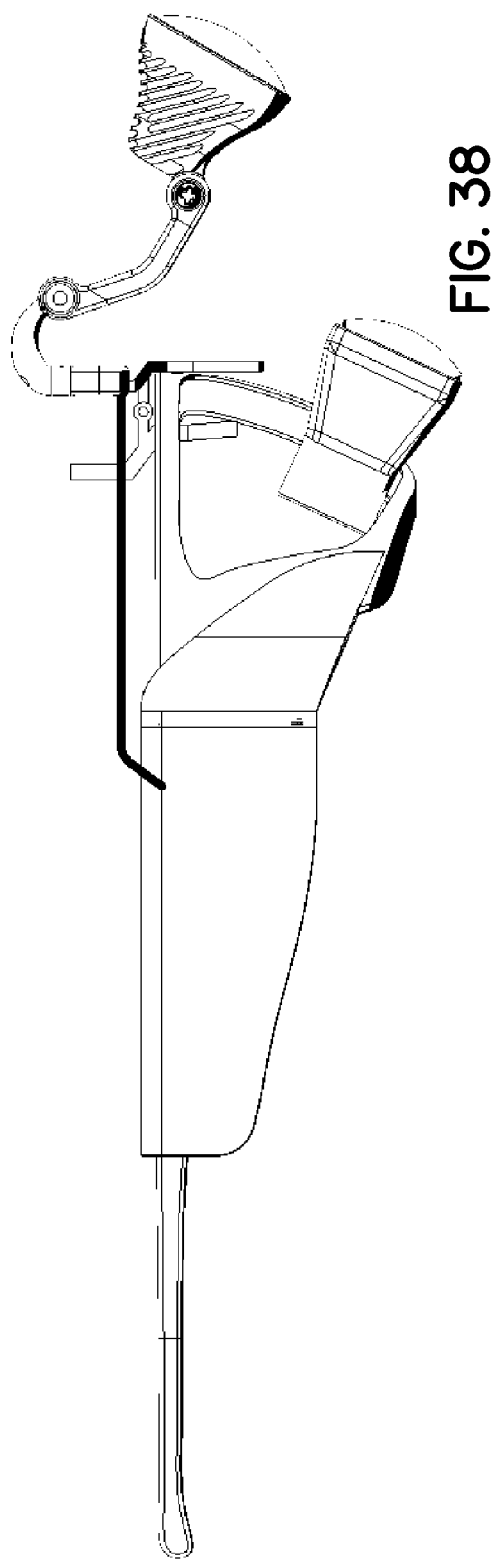
FIG. 38 is a right-side elevation view thereof.
Figure 39:
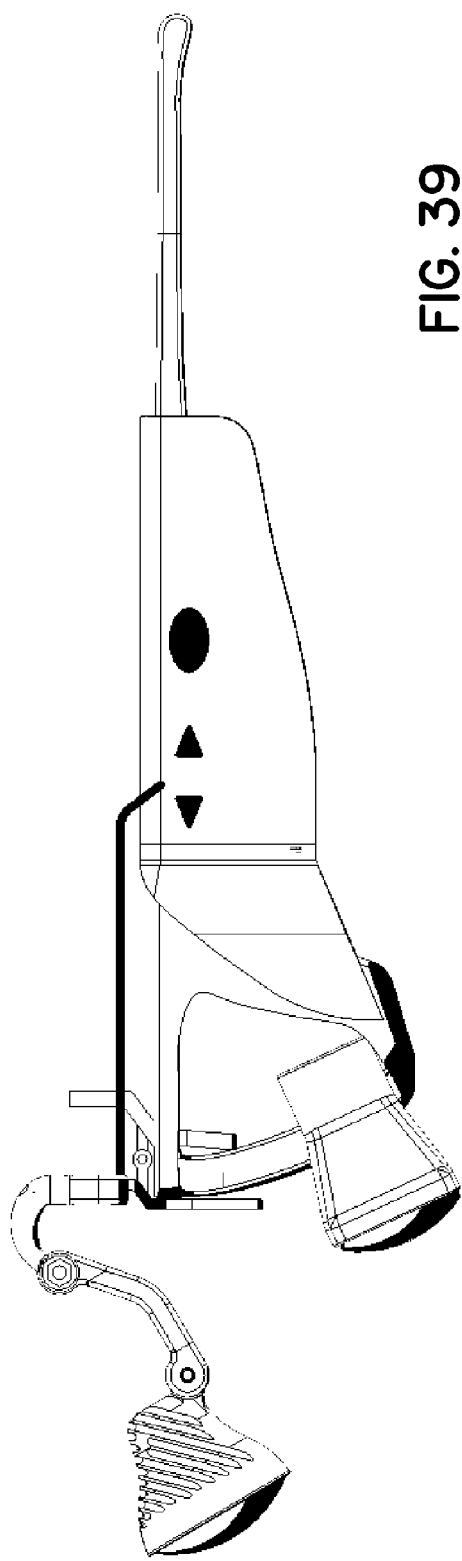
FIG. 39 is a left-side elevation view thereof.
Figure 40:
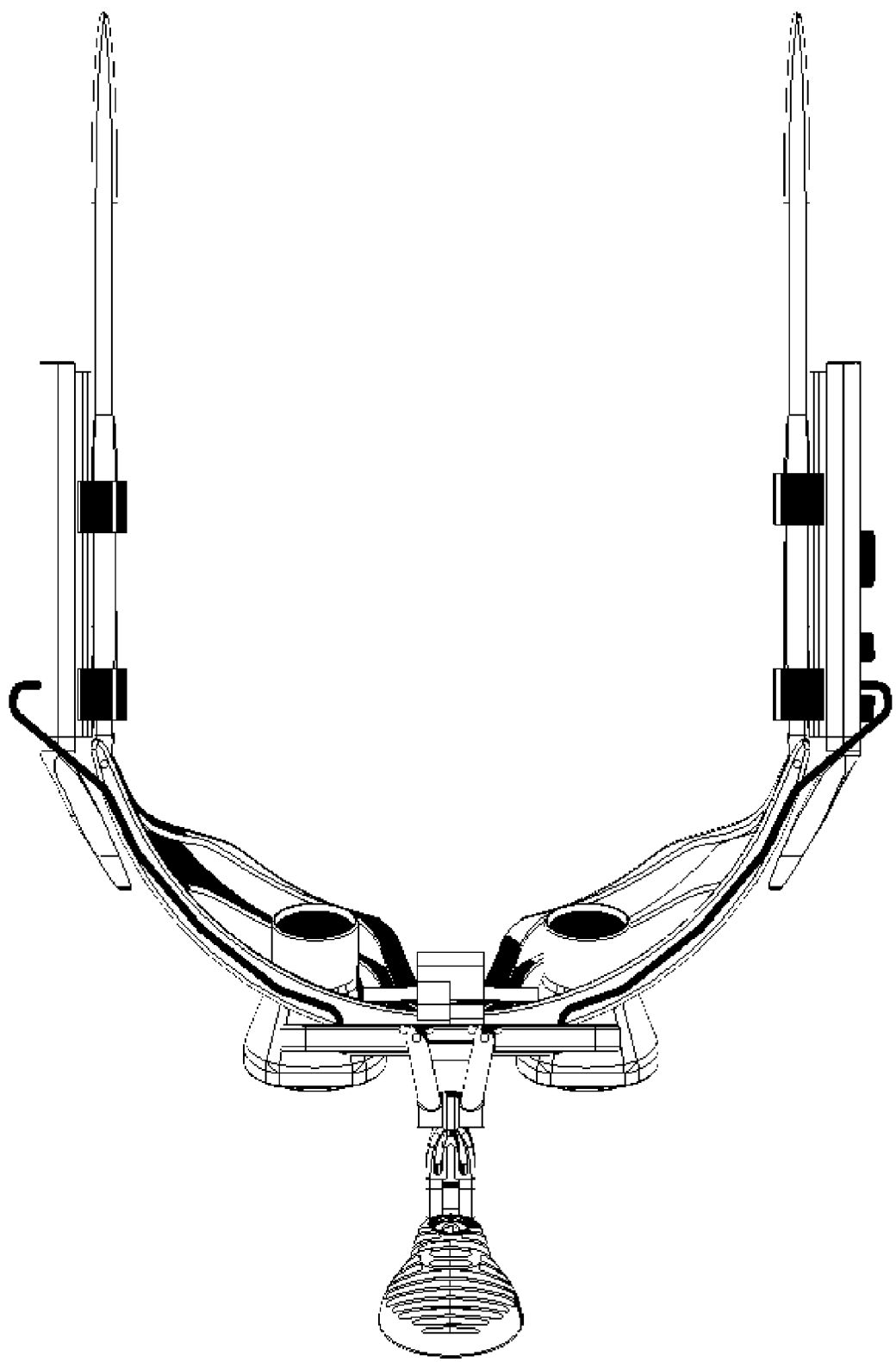
FIG. 40 is a top plan view thereof.
Figure 41:
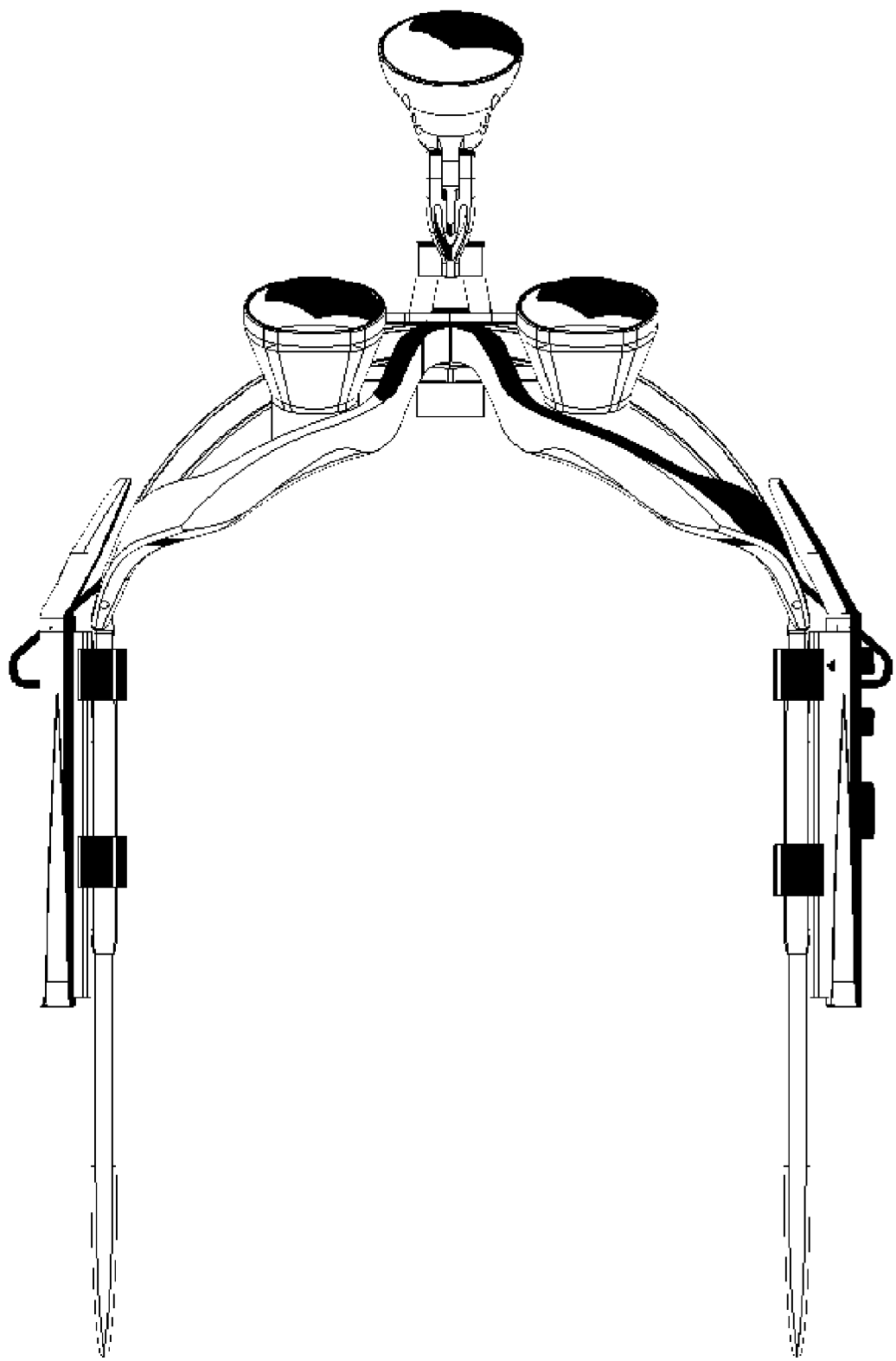
FIG. 41 is a bottom plan view thereof.
Figure 42:
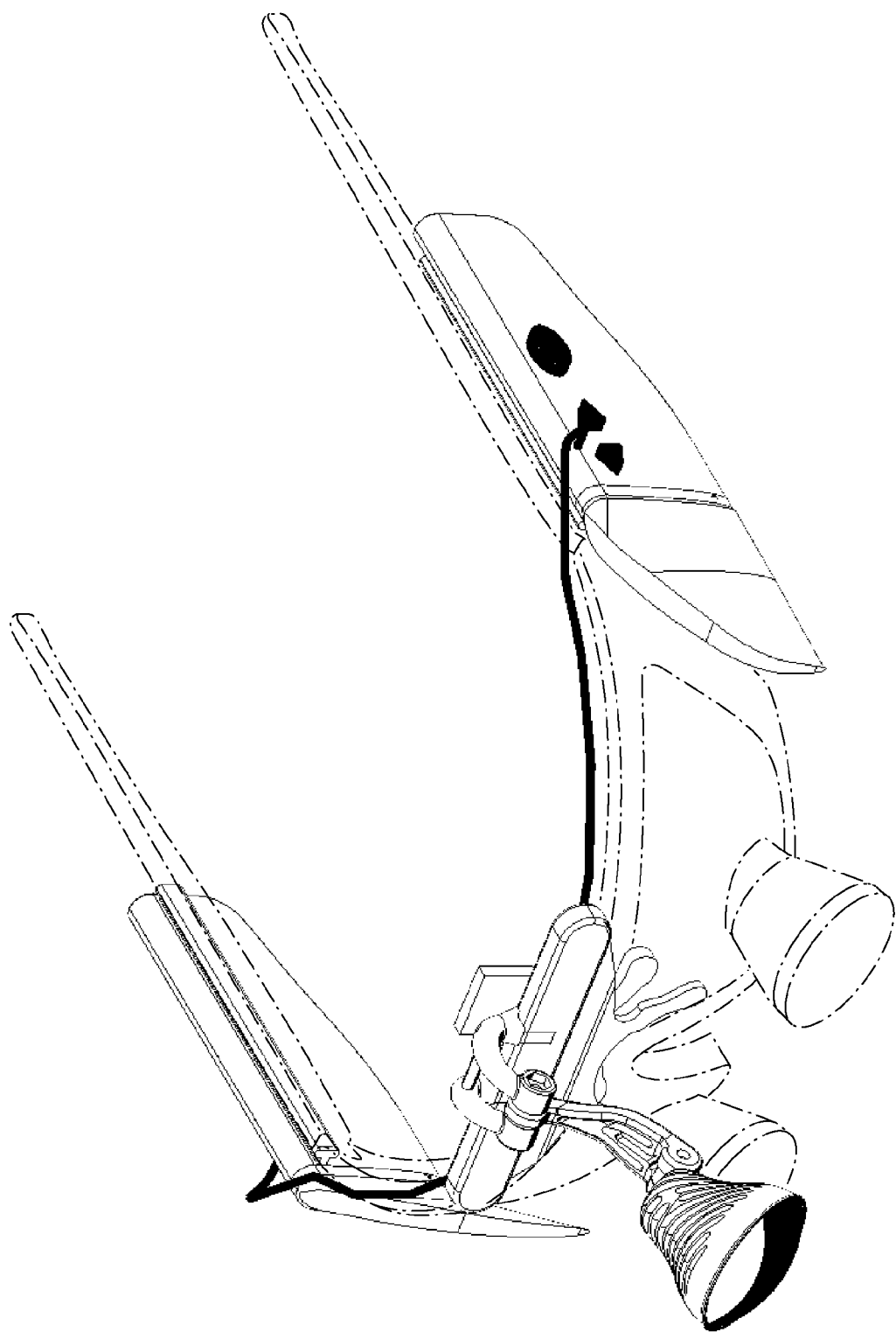
FIG. 42 is a perspective view of another exemplary embodiment of a user-wearable illumination assembly, illustrating the ornamental design of the embodiment and depicting eyeglass frames in phantom.
Figure 42A:
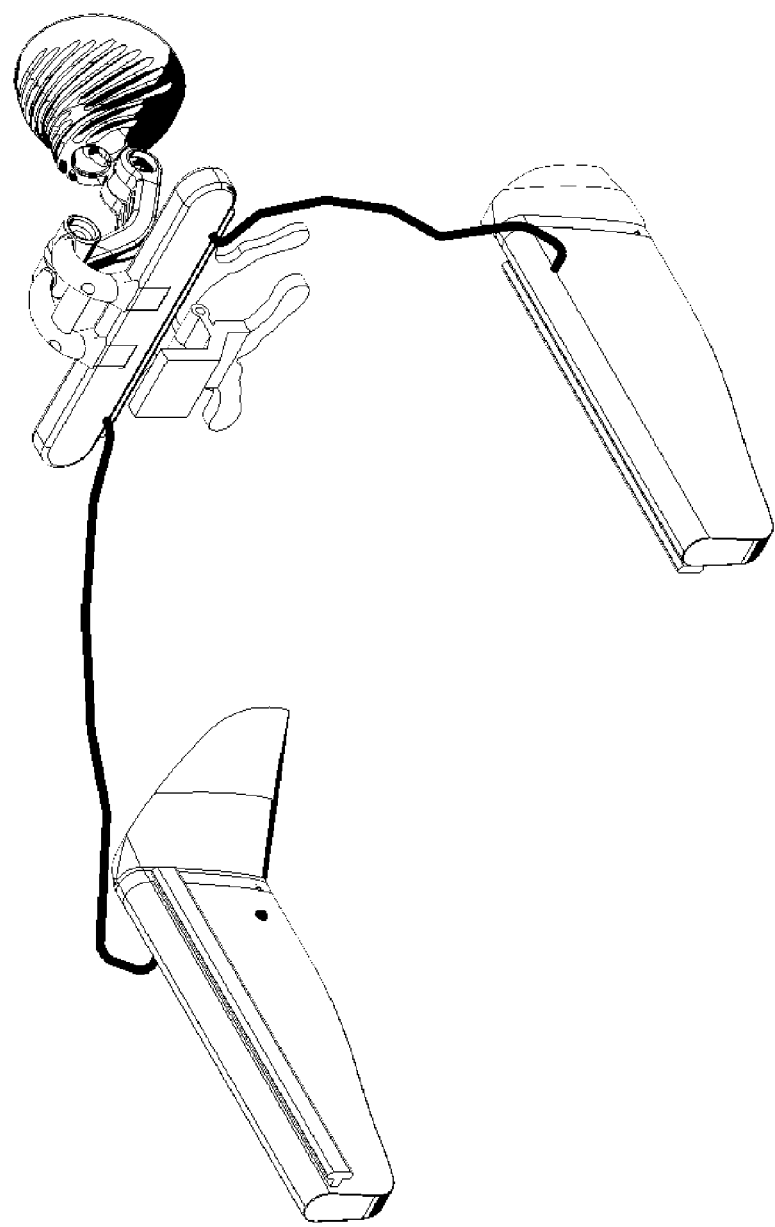
FIG. 42A is another perspective view of the user-wearable illumination assembly of FIG. 42, viewed from another direction.
Figure 45:
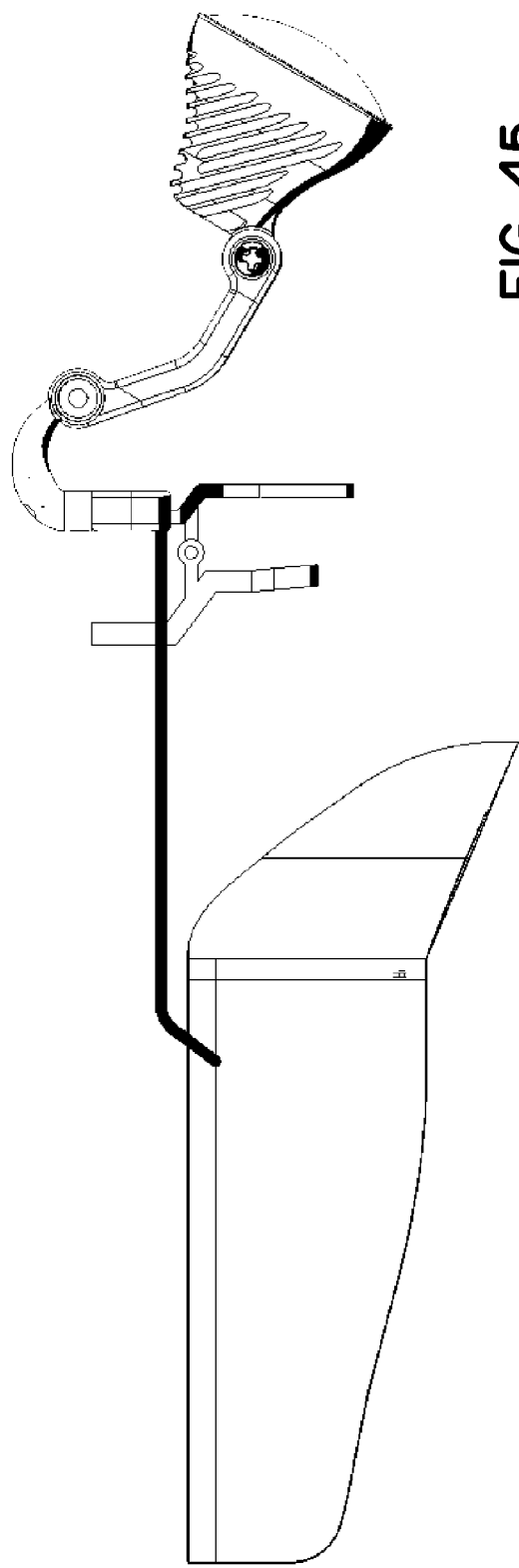
FIG. 45 is a right-side elevation view thereof.
Figure 46:
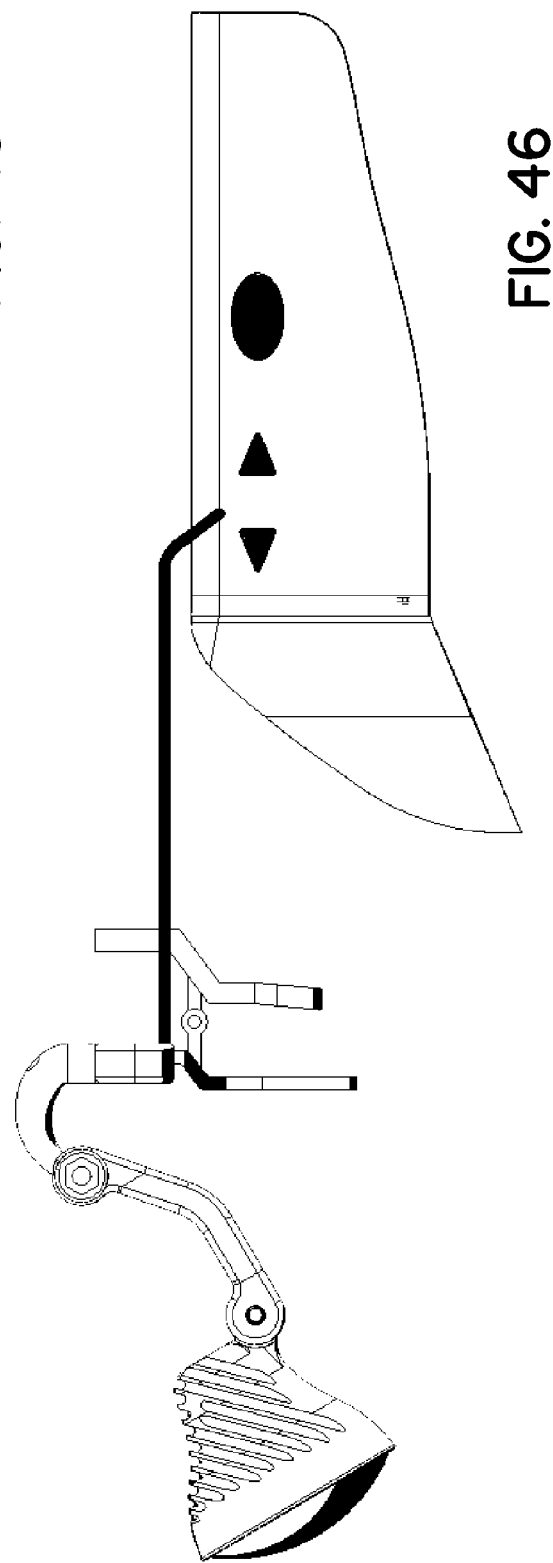
FIG. 46 is a left-side elevation view thereof.
Figure 47:
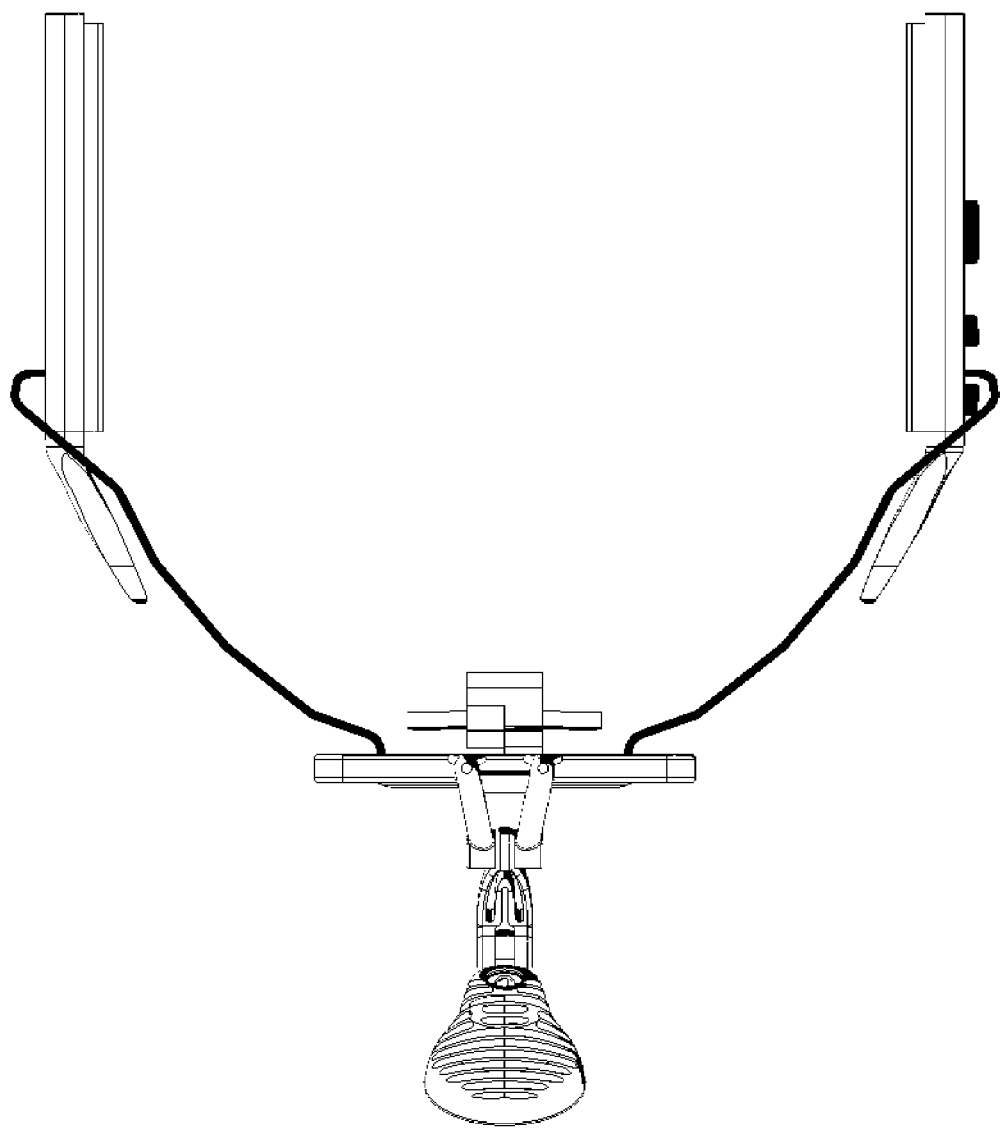
FIG. 47 is a top plan view thereof.
Figure 48:
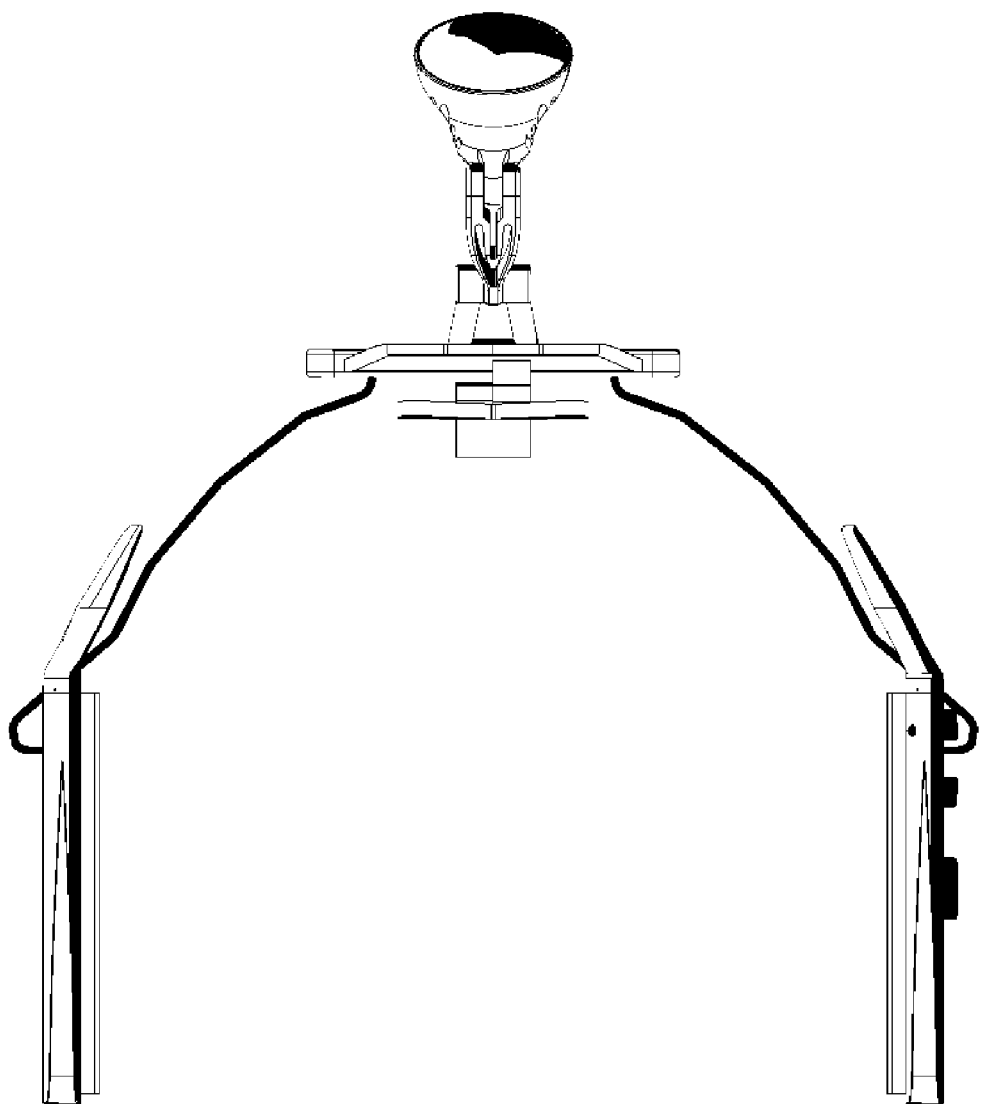
FIG. 48 is a bottom plan view thereof.

With particular reference to FIGS. 30-31, the headlamp 240 comprises a housing 250 having an open end 252 for supporting a lens 254 thereon. A light source 256 is supported within the housing 250 and generally behind the lens 254. In this embodiment, lens 254 comprises first and second lens elements 254a, 254b. It will be appreciated, however, that lens 254 may have various other configurations and may, for example, comprise only a single lens element, or more than two lens elements. In one embodiment, the light source 256 is a light emitting diode (LED) that is configured to provide bright illumination through the lens 254. Such an LED light source 256 is relatively lightweight and consumes a relatively small amount of power. While light source 256 is depicted in this embodiment as a single LED, it will be appreciated that light source 256 may alternatively comprise two or more LEDs, as may be desired.

Figure 28:
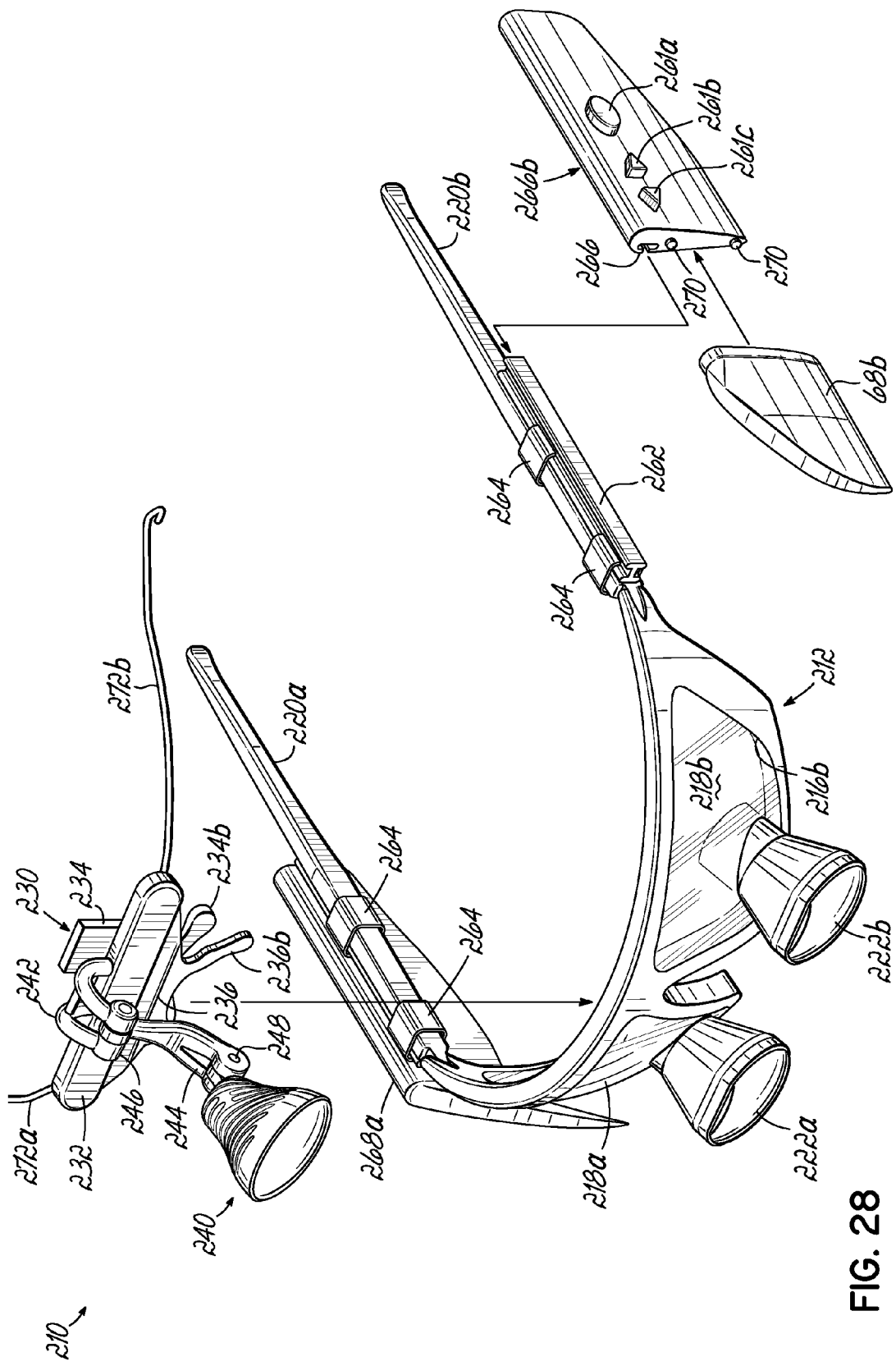
FIG. 28 is an exploded perspective view of the user-wearable illumination assembly of FIG. 27.
Figure 29:
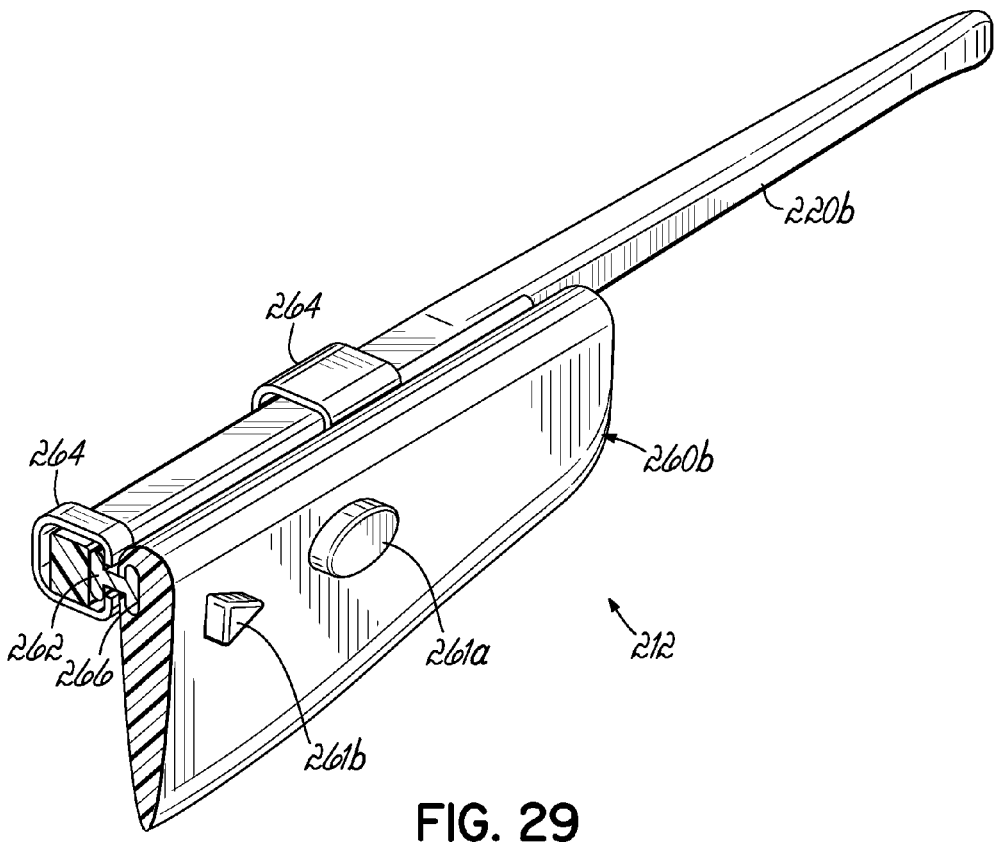
FIG. 29 is a partial cross-sectional view taken along line 29-29 of FIG. 27 and illustrating the attachment of a battery.

The user-wearable illumination assembly 210 further includes a battery power source that is selectively removably couplable to the eyeglass frames 212 to provide power to the light source 256 of the headlamp 240. In the embodiment shown, first and second lithium polymer batteries 260a, 260b are provided on respective sides of the eyeglass frames 212, and generally along the temple arms 220a, 220b. The illumination assembly 210 includes attachment structure that can be selectively attached to the temple arms 220a, 220b, and corresponding attachment structure is provided on the batteries 260a, 260b to facilitate selective mounting of the batteries 260a, 260b to the temple arms 220a, 220b. In the embodiment shown, attachment structure for the temple arms 220a, 220b includes rails 262 that that can be removably coupled to the temple arms 220a, 220b by respective brackets 264. With reference to FIG. 28, rails 262 of this embodiment have generally I-shaped cross-sections. The corresponding attachment structure on the batteries 260a, 260b include complementarily-shaped channels 266 formed along an upper edge of the batteries 260a, 260b for slidably receiving the rails 262 therein when the batteries 260a, 260b are coupled to the temple arms 220a, 220b of the eyeglass frames 212. It will be appreciated, however, that various other structure may alternatively be used to facilitate selectively removably coupling the batteries 260a, 260b to the temple arms 220a, 220b.

The batteries 260a, 260b may further include additional attachment structure to facilitate coupling side shields 268a, 268b to forward facing ends of the batteries 260a, 260b. In the embodiment shown, the additional attachment structure includes projections 270 on the distal ends of the batteries 260a, 260b for engaging complementarily-shaped recesses on the side shields 268a, 268b. When coupled in this arrangement, the batteries 260a, 260b and side shields 268a, 268b cooperate to help protect a wearer's eyes against airborne debris, such as splattered body fluids or other material. The side shields 268a, 268b may also be configured to facilitate securely retaining the batteries 260a, 260b on the rails 262 when the batteries 260a, 260b are received on the rails 262.

The batteries 260a, 260b may be equipped with a microchip that enables smart battery technology to be utilized to optimize the charging and power usage of the batteries 260a, 260b on the illumination assembly 210. The illumination assembly 210 may further include a charge monitor for displaying information related to the charge and/or health of the batteries 260a, 260b. In one embodiment, the charge monitor may include illuminating elements to provide a visual indication of the level of charge or health of the batteries 260a, 260b. The illuminating elements may be positioned on the clip assembly 230, on the batteries 260a, 260b, or at various other locations of the illumination assembly 210 to provide the visual indication to the wearer of the device. Alternatively, the charge monitor may be configured to provide an audible indication related to the level of charge or health of the batteries 260a, 260b, or to provide both a visual and audible indication. It will be appreciated, however, that various other structure may alternatively be provided to indicate information related to the charge and/or health of the batteries 260a, 260b.

At least one of the batteries 260a, 260b may further include user-actuatable controls to facilitate operation of the illumination assembly 210. In the embodiment shown, battery 260b includes a button 261a for selectively activating and deactivating power to headlamp 240, and buttons 261b, 261c to selectively adjust the intensity of the light emitted by light source 256. It will be appreciated that user-actuatable controls may comprise various other structure, and/or may be provided on various other structure of the illumination assembly 210 to control various other functions of the illumination assembly 210 to facilitate operation by a user of the device.

In another embodiment, the user-wearable illumination assembly 210 may further include a remote control 265 configured to enable a user to control various functions of the illumination assembly 210. For example, the remote control may utilize radio signals or other electromagnetic signals to facilitate wireless communication between the remote control and control circuitry of the illumination assembly 210 and thereby turn the light source 256 on or off, adjust the output level of the light source 256, or control various other functions of the illumination assembly 210.

The illumination assembly 210 may further include one or more electrical conductors for providing electrical communication between the batteries 260a, 260b and the light source 256 of the headlamp 240. In the embodiment shown first and second electrical conductors 272a, 272b extend between the body portion 232 of the clip assembly 230 and the first and second batteries 260a, 260b, respectively. The first and second electrical conductors 272a, 272b may then be further routed to the light source 256. Alternatively, additional electrical conductors may be provided in or on the body portion 232 of the clip assembly 230 and the support arms 242, 244 supporting the headlamp 240 thereon, to provide electrical communication further to the light source 256. For example, electrical circuitry may be integrated into the body portion 232 and/or the support arms 242, 244 for providing electrical communication between the body portion 232 and the light source 256. The electrical circuitry may be capable of providing power and/or electronic signals, such as for the control and operation of the light source 256. The illumination assembly may further include control circuitry for an LED power supply and for driving an LED light source 236. The control circuitry may also be configured to monitor the state of charge or state of health of a battery power source, and to provide an indication to a user when a battery power source is ending or near the end of its useful charge. Such control circuitry may be integrated within the body portion 232 of the clip assembly 230, for example.

Referring now to FIGS. 32, 33, 33A, and 49-56, another exemplary embodiment of a user-wearable illumination assembly 280 for use with eyeglass frames 212 in accordance with the present disclosure is illustrated. Many features of the illumination assembly 280 are the same, or are similar to, features described above with respect to the illumination assembly 210 of FIGS. 27-31, and detailed discussion of these features is not repeated here. Similar features illustrated in the drawings have been similarly numbered. In this embodiment, one or more batteries may be provided for attachment near terminal ends of the temple arms 220a, 220b, around the backside of the wearer's head. Such an arrangement may be configured to counterbalance the weight of one or more of the clip assembly 230, the headlamp 240, and/or the optical loupes 222a, 222b of the eyeglass frames 212 (if provided). In the embodiment shown, a battery 282 is coupled to first and second strap members 284a, 284b of a head strap 284 that is selectively removably attachable to the temple arms 220a, 220b of the eyeglass frames 212. The first and second strap members 284a, 284b may be selectively deformable to facilitate conforming the head strap 284 to the shape of the head of a wearer and thereby provide a custom fit for the illumination assembly 280.

The illumination assembly 280 may further include an adjustable member 286 coupled to head strap 284 for sliding movement along the first and second strap members 284a, 284b to further facilitate adjusting the head strap 284, as may be desired by a wearer of the illumination assembly 280. The illumination assembly 280 may further include first and second conduits 288a, 288b associated with the first and second strap members 284a, 284b, respectively, wherein at least one of the conduits 288a, 288b may be used to route electrical conductors 272a, 272b between the battery 282 and the light source 256 of the headlamp 240. For example, one or more electrical conductors 272a, 272b may be routed from the battery 282, through one or more of the first and second strap members 234a, 234b, through one or more of the first and second conduits 288a, 288b, to the body portion 232 of the clip assembly, as described above.

Figure 49:
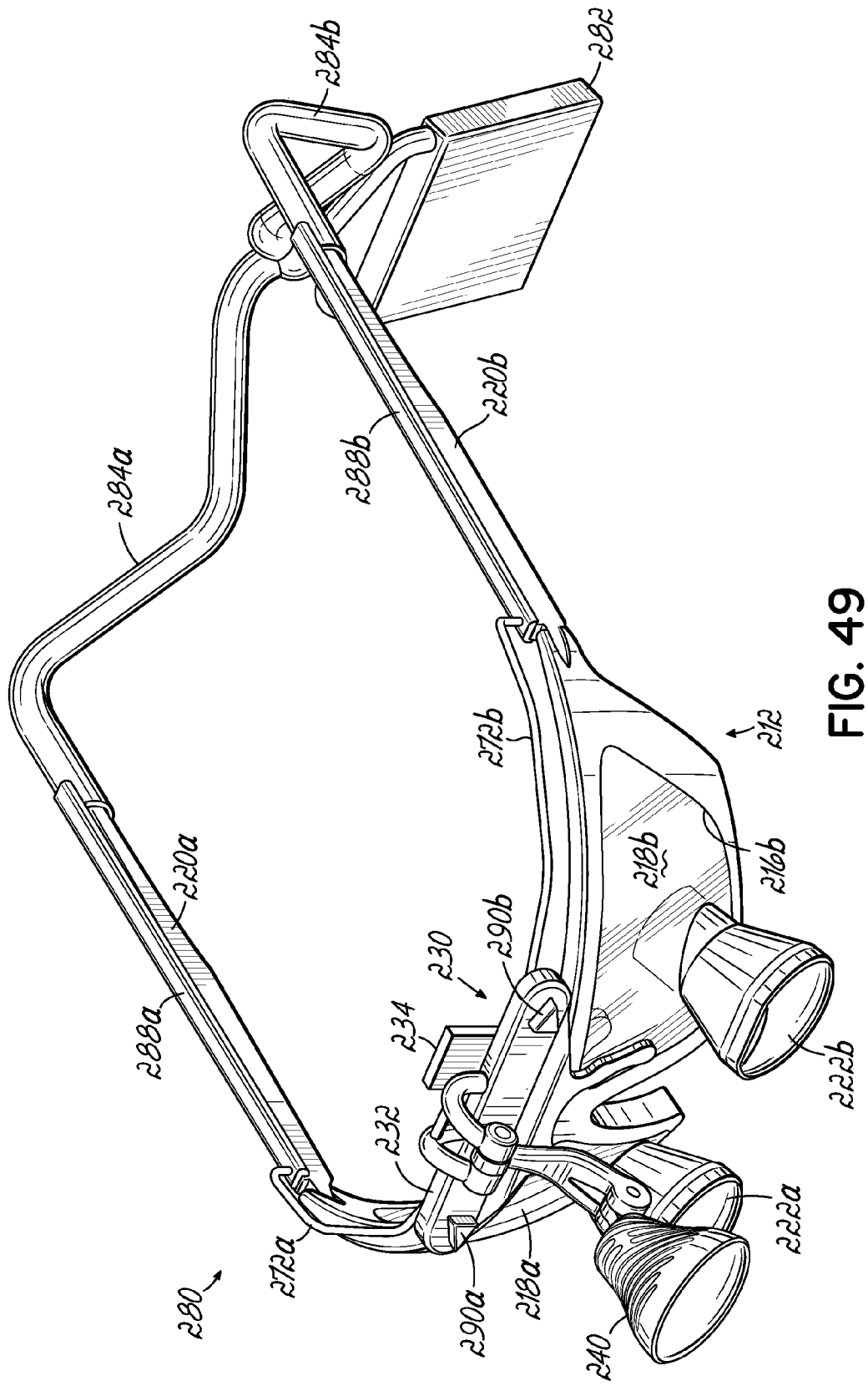
FIG. 49 is a perspective view of the user-wearable illumination assembly of FIG. 32, illustrating the ornamental design of the exemplary embodiment.
Figure 50:
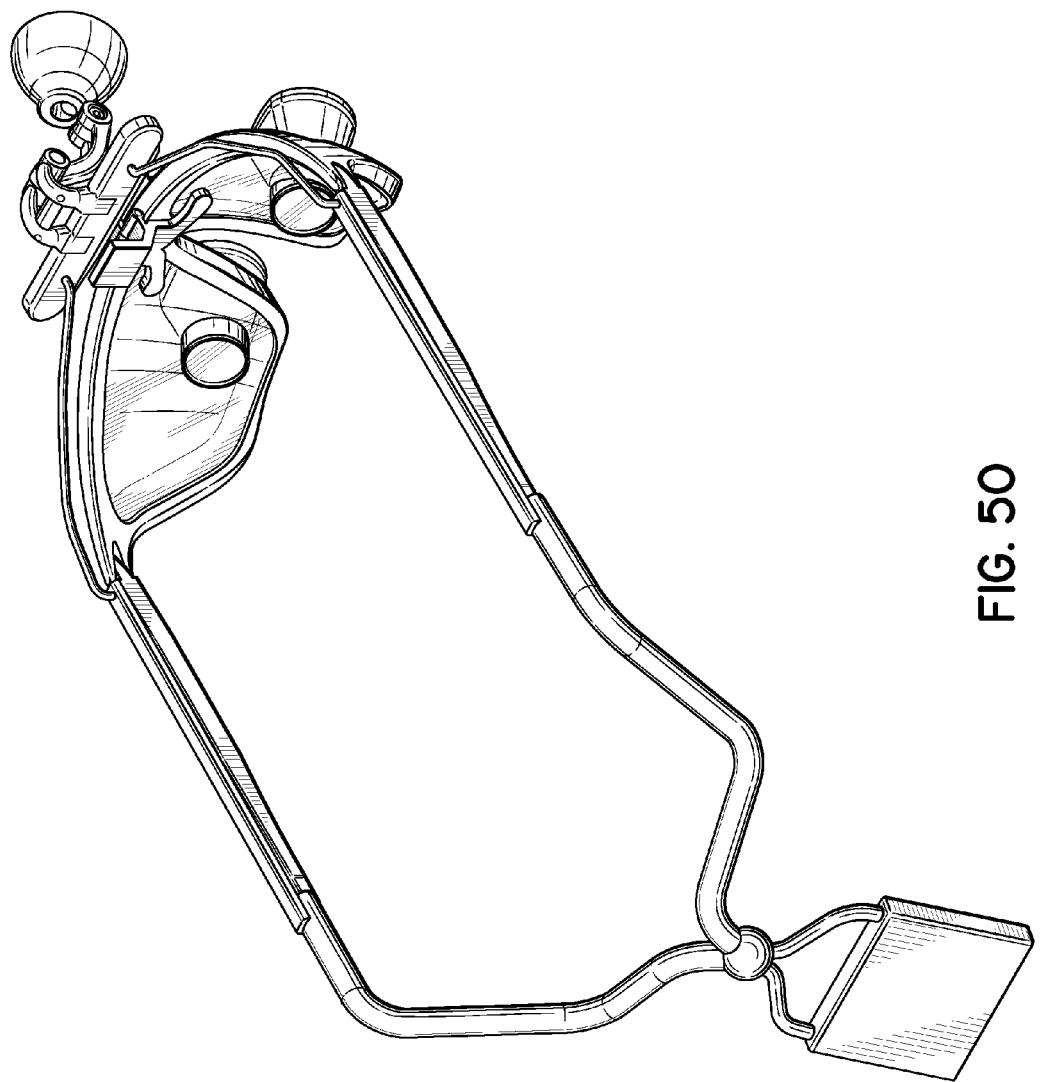
FIG. 50 is another perspective view of the user-wearable illumination assembly of FIG. 49, viewed from another direction.
Figure 51:
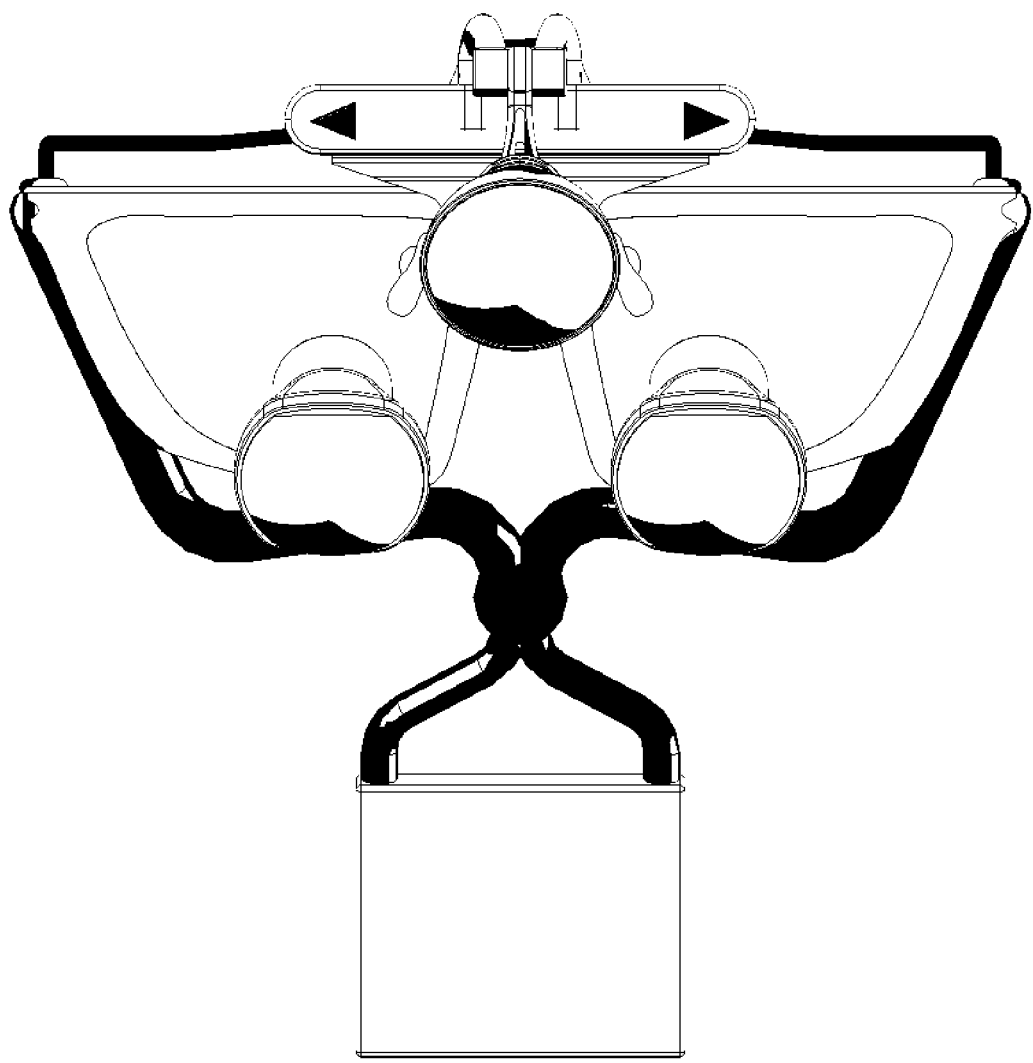
FIG. 51 is a front elevation view thereof.
Figure 52:
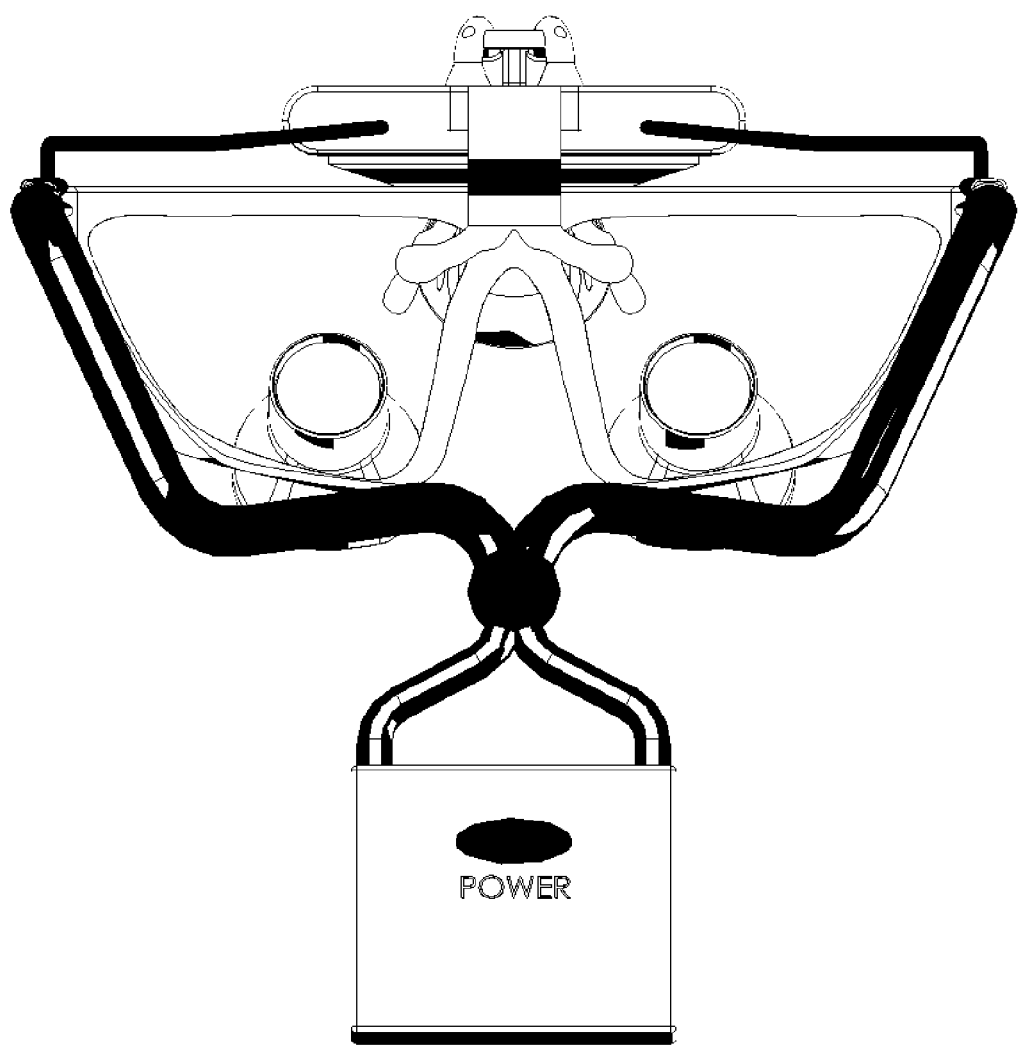
FIG. 52 is a rear elevation view thereof.
Figure 53:
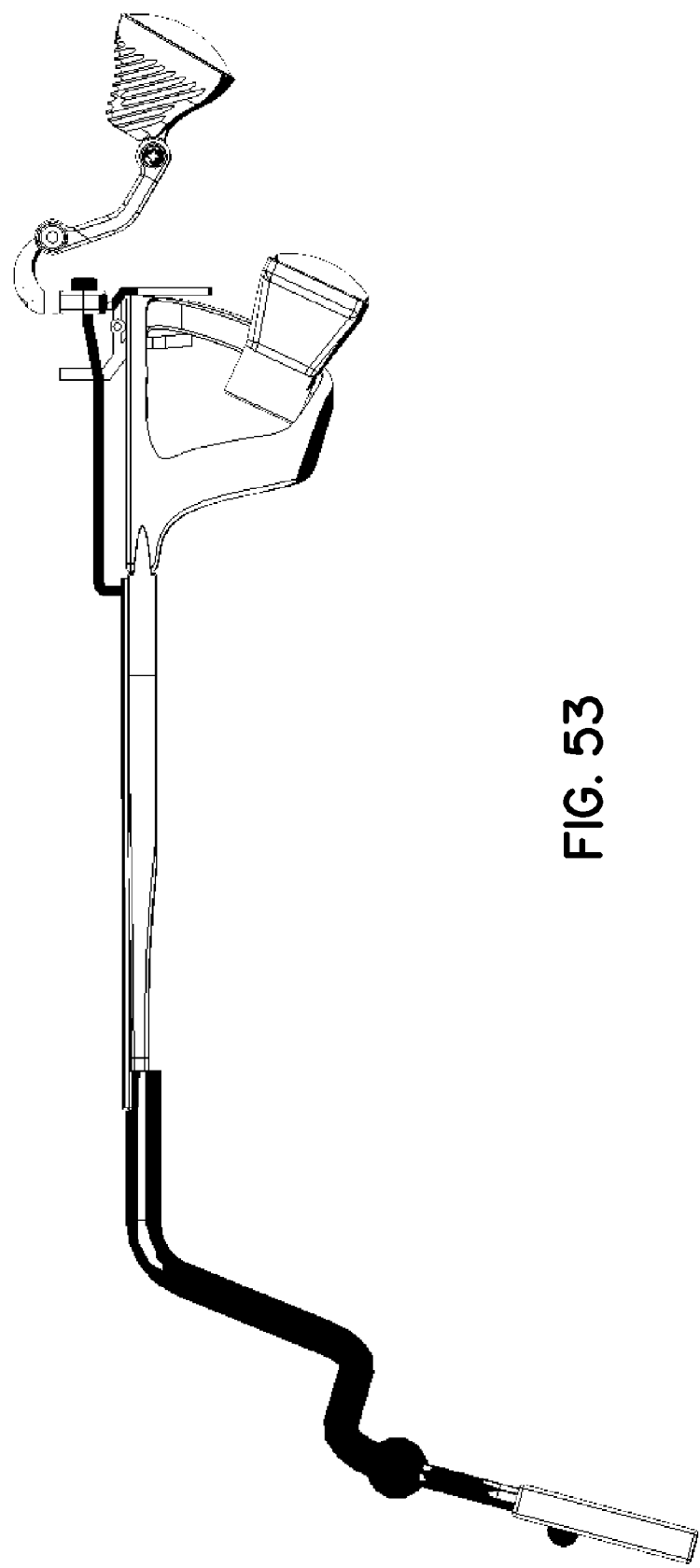
FIG. 53 is a right-side elevation view thereof.
Figure 54:
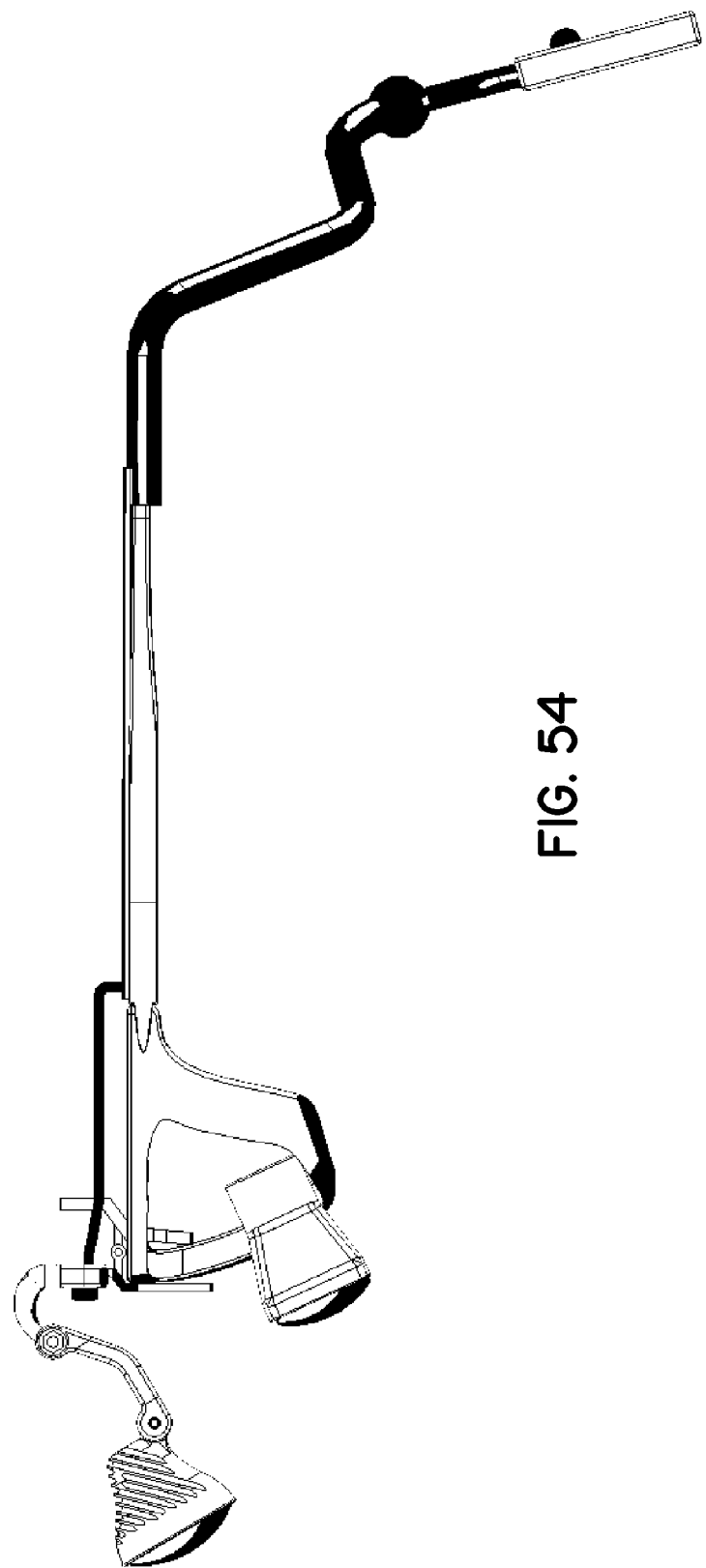
FIG. 54 is a left-side elevation view thereof.
Figure 55:
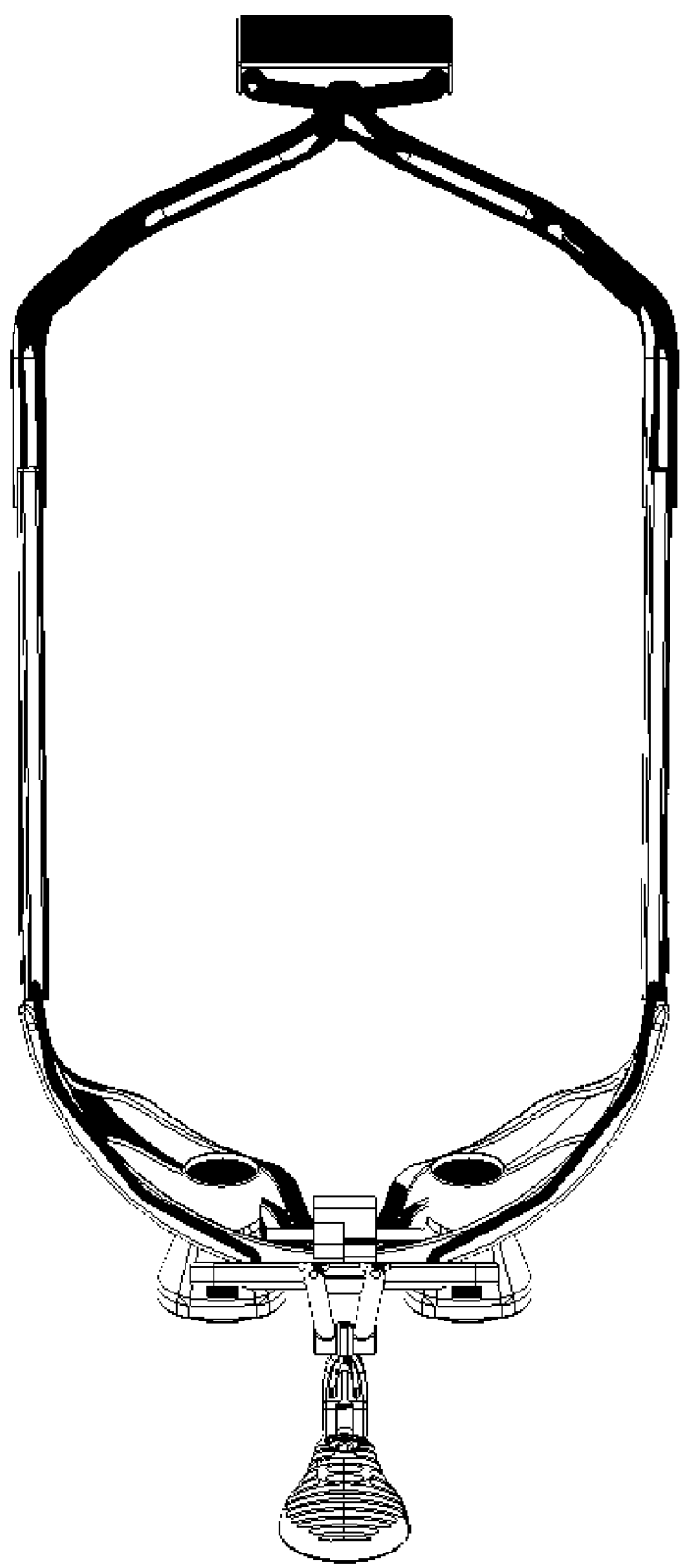
FIG. 55 is a top plan view thereof.
Figure 56:
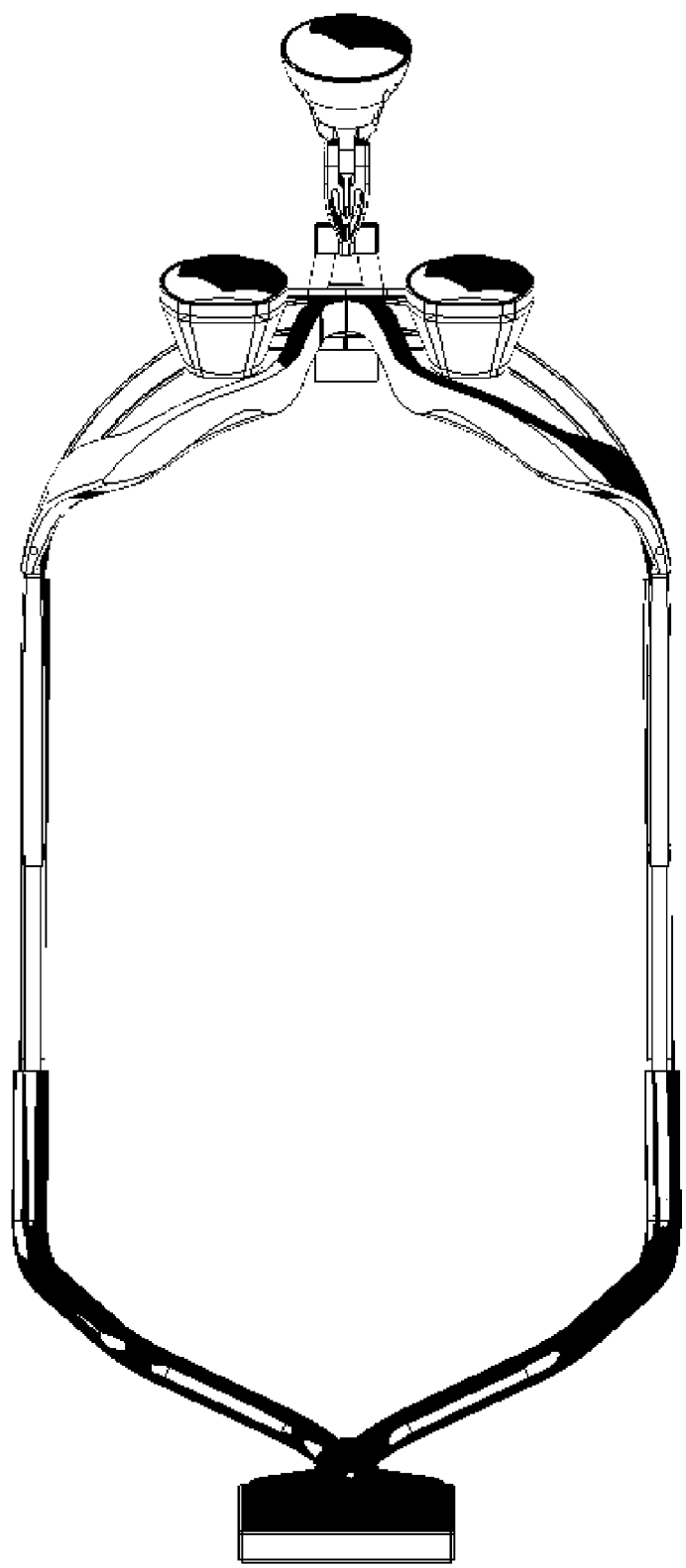
FIG. 56 is a bottom plan view thereof.
Figure 57:
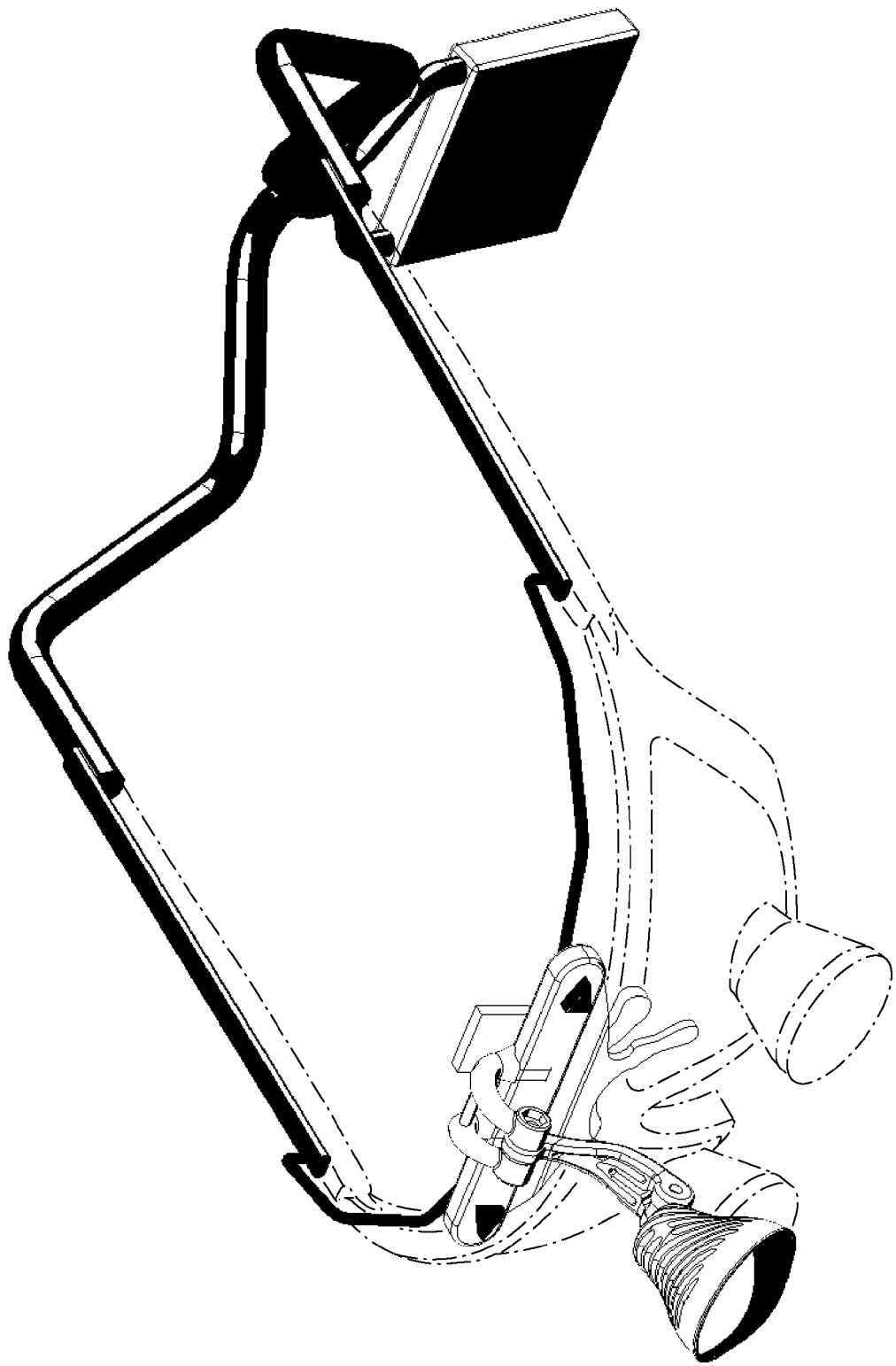
FIG. 57 is a perspective view of another exemplary embodiment of a user-wearable illumination assembly of FIG. 32, illustrating the ornamental design of the embodiment and depicting eyeglass frames in phantom.
Figure 58:
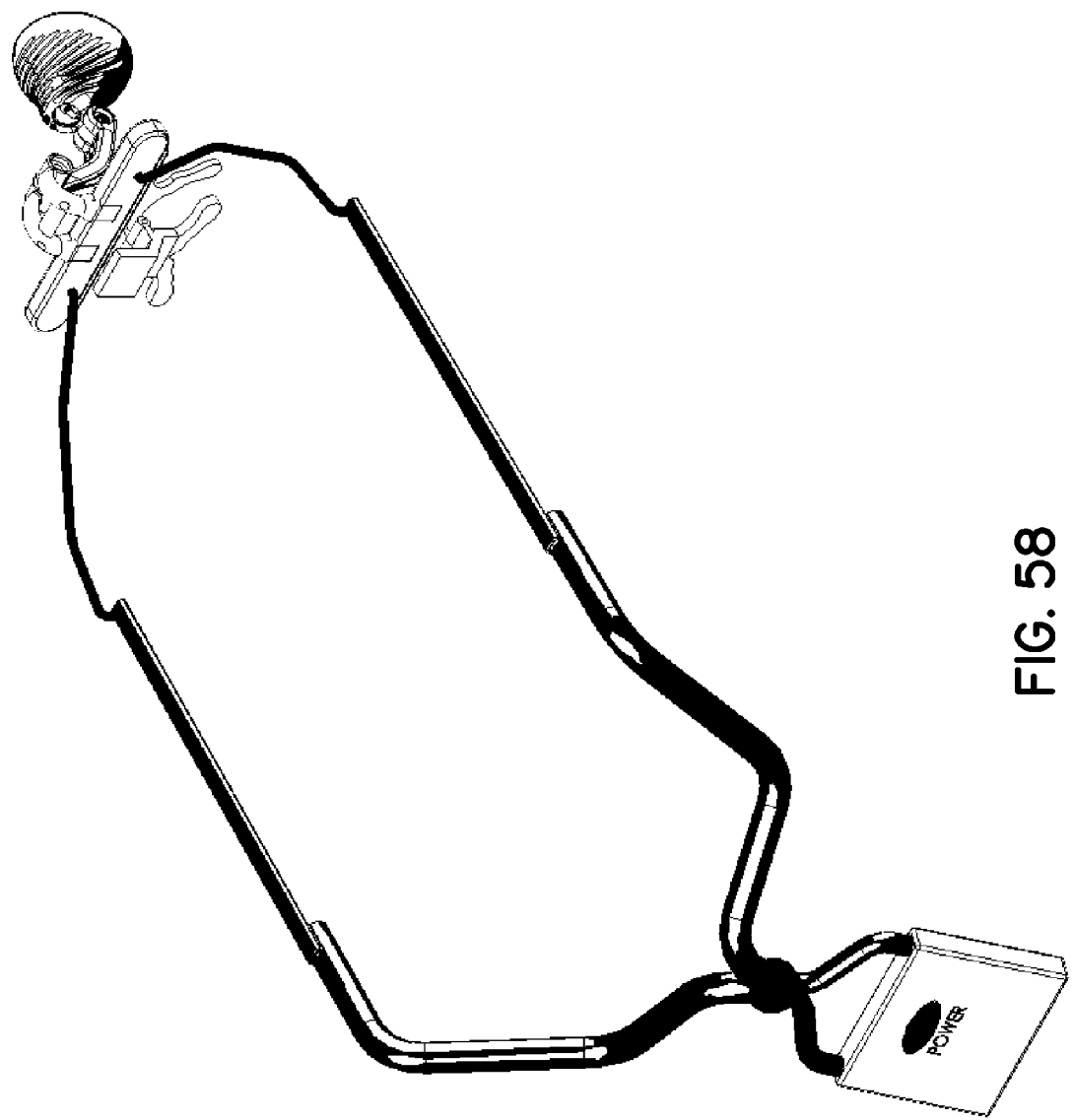
FIG. 58 is another perspective view of the user-wearable illumination assembly of FIG. 57, viewed from another direction.
Figure 59:
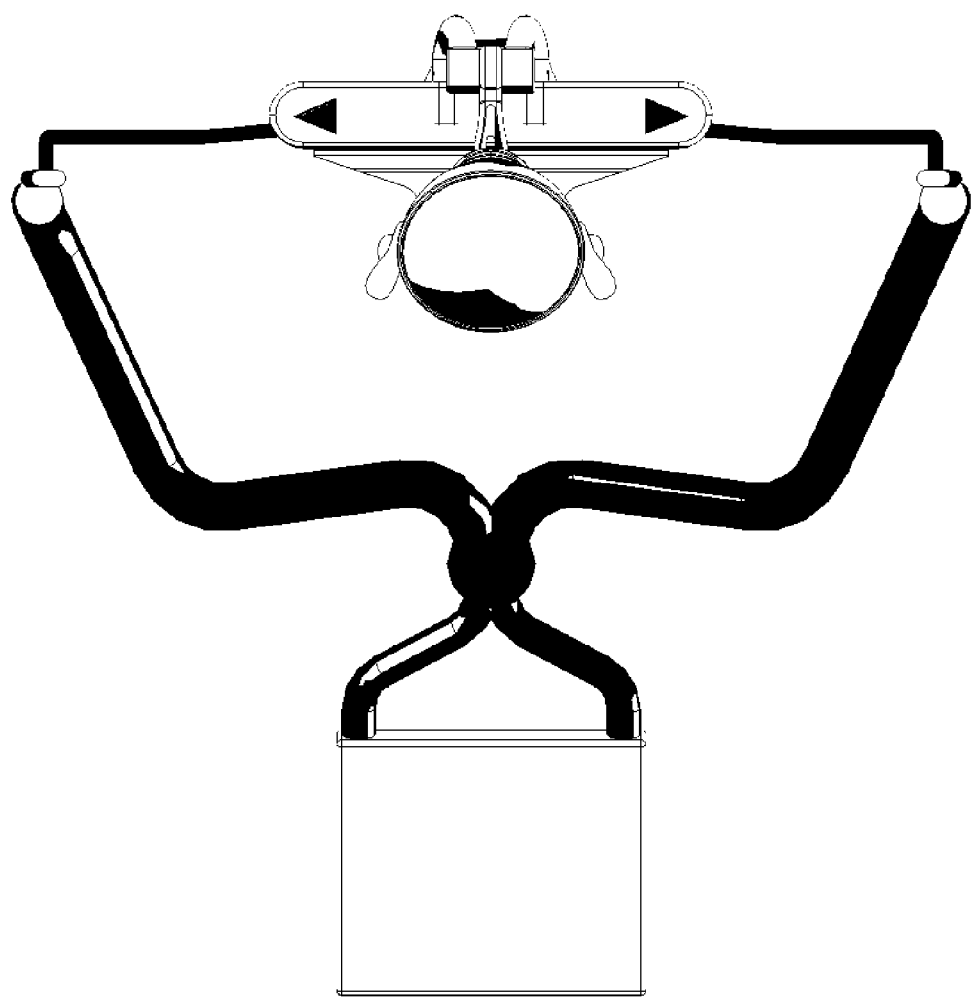
FIG. 59 is a front elevation view thereof.
Figure 60:
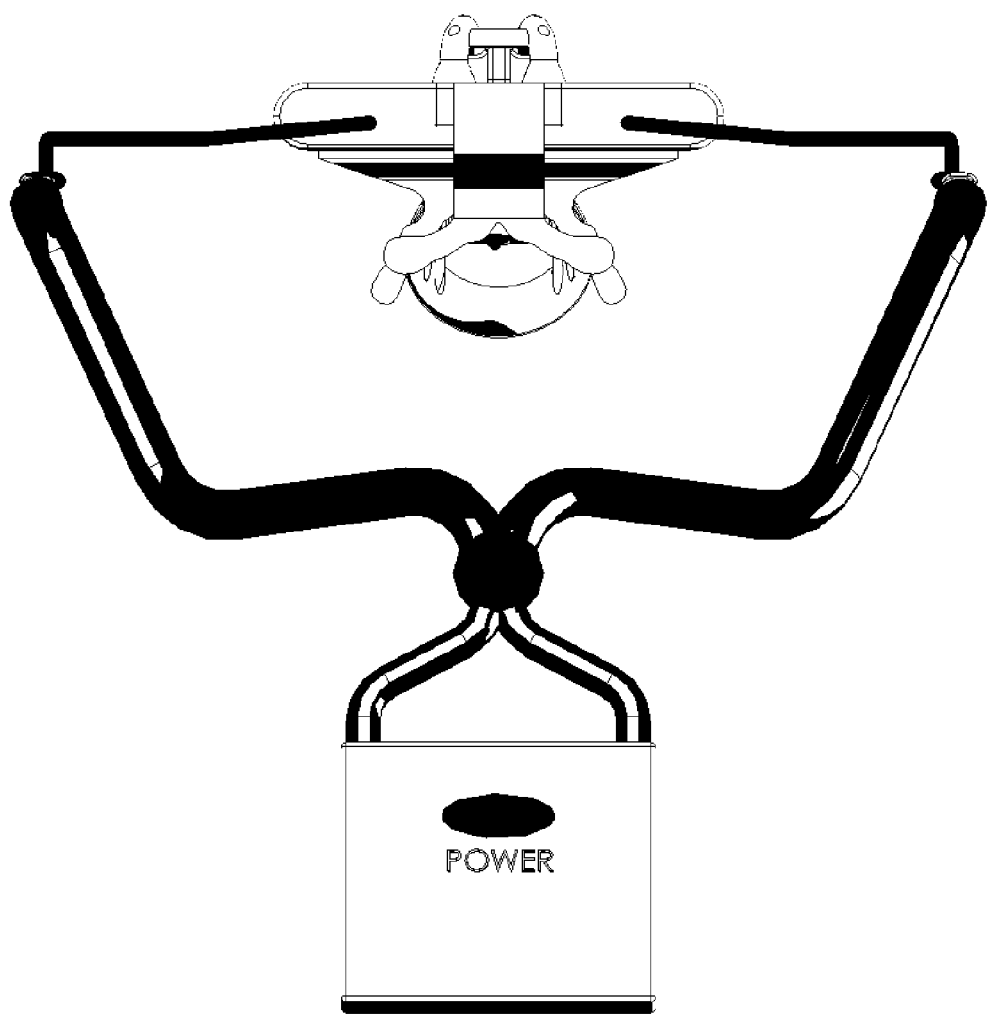
FIG. 60 is a rear elevation view thereof.
Figure 61:
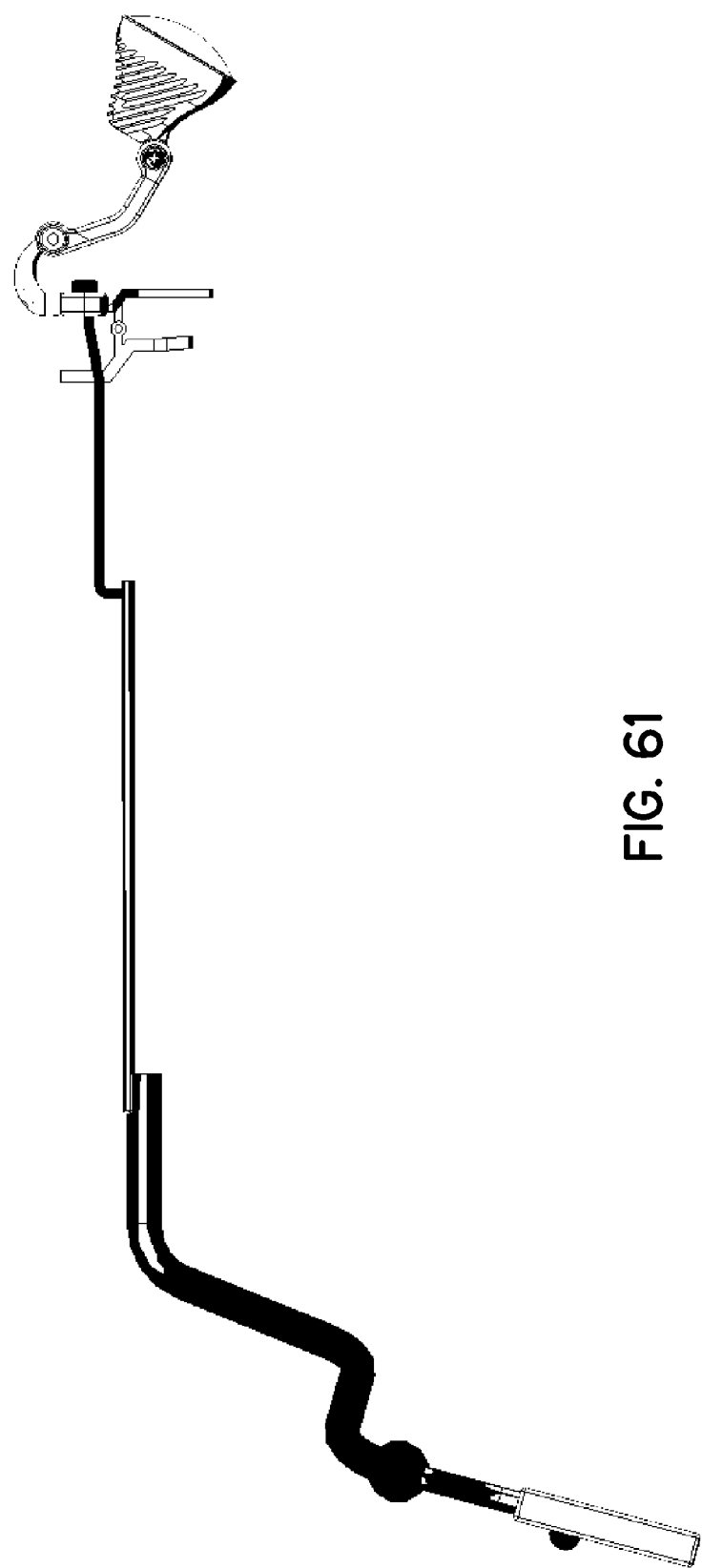
FIG. 61 is a right-side elevation view thereof.
Figure 62:
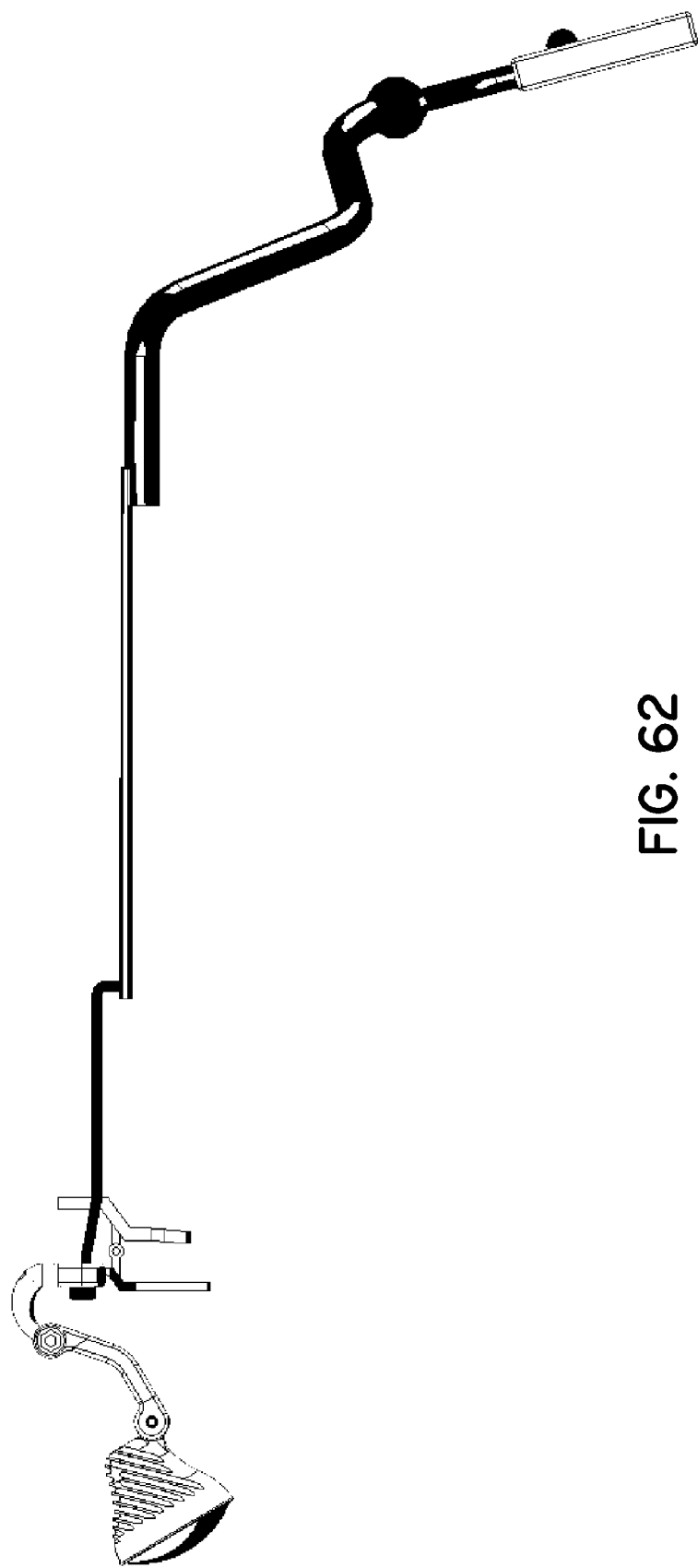
FIG. 62 is a left-side elevation view thereof.
Figure 63:
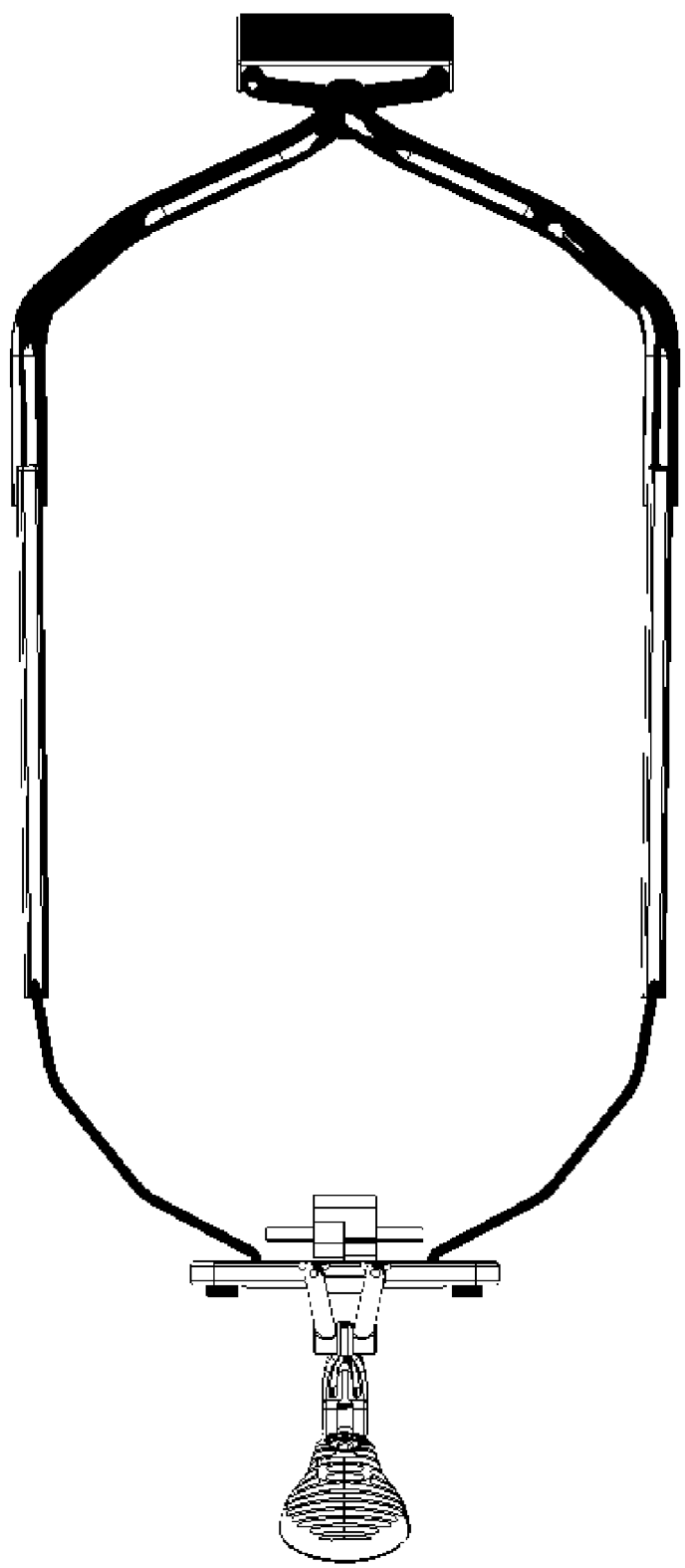
FIG. 63 is a top plan view thereof.
Figure 64:
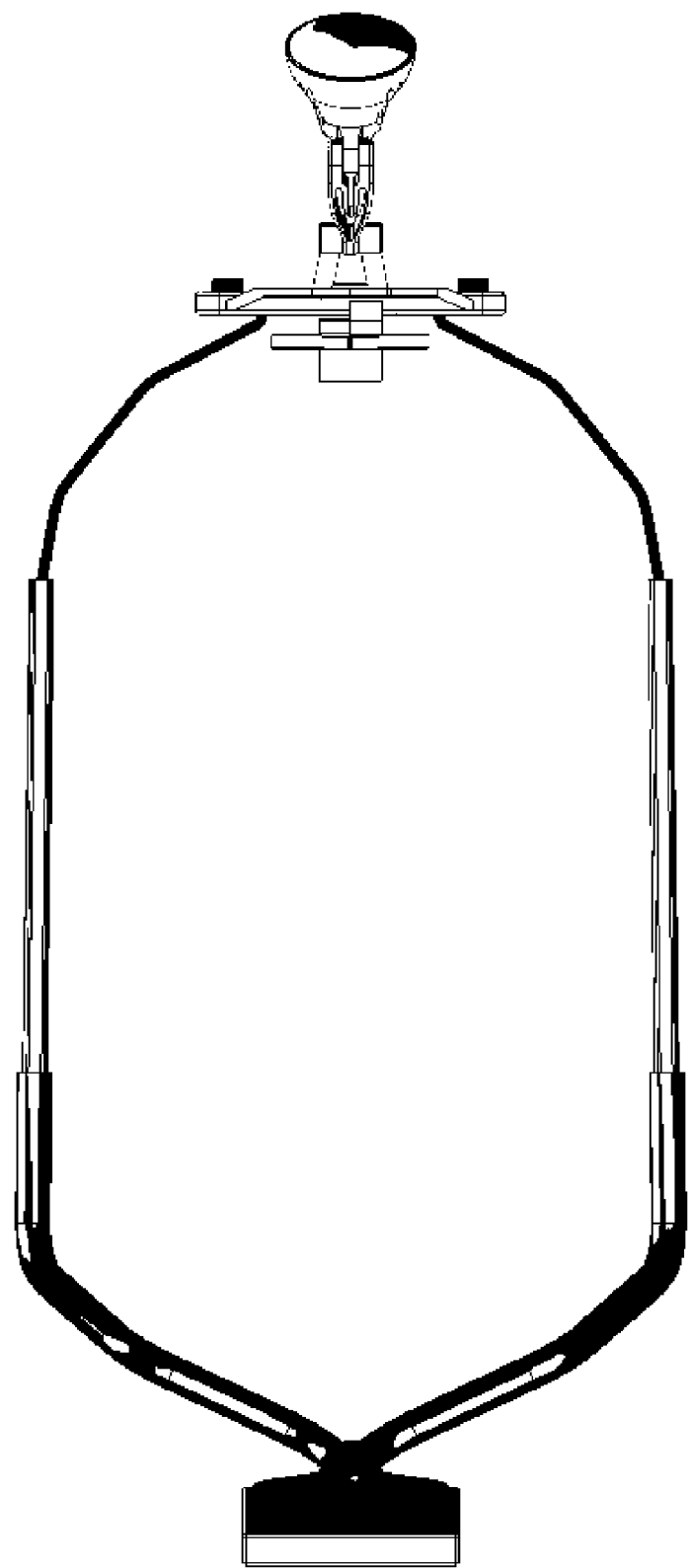
FIG. 64 is a bottom plan view thereof.

In another aspect, battery 282 may be configured with smart battery technology, as discussed above with respect to batteries 260a, 260b. Battery 282 may further include user actuatable controls to facilitate operation of the illumination assembly 280, such as a button 283 for selectively activating and deactivating power to headlamp 240. It will be appreciated that user-actuatable controls may also be provided on various other structure of the illumination assembly 280 to facilitate operation by a user of the device. For example, illumination assembly 280 may further include one or more controls, such as buttons 290a, 290b, on body portion 232 of clip assembly 230, as depicted in FIG. 49. In the embodiment illustrated, buttons 290a, 290b may be actuated by a user to selectively adjust the intensity of the light emitted by light source 256, or to control various other functions of the illumination assembly 280. Similar features may optionally be provided on the illumination assembly 210 shown and described above.

Figure 65:
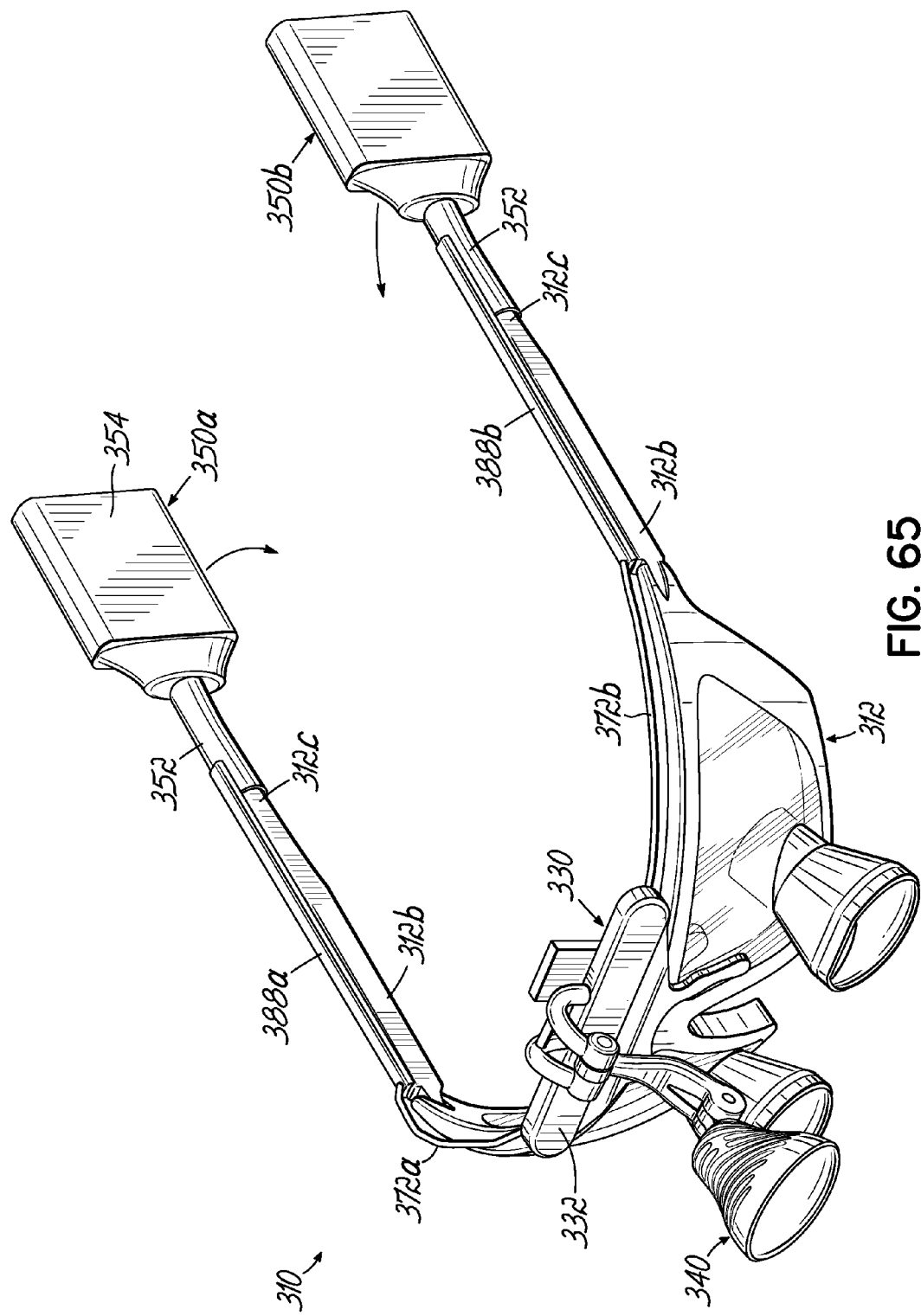
FIG. 65 is a perspective view of another exemplary user-wearable illumination assembly for use with eyeglass frames in accordance with the present disclosure.

FIG. 65 depicts another exemplary embodiment of a user-wearable illumination assembly 310 for use with eyeglass frames 312 in accordance with the present disclosure. The user-wearable illumination assembly 310 of this embodiment includes a clip assembly 330 and headlamp 340 similar to that the clip assembly 230 and headlamp 240 of user-wearable illumination assemblies 210 and 280 shown and described with respect to FIGS. 27-31, 32, 33, 33A, and 49-56. The various features of clip assembly 330 and headlamp 340 that are similar to the features of clip assembly 230 and headlamp 240 are numbered in a similar manner, the details of which are not repeated here.

The user-wearable illumination assembly 310 further includes lithium polymer batteries 350a, 350b provided on respective sides of the eyeglass frames 312 and positioned proximate the terminal ends 312c of the temple arms 312b in a manner similar to the batteries 150a, 150b of the illumination assembly 110 shown and described with respect to FIGS. 22-26A. In this embodiment, the batteries 350a, 350b are removably coupled to the terminal ends 112c of the temple arms 112b to provide a counterbalance to the weight of the headlamp 120 and/or optical loupes 118a, 118b, as may be desired. To this end, the batteries 350a, 350b include an attachment portion 352 that can be slidably received over the terminal ends 312c of the temple arms 312b of the eyeglass frames 312. The attachment portions 352 may be formed from flexible material to facilitate selective adjustment of the position of the batteries 350a, 350b supported on the terminal ends 312c of the temple arms 312b, such that the inside surfaces 354 of the batteries 350a, 350b can be positioned to engage the head of the user in a manner similar to that described above with respect to user-wearable illumination assembly 110. While the batteries 350a, 350b are shown and described in this embodiment as being positionably adjustable by flexible attachment portions 352, it will be appreciated that batteries 350a, 350b may alternatively be hingedly coupled to the terminal ends 312c of temple arms 312b to facilitate adjustment, or that the batteries may be made positionally adjustable by various other methods.

The user-wearable illumination assembly 310 may further include control circuitry and one or more electrical conductors for controlling a light source and for providing electrical communication between the batteries 350a, 350b and the light source of the headlamp 340, as described above with respect to user-wearable illumination assembly 210. Various other features of the user-wearable illumination assembly 310 and batteries 350a, 350b are similar to those of the user-wearable illumination assembly 210 and batteries 150a, 150b described herein.

Figure 66:
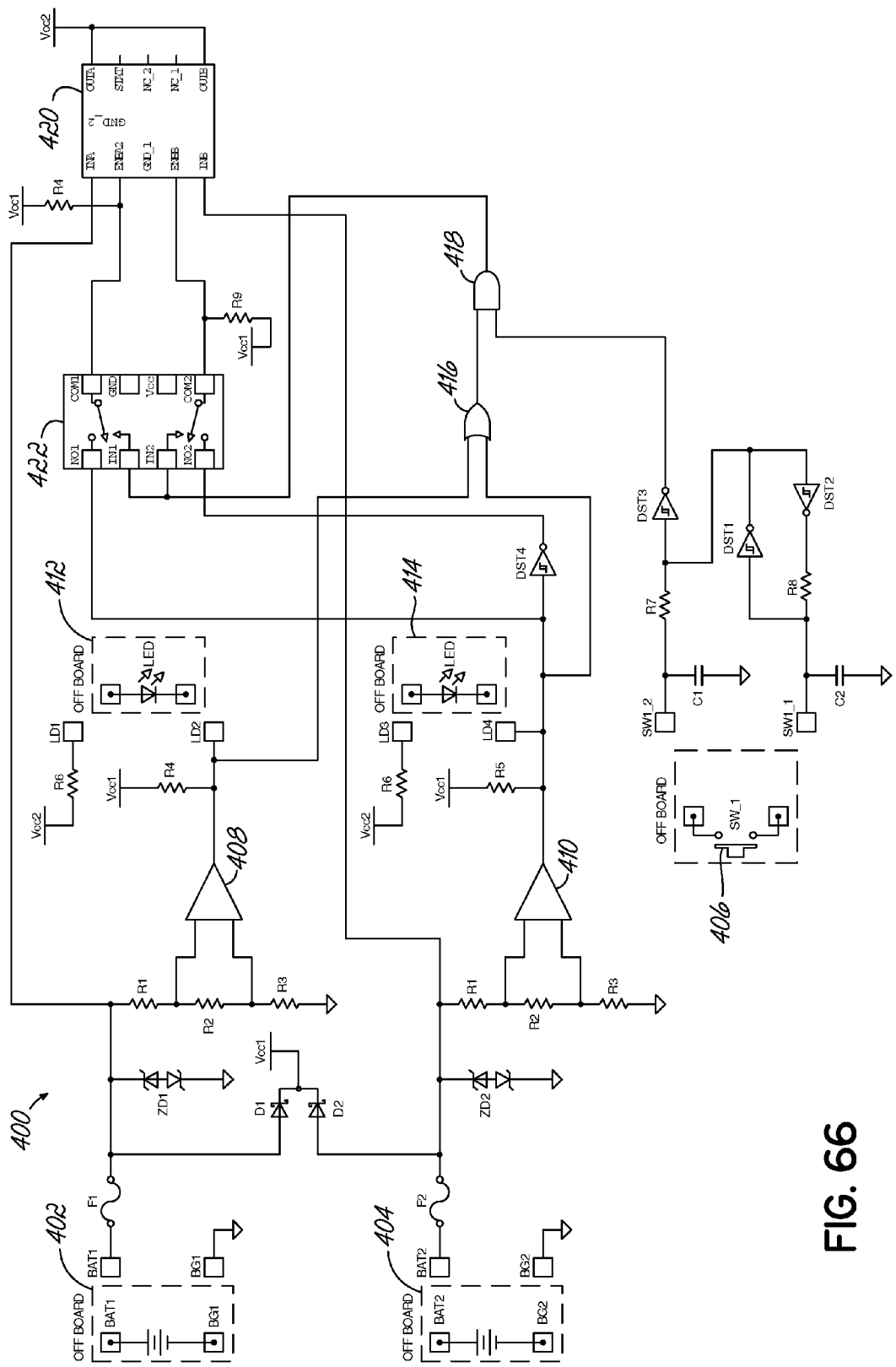
FIG. 66 is a diagrammatic illustration of an exemplary power supply circuit that may be used with a user-wearable illumination assembly in accordance with the present disclosure.
Figure 67:
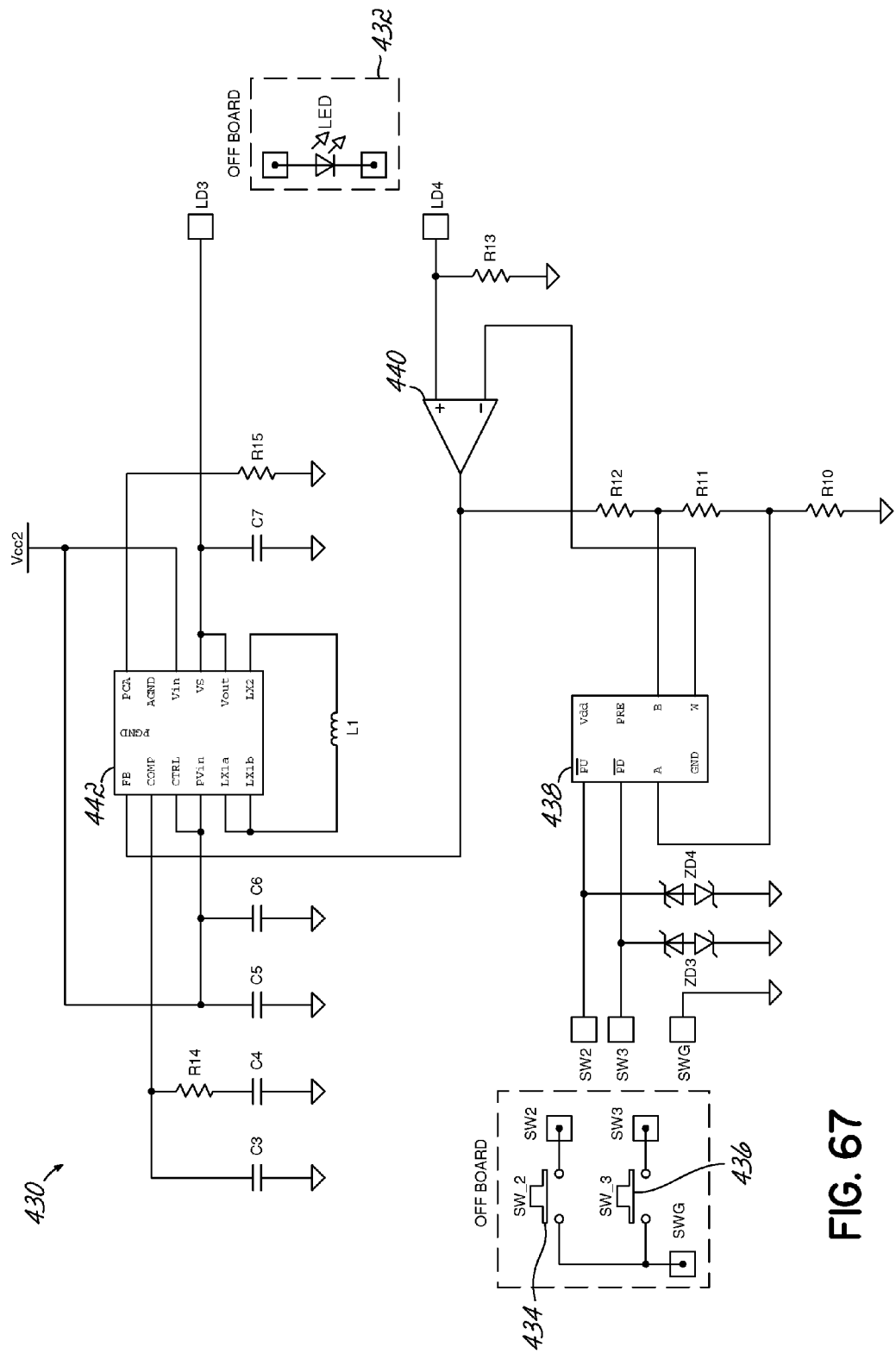
FIG. 67 is a diagrammatic illustration of an exemplary intensity circuit that may be used with a user-wearable illumination assembly.

FIG. 66 is a diagrammatic illustration of one embodiment of a power supply circuit 400 that may be configured on and/or within the illumination assembly 10 consistent with embodiments of the invention. In particular, and as illustrated in FIG. 67, the power supply circuit 400 is provided power from at least two battery packs 402 and 404 (which may each be Li-Ion polymer battery packs). The power supply circuit 400 is also in communication with a first switch 406 (illustrated as "SW_1"), which may operate to turn the power supply circuit 400 (and thus the remaining circuitry of the illumination assembly 10) on and off. As illustrated in FIG. 66, each of the battery packs 402 and 404 may be in communication with a respective fuse F1 and F2, which may be 1.5 A fuses. The output of the fuses F1 and F2 is in turn in communication with the anode end of Zener diodes D1 and D2 (which may be BAT54C series Schottky barrier diodes as distributed by Fairchild Semiconductor International, Inc. of South Portland, Me.). The Zener diodes D1 and D2, in turn, each have their cathode ends in communication with a first power signal VCC1 (which, in exemplary embodiments, may be about 3.7V). The output of the fuses F1 and F2 are also in communication with ground through Zener diode arrays ZD1 and ZD2, respectively, wherein each Zener diode array includes two Zener diodes in an anode-to-anode configuration.

The output of the fuses F1 and F2 is also in communication with a respective resistor R1. Each resistor R1 is positioned between the output of a fuse (e.g., fuse F1 or F2) and a first input of a respective buck-boost converter 408 and 410. A resistor R2 is in communication with resistor R2, the first input of the respective buck-boost converter 408 and 410, and a second input of the respective buck-boost converter 408 and 410. In turn, a resistor R3 is in communication with respective resistor R2, the second input of respective buck-boost converter 408 and 410, and a respective ground. The output of the first buck-boost converter 408 is in communication with the first power signal VCC1 through a resistor R4, while the second buck-boost converter 410 is in communication with the first power signal VCC1 through a resistor R5. The output of each buck-boost converter 408 and 410 is also in communication with a respective light-emitting diode 412 and 414 (first LED 412 and second LED 414, respectively) that receives a second power signal VCC2 (which, in exemplary embodiments, may be about 3.7V) through a resistor R6. As illustrated in FIG. 67, the output of each buck-boost converter 408 and 410 is also in communication with an OR gate 416 (which may be a NLU1G32 series 2-input OR gate as distributed by ON Semiconductor, Inc. of Phoenix, Ariz.).

A first output of the first switch 406 is in communication with ground through a resistor C1 while a second output of the first switch 406 is in communication with ground through a resistor C2. The first output of the first switch 406 is also in communication with a resistor R7, while the second output of the first switch 406 is in communication with, in parallel, an input of a first dual Schmitt trigger inverter DST1 (where each dual Schmitt trigger inverter may be a NLU2G14 series dual Schmitt trigger inverter as distributed by ON Semiconductor) in one branch and a resistor R8 in series with an output of a second dual Schmitt trigger inverter DST2 in the second branch. In turn, the parallel circuit is in communication with the output from the resistor R7 and an input of a third dual Schmitt trigger inverter DST3.

As illustrated in FIG. 66, the output of the OR gate 415 is in communication with a first input of an AND gate 418 (which may be an NLU1G08 series 2-input AND gate as distributed by ON Semiconductor) and the output from the third dual Schmitt trigger inverter DST3 is in communication with a second input of the AND gate 418.

Returning to fuses F1 and F2, the output of fuses F1 and F2 are in communication with a respective first input and second input of a converter chip 420 (which may be an LTC4413 series dual 2.6 A, 2.5V to 5.5V chip as distributed by Linear Technology of Milpitas, Calif.). In turn, the converter chip 420 is in communication with a switch chip 422 (which may be an NLAS5213 series 1Ω $R_{ON}$ DPST and dual SPST switch chip as distributed by ON Semiconductor). Two inputs of the converter chip 420 are also separately in communication with the first power signal VCC1 through two respective resistors R9. As illustrated in FIG. 66, one input to the switch ship 422 is in communication with the output from the second buck-boost converter 410, a second input to the switch chip 422 is in communication with an output of a fourth dual Schmitt trigger inverter DST4, while a third and a fourth input to the switch chip 422 are tied together and in communication with the output from the AND gate 418.

In specific embodiments, the power supply circuit 400 is configured to regulate and monitor the power from battery packs 402 and 404 and provide power to additional components of the illumination assembly 10. Specifically, the power supply circuit 400 electronically selects which battery pack 402 or 404 is used to provide power and also allows for the battery packs to be "hot-swappable" (e.g., one battery pack can be changed while the other supplies power). Moreover, when the illumination assembly 10 is turned off, the power supply circuit disconnects both battery packs 402 and 404 from supplying main power but allows power to at least one additional component of the illumination assembly 10 to keep a previous intensity setting. In further specific embodiments, Table 1 indicates approximate resistor and capacitor values that may be used for the resistors R1-R9 as well as the capacitors C1-C2 illustrated and described.

TABLE 1

Approximate Values for Resistors R1-R9 and Capacitors C1-C2

| Resistor | Value | Capacitor | Value |
|---|---|---|---|
| R1 | 604 kΩ | C1 | 470 nF |
| R2 | 56 kΩ | C2 | 10 µF |
| R3 | 340 kΩ | | |
| R4 | 10 kΩ | | |
| R5 | 10 kΩ | | |
| R6 | 2 kΩ | | |
| R7 | 1 MΩ | | |
| R8 | 220 kΩ | | |
| R9 | 10 kΩ | | |

One having ordinary skill in the art will appreciate that alternative components may be utilized in the power supply circuit 400 consistent with alternative embodiments of the invention. Specifically, the power supply circuit 400 may include more or fewer battery packs, switches, or LEDs consistent with alternative embodiments of the invention. One having ordinary skill in the art will appreciate that the specific components illustrated and described, and the specific values of resistors and capacitors, are not intended to be limiting. Moreover, one having ordinary skill in the art and the benefit of this disclosure will appreciate that at least some of the connections for power signals and/or to ground, as well as additional resistors, capacitors, and inductors, used to provide the power signals to the components of the power supply circuit 400 are not illustrated. However, such power and ground connections, and such additional resistors, capacitors, and inductors, are known and available to one having ordinary skill in the art.

FIG. 67 is a diagrammatic illustration of one embodiment of an intensity circuit 430 to adjust the brightness of a third LED 432. Specifically, the intensity circuit receives inputs from a second switch 434 and a third switch 436 (illustrated as "SW_2" and "SW_3," respectively). An output from each of the second and third switches 434 and 436 is in communication with respective grounds through third and fourth Zener diode arrays ZD3 and ZD4, respectively. The outputs from each of the second and third switches 434 and 436 are also in communication with respective inputs of a digital potentiometer 438 (which may be an AD5228 digital potentiometer as distributed by Analog Devices, Inc. of Norwood, Mass.). In turn, a first output of the digital potentiometer 438 is in communication with ground through a resistor R10. The first output of the digital potentiometer 438 is in turn in communication with a second output of the digital potentiometer through a resistor R11. The second output of the digital potentiometer 438 is also in communication with an output of an operational amplifier 440 (which may be an LT6220 series operational amplifier as distributed by Linear Technology) (hereinafter, "op-amp" 440) through a resistor R12. A third output of the digital potentiometer 438 is in communication with the negative input of the op-amp 440. The positive input of the op-amp 440 is in communication with ground through a resistor R13 as well as the cathode side of the third LED 432. Thus, and in some embodiments, the op-amp 440 acts as a current-to-voltage amplifier.

The output of the op-amp 440 is in communication with a first input of a buck-boost converter 442 (which may be an NCP5030 series buck-boost converter to drive an LED as distributed by ON Semiconductor). In turn, a second input of the buck-boost converter 442 is in communication with, in parallel, a capacitor C3 connected to ground in one branch and a resistor R14 in series with a capacitor C4 connected to ground in another branch. A third and fourth input of the buck-boost converter 442 are tied together and are in communication with the second voltage signal VCC2 as well as, in parallel, a capacitor C5 connected to ground in one branch and a capacitor C6 connected to ground in a another branch. A fifth input of the buck-boost converter 442 is also in communication with the second voltage signal VCC2 for power.

As illustrated in FIG. 67, a sixth and seventh input of the buck-boost converter 442 are tied together and in communication with one end of an inductor L1, with the other end of the inductor L1 in communication with a seventh input of the buck-boost converter 442. A first output of the buck-boost converter 442 is in communication with ground through a resistor R15 while a second output of the buck-boost converter 442 is in communication with ground through a capacitor C7. The second output is also in communication with the third LED 432.

In specific embodiments, the intensity circuit 430 allows the user to control the intensity of the third LED 432. Specifically, the intensity of the third LED 432 is controlled by the digital potentiometer 438 whose value is controlled by the second and third switches 434 and 436, with the second switch 434 operating as an "intensity increase" switch (e.g., depression of the second switch 434 operates to increase the intensity of the third LED 432), and the third switch 436 operating as an "intensity decrease" switch (e.g., depression of the second switch 434 operates to decrease the intensity of the third LED 432). In specific embodiments, the digital potentiometer 438 provides about 32 step levels with an autoscan function (in which the resistance of the digital potentiometer 438 rapidly increases or decreases automatically) when either switch 434 or 436 is held down for about a second. In further specific embodiments, Table 2 indicates approximate resistor, capacitor, and inductor values that may be used for the resistors R10-R15, capacitors C3-C7, and the inductor L1 illustrated and described.

TABLE 2

Approximate Values for Resistors R10-R15, Capacitors C3-C7, and Inductor L1

| Resistor | Value | Capacitor | Value | Inductor | Value |
|---|---|---|---|---|---|
| R10 | 100 Ω | C3 | 22 pF | L1 | 4.7 µH |
| R11 | 220 Ω | C4 | 300 pF | | |
| R12 | 1.8 kΩ | C5 | 10 µF | | |
| R13 | 100 mΩ | C6 | 1 µF | | |
| R14 | 68 kΩ | C7 | 22 µF | | |
| R15 | 100 kΩ | | | | |

While the intensity circuit 430 is described above with a digital potentiometer 438, it will be appreciated that an intensity circuit for controlling the brightness of an LED may alternatively comprises a microcontroller. One having ordinary skill in the art will also appreciate that alternative components may be utilized in the intensity circuit 430 consistent with alternative embodiments of the invention. Specifically, the intensity circuit 430 may include more or fewer switches or LEDs consistent with alternative embodiments of the invention. One having ordinary skill in the art will appreciate that the specific components illustrated and described, and the specific values of resistors, capacitors, and inductors, are not intended to be limiting. Moreover, one having ordinary skill in the art and the benefit of this disclosure will appreciate that at least some of the connections for power signals and/or to ground, as well as additional resistors, capacitors, and inductors, used to provide the power signals to the components of the intensity circuit 430 are not illustrated. However, such power and ground connections, and such additional resistors, capacitors, and inductors, are known and available to one having ordinary skill in the art.

Figure 68A:
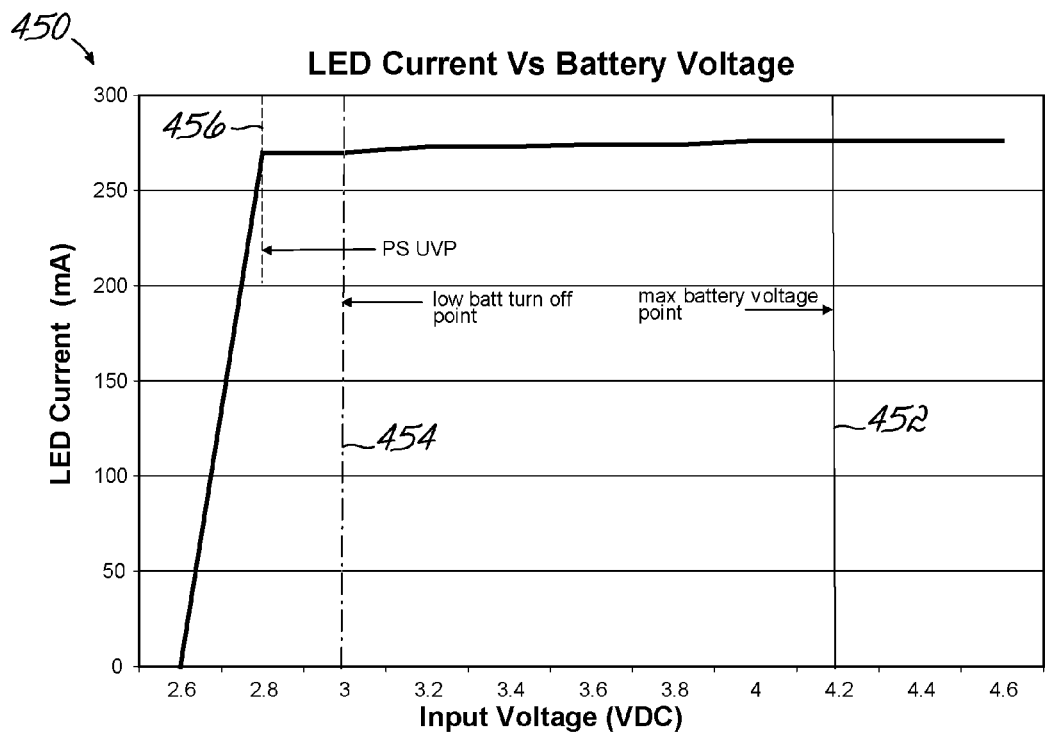
FIG. 68A is a graphical illustration of LED current versus battery voltage in accordance with one embodiment.

FIG. 68A is a diagrammatic illustration of a graphical representation 450 illustrating the level of input current to the third LED 432 with respect to the voltage provided at least one battery pack 402 or 404. In particular, the graphical representation 450 illustrates both the maximum battery voltage point as at 452 (e.g., the voltage corresponding to about the highest safe voltage from a battery pack 402 and/or 404) as well as the low battery turn off point as at 454 (e.g., the voltage corresponding to about the lowest safe voltage from a battery pack 402 and/or 404). Moreover, the graphical representation 450 indicates the power supply undervoltage protection cut-off point as at 456. As illustrated in FIG. 68A, the power supplied to the third LED 432 is approximately constant across the range of voltage from about 2.8V to about 4.6V.

Figure 68B:
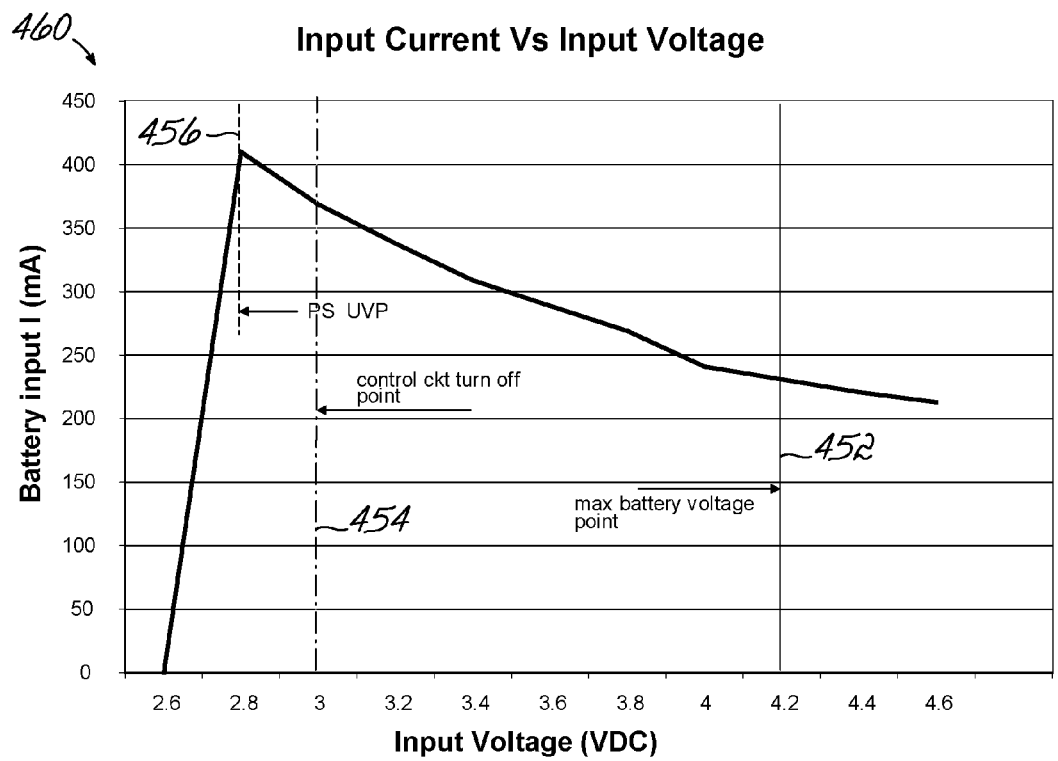
FIG. 68B is a graphical illustration of current input into a power supply circuit versus input voltage from a battery source in accordance with one embodiment.

FIG. 68B is a diagrammatic illustration of a graphical representation 460 illustrating the level of input current to at least the power supply circuit 400 and/or intensity circuit 430 from the battery pack 402 and/or 404 with respect to the input voltage from the battery pack 402 and/or 404. As illustrated in FIG. 68B, the current from the battery pack 402 and/or 404 has a relatively stable negative slope in relation to increasing voltage from about 2.8V to about 4.6V.

Figure 68C:
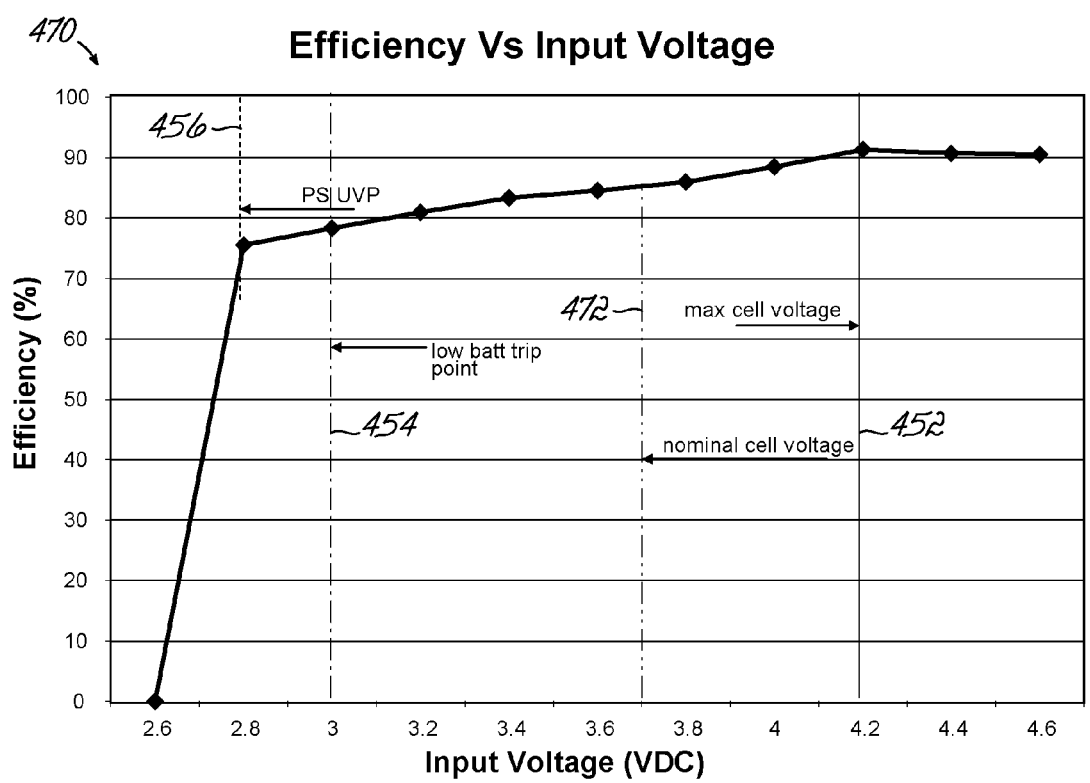
FIG. 68C is a graphical illustration of efficiency versus input voltage from a battery source in accordance with one embodiment.

FIG. 68C is a diagrammatic illustration of a graphical representation 470 illustrating the efficiency of at least the power supply circuit 400 and/or intensity circuit 430 with respect to the input voltage from the battery pack 402 and/or 404. In particular, the graphical representation 470 illustrates the nominal cell voltage as at 472 (e.g., the nominal voltage at which the battery pack 402 and/or 404 will typically operate). As illustrated in FIG. 68C, the circuitry of the illumination assembly 10 operates at about 85% efficiency at the nominal cell voltage 472.

While the present invention has been illustrated by the description of one or more embodiments thereof, and while the embodiments have been described in considerable detail, they are not intended to restrict or in any way limit the scope of the appended claims to such detail. The various features shown and described herein may be used alone or in any combination. Additional advantages and modifications will readily appear to those skilled in the art. The invention in its broader aspects is therefore not limited to the specific details, representative apparatus and method and illustrative examples shown and described. Accordingly, departures may be made from such details without departing from the general inventive concept.

What is claimed is:

1. A user-wearable illumination assembly, comprising:
   eyeglass frames comprising first and second temple arms, each of the first and second temple arms having a terminal end opposite a front portion of the eyeglass frames;
   a first mounting structure on a bridge of said eyeglass frames;
   a first electrical contact associated with said first mounting structure;
   a headlamp comprising:
      a housing,
      a light source supported within said housing,
      a second mounting structure on said housing cooperating with said first mounting structure on the bridge of said eyeglass frames to removably support said headlamp on said eyeglass frames, and
      a second electrical contact associated with said second mounting structure;
   a first battery housing coupled to the terminal end of the first temple arm for removably receiving a first battery;
   a second battery housing coupled to the terminal end of the second temple arm for removably receiving a second battery; and
   electrical circuitry integrated with said eyeglass frames and configured to provide electrical communication with said headlamp via said first and second electrical contacts when said second mounting structure is coupled to said first mounting structure to support said headlamp on said eyeglass frames;
   wherein each of the first and second battery housings is positionably adjustable relative to its respective temple arm.

2. The user-wearable illumination assembly of claim 1, wherein said first and second batteries are rechargeable, and wherein the user-wearable illumination assembly further comprises an indicator associated with said first and second batteries and configured to indicate a charge level of said first and second batteries.

3. The user-wearable illumination assembly of claim 1, further comprising at least one optical loupe coupled to said eyeglass frames to provide magnified viewing through said loupe.

4. The user-wearable illumination assembly of claim 1, further comprising user-actuable controls on the headlamp, said controls operable to turn said light source on and off and to selectively adjust an output intensity of said light source.

5. The user-wearable illumination assembly of claim 1, further comprising:
   a first battery received within the first battery housing; and
   a second battery received within the second battery housing.

6. The user-wearable illumination assembly of claim 1, wherein each of the first and second battery housings comprises a flexible connecting structure coupled to the terminal end of the respective terminal arm to facilitate positionably adjusting the first and second battery housings relative to the respective temple arm.

7. The user-wearable illumination assembly of claim 1, wherein each of the first and second battery housings is pivotally coupled to the terminal end of the respective temple arm.

8. The user-wearable illumination assembly of claim 1, wherein each of the first and second battery housings is hingedly coupled to the terminal end of the respective temple arm.

* * * * *